United States Patent
Dotti et al.

(10) Patent No.: US 12,428,490 B2
(45) Date of Patent: Sep. 30, 2025

(54) METHODS AND COMPOSITIONS FOR CHIMERIC ANTIGEN RECEPTOR TARGETING CANCER CELLS

(71) Applicants: The University of North Carolina at Chapel Hill, Chapel Hill, NC (US); The General Hospital Corporation, Boston, MA (US)

(72) Inventors: Gianpietro Dotti, Chapel Hill, NC (US); Soldano Ferrone, Boston, MA (US); Hannah Reid Hudson, Durham, NC (US); Elena Dukhovlinova, Chapel Hill, NC (US); Cristina Ferrone, Boston, MA (US); Xinhui Wang, Boston, MA (US)

(73) Assignees: The University of North Carolina at Chapel Hill, Chapel Hill, NC (US); The General Hospital Corporation, Boston, MA (US)

( * ) Notice: Subject to any disclaimer, the term of this patent is extended or adjusted under 35 U.S.C. 154(b) by 1059 days.

(21) Appl. No.: 17/251,397

(22) PCT Filed: May 24, 2019

(86) PCT No.: PCT/US2019/034027
§ 371 (c)(1),
(2) Date: Dec. 11, 2020

(87) PCT Pub. No.: WO2019/240935
PCT Pub. Date: Dec. 19, 2019

(65) Prior Publication Data
US 2021/0252067 A1    Aug. 19, 2021

Related U.S. Application Data

(60) Provisional application No. 62/684,513, filed on Jun. 13, 2018.

(51) Int. Cl.
| | | |
|---|---|---|
| C07K 16/40 | (2006.01) | |
| A61K 39/00 | (2006.01) | |
| C07K 14/725 | (2006.01) | |
| C07K 16/30 | (2006.01) | |
| G01N 33/50 | (2006.01) | |

(52) U.S. Cl.
CPC ...... C07K 16/3053 (2013.01); A61K 39/4611 (2023.05); A61K 39/4631 (2023.05); A61K 39/464474 (2023.05); C07K 14/7051 (2013.01); G01N 33/5091 (2013.01)

(58) Field of Classification Search
CPC .............. A61K 35/17; C07K 14/7051; C07K 16/3053; G01N 33/5091
See application file for complete search history.

(56) References Cited

U.S. PATENT DOCUMENTS

| | | |
|---|---|---|
| 4,444,887 A | 4/1984 | Hoffmann |
| 4,716,111 A | 12/1987 | Osband et al. |
| 4,946,778 A | 8/1990 | Ladner et al. |
| 5,258,498 A | 11/1993 | Huston et al. |
| 5,413,923 A | 5/1995 | Kucherlapati et al. |
| 5,530,101 A | 6/1996 | Queen et al. |
| 5,545,806 A | 8/1996 | Lonberg et al. |
| 5,565,332 A | 10/1996 | Hoogenboom et al. |
| 5,569,825 A | 10/1996 | Lonberg et al. |
| 5,585,089 A | 12/1996 | Queen et al. |
| 5,625,126 A | 4/1997 | Lonberg et al. |
| 5,633,425 A | 5/1997 | Lonberg et al. |
| 5,661,016 A | 8/1997 | Lonberg et al. |
| 5,814,318 A | 9/1998 | Lonberg et al. |
| 5,939,589 A | 8/1999 | Kaibel et al. |
| 6,420,377 B1 | 7/2002 | Lee et al. |
| 6,537,988 B2 | 3/2003 | Lee |
| 2012/0171226 A1 | 7/2012 | Horwitz |
| 2016/0376375 A1 | 12/2016 | Dotti et al. |

FOREIGN PATENT DOCUMENTS

| | | | |
|---|---|---|---|
| EP | 0519596 A1 | 12/1992 | |
| EP | 0592106 A1 | 4/1994 | |
| WO | WO 2015/080981 A1 * | 6/2015 | ......... C07K 16/3076 |
| WO | 2016077638 A1 | 5/2016 | |
| WO | 2016164429 A1 | 10/2016 | |

OTHER PUBLICATIONS

Dai et al. (Chimeric Antigen Receptors Modified T-Cells for Cancer Therapy. J Natl Cancer Inst. Jan. 27, 2016;108(7):djv439) (Year: 2016).*
Ilieva et al. "Chondroitin Sulfate Proteoglycan 4 and Its Potential As an Antibody Immunotherapy Target across Different Tumor Types" Frontiers in Immunology, 8(1911):1-15 (2018).
International Search Report and the Written Opinion of the International Searching Authority corresponding to International Patent Application No. PCT/US2019/034027 (14 pages) (mailed Sep. 20, 2019).
Gonnet et al. "Exhaustive Matching of the Entire Protein Sequence Database" Science, 256(5062):1443-1445 (1992).
Huston et al. "Protein engineering of single-chain Fv analogs and fusion proteins" Methods in Enzymology, 203:46-52 (1991) (Abstract only).
International Preliminary Report on Patentability corresponding to International Patent Application No. PCT/US2019/034027 (9 pages) (dated Dec. 24, 2020).
Lonberg et al. "Human antibodies from transgenic mice" International Reviews of Immunology, 13:65-93 (1995) (Abstract only).
Pearson, William R. "Using the FASTA Program to Search Protein and DNA Sequence Databases" Methods in Molecular Biology, 24:307-331 (1994).

(Continued)

*Primary Examiner* — Daniel E Kolker
*Assistant Examiner* — Estella M. Gustilo
(74) *Attorney, Agent, or Firm* — Myers Bigel, P.A.

(57) ABSTRACT

The present invention provides a chimeric antigen receptor (CAR) that recognizes CSPG4 as well as methods of use in the treatment of diseases and disorders.

27 Claims, 15 Drawing Sheets
Specification includes a Sequence Listing.

(56) References Cited

OTHER PUBLICATIONS

Riechmann et al. "Reshaping human antibodies for therapy" Nature, 332:323-327 (1988).
Shu et al. "Secretion of a single-gene-encoded immunoglobulin from myeloma cells" Proceedings of the National Academy of Sciences USA, 90(17):7995-7999 (1993).
Skerra et al. "Assembly of a Functional Immunoglobulin Fv Fragment in *Escherichia coli*" Science, 240:1038-1041 (1988).
Beard et al. "Multiple chimeric antigen receptors successfully target chondroitin sulfate proteoglycan 4 in several different cancer histologies and cancer stem cells" Journal for ImmunoTherapy of Cancer, 2:25 (2014).
Extended European Search Report corresponding to European Patent Application No. 19819773.3 (13 pages) (dated Feb. 10, 2022).
Geldres et al. "T lymphocytes redirected against the chondroitin sulfate proteoglycan-4 control the growth of multiple solid tumors both in vitro and in vivo" Clinical Cancer Research, 20(4):962-971 (2013).
Neri et al. "Recombinant Anti-Human Melanoma Antibodies Are Versatile Molecules" Journal of Investigative Dermatology, 107:164-170 (1996).
Pellegatta et al. "Constitutive and TNFα-inducible expression of chondroitin sulfate proteoglycan 4 in glioblastoma and neurospheres: Implications for CAR-T cell therapy" Science Translational Medicine, 10:1-14 (2018).

\* cited by examiner

METHODS AND COMPOSITIONS FOR CHIMERIC ANTIGEN RECEPTOR TARGETING CANCER CELLS

STATEMENT OF PRIORITY

This application is a 35 U.S.C. § 371 national phase application of International Application Serial No. PCT/US2019/034027, filed May 24, 2019, which claims the benefit, under 35 U.S.C. § 119 (e), of U.S. Provisional Application Ser. No. 62/684,513, filed Jun. 13, 2018, the entire contents of each of which are incorporated by reference herein.

STATEMENT REGARDING ELECTRONIC FILING OF A SEQUENCE LISTING

A Sequence Listing in ASCII text format, submitted under 37 C.F.R. § 1.821, entitled 5470-837_07092024_ST25.txt, 19,011 bytes in size, generated on Jul. 9, 2024, and filed via EFS-Web, is provided in lieu of a paper copy. This Sequence Listing is incorporated by reference into the specification for its disclosures.

FIELD OF THE INVENTION

The present invention is directed to chimeric antigen receptor (CAR) compositions and methods of their use in cancer immunotherapy.

BACKGROUND OF THE INVENTION

Chondroitin sulphate peptidoglycan 4 (CSPG4) is a member of the CSPG family. The rat orthologue of CSPG4 is known as nerve/glial antigen 2 (NG2). CSPG4 and NG2 are highly conserved although it still remains to be conclusively determined whether human CSPG4 and rat NG2 share completely overlapping functions. CSPG4 is a unique PG complex consisting of a 250 kDa N-linked glycoprotein and a 450 kDa proteoglycan component. The two components were initially reported to be non-covalently associated. Subsequent studies have then convincingly shown that they are independently expressed on the membrane of malignant cells. CSPG4, like NG2, is a cell surface type I transmembrane protein in which three major structural domains can be identified: the extracellular (consisting of 3 subdomains), the transmembrane and the cytoplasmic C-terminal domains. As with other PGs, decoration of CSPG4 with chondroitin sulfate occurs in the Golgi compartment.

In mouse models, CSPG4/NG2 is expressed by several immature cells such as oligodendrocyte progenitor cells, chondroblasts, skeletal muscle myoblasts, vascular smooth muscle cells and brain capillary endothelial cells, while being down-regulated in most differentiated cells. During embryonic development, CSPG4/NG2 is expressed in the embryonic heart by day 9 and in the microvasculature of the central nervous system by day 12. While the expression pattern of CSPG4/NG2 may suggest a critical role in organogenesis, the knockout mouse $NG2^{-/-}$ does not show a specific phenotype as these mice are morphologically and functionally comparable to wild-type mice. CSPG4/NG2 is however involved in angiogenesis and wound repair. In mice NG2 is expressed by angiogenesis-associated pericytes in both normal and pathologic conditions. NG2 interacts with the galectin-3/α3β1 integrin complex expressed by endothelial cells. Activation of β1 integrin signaling promotes endothelial cell motility and endothelial tube formation in in vitro assays and blood vessel development in vivo. In addition, CSPG4 also associates with platelet-derived growth factor receptor (PDGFR)-α, integrins α3β1 and α4β1. STAT5A may be involved in regulating CSPG4 expression since there are potential binding sites of STAT5A located in CSPG4 promoter region.

Initial studies focused on the expression of CSPG4 by melanoma cells, since it was assumed that the expression of this tumor associated antigen (TAA) was restricted to this type of malignancy. Analysis of about 2000 surgically removed melanoma tumors showed that CSPG4 is expressed in more than 70% of melanoma lesions. In subsequent years flow cytometry analysis of established cancer cell lines and immunohistochemistry staining of surgically excised tumors from patients has shown that CSPG4 is expressed on several types of malignancies besides melanoma. They include glioblastoma, squamous cell carcinoma of the head and neck (SCCHN), TNBC, mesothelioma, renal cell carcinoma, chondrosarcoma, osteosarcoma, soft tissue sarcomas, and subsets of acute leukemia. In most malignancies CSPG4 has a high expression on malignant cells with limited intra- and inter-lesion heterogeneity. It is noteworthy that in various types of cancer such as SCCHN, TNBC and melanoma. CSPG4 has been shown to be expressed not only by differentiated malignant cells, but also by cancer initiating cells (CICs). However, this expression pattern is present in many types of cancers but does not appear to be a general phenomenon, since CSPG4 was not detected on CICs, identified on the basis of CD133 expression, in glioma tumors.

Several lines of experimental evidence indicate that even if CSPG4/NG2 is not an oncogene per se, it can be directly involved in melanoma progression by promoting tumor cell motility and metastasis. In particular, the cytoplasmic domains of NG2 contains multiple amino acid residues that can be phosphorylated and then promote sustained activation of survival and growth pathways such as the integrin-regulated focal adhesion kinase (FAK), ERK 1, 2, and PI3K/AKT pathways. This implicates CSPG4/NG2 as playing a crucial role in tumor progression by controlling cell adhesion processes, and may also accounts for the association between CSPG4 expression and poor clinical outcome as found in acral lentiginous melanoma, high grade glioma, HNSCC and breast cancer.

CSPG4 and its homologous NG2 have been targeted with monoclonal antibodies (mAbs) and T cell-based immunotherapy both in animal models and clinical settings. The malignancy that has been mostly targeted in these studies is malignant melanoma. In general, targeting CSPG4 has been found to be associated with a survival prolongation and only occasionally with a marked reduction of tumor volume. Both in animal models and patients induction of CSPG4-T cell and humoral immunity has not been associated with major toxicity.

CSPG4 and its homologs in other animal species are self-antigens and therefore are generally not immunogenic when expressed by tumor cells. Unresponsiveness to self-CSPG4 can be overcome by immunization with CSPG4 mimics. CSPG4 immune responses have been indeed elicited both in humans and dogs with melanoma and also in rat models. CSPG4 mimics were represented by anti-idiotype mAbs that bear the internal image of the nominal antigen in human subjects and in rats, and by DNA encoding the human CSPG4 in dogs. In the latter case the high degree of homology, but not complete identity between human CSPG4 and its dog counterpart, provides the DNA encoding human CSPG4 with the ability to overcome unresponsiveness to self-CSPG4 in xenogeneic hosts. The induced humoral immunity was associated with a survival prolongation. None of the described experiments formally proved a cause effect relationship between CSPG4-specific humoral immunity and clinical responses and also excludes a therapeutic role of T cell-mediated responses. Nevertheless the antitumor effects of the in vivo induced humoral responses is supported by the ability of CSPG4-specific Abs to inhibit tumor growth, and more importantly disease recurrence and metastatic spread in immunodeficient mice grafted with human melanoma, TNBC, mesothelioma cells and glioblastoma. In support of the critical tumorigenic role of CSPG4 signaling pathways, inhibition of CSPG4-related pathways and tumor regression can also be achieved by local delivery of shRNA as demonstrated by local injection of lentivirus carrying CSPG4-specific shRNA in melanoma models. This approach may become clinically applicable considering the possibility to use oncolytic viruses as a delivery system for shRNA infused either intratumoral or systemically. To further exploit the specificity of CSPG4-specific Abs, an anti-CSPG4 scFv Ab fragment was fused with human TNF-related apoptosis-inducing ligand (TRAIL) in an attempt to locally deliver a pro-apoptotic molecule to CSPG4 expressing tumors. Finally, the specificity of CSPG4 Abs has also been exploited to engage the cellular component of the immune system. A humanized bi-specific BiTE Ab (bi-specific T-cell engaging) that binds CSPG4 and CD3 molecules was created, and when T lymphocytes were co-cultured with melanoma cells in the presence of the specific BITE, CSPG4-expressing melanoma cells were lysed. Taking into consideration that a similar molecule has been recently approved by the FDA to treat CD19-expressing B cell malignancies, BITE-CSPG4-specific Abs will be tested in clinical trials.

While for many years T cell therapies were mostly based on the ex vivo expansion of tumor-specific T cell precursors circulating in the peripheral blood or isolated from tumor biopsies, most recent T cell therapies rely on an engineering process of circulating T lymphocytes. Polyclonal T cells are genetically modified using viral vectors to express either a HLA class I restricted T cell receptor (αβTCR) specific for TAA derived peptides or CARs.

In sharp contrast with αβTCRs, CARs are chimeric proteins in which the antigen-binding moieties of Abs are coupled with signaling molecules of T lymphocytes. In general, the variable regions of the heavy and light chains, in the form of a single-chain Ab, are joined with the intracellular signaling domains derived from the CD3ζ chain of the T-cell receptor, in tandem to costimulatory endodomains such as CD28, 4-1BB or OX40. When expressed by T lymphocytes these molecules redirect the antigen-specificity of engrafted T cells towards the Ab moiety, and promote the effector function and co-stimulation of T lymphocytes.

The different structures of αβTCRs and CARs lead to fundamental differences in antigen recognition of T cells engineered to express these molecules. αβTCR-T cell based strategies require that the TAA is processed by the HLA class I antigen processing machinery (APM), so that peptides are generated and presented by the restricting HLA class I allele to the cognate αβTCR. Specifically, peptides generated by the proteasome from mostly, although not exclusively, endogenous proteins are transported by the heterodimer transporter associated with antigen processing (TAP) to the endoplasmic reticulum. Here peptides are loaded on B2-microglobulin-associated HLA class I heavy chain dimers with the help of the chaperone molecules ERp57, calnexin, calreticulin and tapasin. The trimolecular complex then travels to the cell membrane where it is presented to the cognate αβTCR.

In sharp contrast to conventional αβTCR recognition, CAR-redirected T cells do not require any processing of the targeted TAA since the antigen-binding moiety is derived from Abs, but requires that TAAs be expressed on tumor cell membrane. The CAR-based strategy has several advantages over the αβTCR-based strategy. First, not being HLA class I restricted, CAR-T cell are applicable to all patients independently of their HLA type. Furthermore the recognition of targeted tumor cells by CAR-T cells does not require processing and presentation of the targeted TAA by the HLA class I APM. As a result, the anti-tumor activity of CAR-T cells is not affected by abnormalities in APM, which are frequently present in malignant cells, although with marked differences among various types of cancers. Through multiple mechanisms these abnormalities provide tumor cells with an escape from T cell recognition and destruction.

The present invention overcomes previous shortcomings in the art by providing a chimeric antigen receptor (CAR) that targets the chondroitin sulphate peptidoglycan 4 (CSPG4) cancer antigen and methods of its use in treating cancer.

SUMMARY OF THE INVENTION

The present invention provides methods and compositions for the treatment of cancer, including treatment of cancer employing immunotherapy. In particular cases, the immunotherapy includes T lymphocytes engineered to target certain cancers.

Thus, in one embodiment, the present invention provides a chimeric antigen receptor (CAR) comprising the amino acid sequences:

```
                                              (SEQ ID NO: 1)
QIQLVQSGPELKKPGETVKISCKASGYTFTDYSMHWVKKTPGKGLKWLG

WINTATGEPTYADDFKGRFAISLETSARTVYLQINNLRNEDTATYFCFS

YYDYWGQGTTLTVSS (UNC 763.74 Vh1)
``` and

```
                                              (SEQ ID NO: 2)
DILLTQSPAILSVTPGETVSLSCRASQTIYKNLHWYQQKSHRSPRLLIK

YGSDSISGIPSRFTGSGSGTDYTLNINSVKPEDEGIYYCLQGYSTPWTF

GGGTKLEIK(UNC 763.74 Vk2),
``` linked together in any orientation.

In an additional embodiment, the present invention provides a chimeric antigen receptor (CAR) comprising the amino acid sequences:

```
                                              (SEQ ID NO: 3)
KVKLQESGGGLVQPGGSMKLSCVVSGFTFSNYWMNWVRQSPEKGLEWIA

EIRLKSNNFARYYAESVKGRFTISRDDSKSSVYLQMINLRAEDTGIYYC

TSYGNYVGHYFDHWGQGTTLTVSS (225.28 Vh1)
``` and

```
                                              (SEQ ID NO: 4)
DIVMTQSQKFMSTSVGDRVSVTCKASQNVDTNVAWYQQKPGQSPEPLLF

SASYRYTGVPDRFTGSGSGTDFTLTISNVQSEDLAEYFCQQYNSYPLTF

GGGTKLVIK (225.28 Vk),
``` linked together in any orientation.

The present invention further provides a chimeric antigen receptor (CAR) comprising, consisting essentially of or consisting of the amino acid sequence:

```
                                              (SEQ ID NO: 5)
AM EFGL SWL FLV AILK GVQ CDI LLTQ SPA ILS VTPG

ETV SLS CRAS QTI YKN LHWY QQK SHR SPRL LIK YGS

DSIS GIP SRF TGSG SGT DYT LNIN SVK PED EGIY YCL
```

-continued

QGY STPW TFG GGT KLEI KGG GGS GGGG SGG GGQ IQLV
QSG PEL KKPG ETV KIS CKAS GYT FTD YSMH WVK KTP
GKGL KWL GWI NTAT GEP TYA DDFK GRF AIS LETS ART
VYL QINN LRN EDT ATYF CFS YYD YWGQ GTT LTV SSTR C
[UNC 763.74 scFv (Vk2. Vh1)].

Additionally provided herein is a chimeric antigen receptor comprising, consisting essentially of or consisting of the amino acid sequence:

(SEQ ID NO: 6)
AM EFGL SWL FLV AILK GVQ CQI QLVQ SGP ELK KPGE
TVK ISC KASG YTF TDY SMHW VKK TPG KGLK WLG WIN
TATG EPT YAD DFKG RFA ISL ETSA RTV YLQ INNL RNE
DTA TYFC FSY YDY WGQG TTL TVS SGGG GSG GGG SGGG
GDI LLT QSPA ILS VTP GETV SLS CRA SQTI YKN LHW
YQQK SHR SPR LLIK YGS DSI SGIP SRF TGS GSGT DYT
LNI NSVK PED EGI YYCL QGY STP WTFG GGT KLE IKTR
C [UNC763.74 scFv (Vh1. Vk2)].

Also provided herein is a chimeric antigen receptor comprising, consisting essentially of or consisting of the amino acid sequence:

(SEQ ID NO: 7)
AM EFGL SWL FLV AILK GVQ CKV KLQE SGG GLV QPGG
SMK LSC VVSG FTF SNY WMNW VRQ SPE KGLE WIA EIR
LKSN NFA RYY AESV KGR FTI SRDD SKS SVY LQMI NLR
AED TGIY YCT SYG NYVG HYF DHW GQGT TLT VSS GGGG
SGG GGS GGGG DIV MTQ SQKF MST SVG DRVS VTC KAS
QNVD TNV AWY QQKP GQS PEP LLFS ASY RYT GVPD RFT
GSG SGTD FTL TIS NVQS EDL AEY FCQQ YNS YPL TFGG
GTK LVI KTRC [225.28 scFv (Vh1.Vk)].

Further provided herein is a chimeric antigen receptor comprising, consisting essentially of or consisting of the amino acid sequence: AM EFGL SWL FLV AILK (SEQ ID NO: 8)
GVQ CDI VMTQ SQK FMS TSVG DRV SVT CKAS QNV DTN
VAWY QQK PGQ SPEP LLF SAS YRYT GVP DRF TGSG SGT
DFT LTIS NVQ SED LAEY FCQ QYN SYPL TFG GGT KLVI
KGG GGS GGGG SGG GGK VKLQ ESG GGL VQPG GSM KLS
CVVS GFT FSN YWMN WVR QSP EKGL EWI AEI RIKS NNF
ARY YAES VKG RFT ISRD DSK SSV YLQM INL RAE DTGI
YYC TSY GNYV GHY FDH WGQG TTL TVS STRC [225.28
scFv (Vk.Vh1)].

In a further embodiment, the present invention provides a nucleic acid molecule encoding the CAR of this invention.

The present invention further provides vectors and cells comprising the nucleic acid molecule of this invention.

In an additional embodiment, the present invention provides a nucleic acid molecule encoding a CAR of this invention, comprising, consisting essentially of or consisting of the nucleotide sequence:

(SEQ ID NO: 9)
TAGCCATGGAATTCGGCCTGAGCTGGCTGTTCCTGGTGGCCATCCTGAA

GGGCGTGCAGTGCGATATCCTGCTCACCCAGTCTCCAGCAATCCTGTCT

GTGACTCCAGGAGAAACAGTCAGTCTTTCCTGTAGGGCCAGCCAGACTA

TTTACAAGAACCTACACTGGTATCAACAGAAATCACATCGGTCTCCAAG

GCTTCTCATCAAGTATGGTTCTGATTCCATCTCTGGGATCCCCTCCAGG

TTCACTGGCAGTGGATCAGGGACAGATTACACTCTCAATATCAACAGTG

TGAAGCCCGAAGATGAAGGAATATATTACTGTCTTCAAGGTTACAGTAC

ACCTTGGACGTTCGGTGGAGGCACCAAGCTGGAAATCAAAGGTGGGGGC

GGTTCAGGCGGAGGTGGCTCTGGCGGTGGCGGACAGATCCAGTTGGTGC

AGTCTGGACCTGAGCTGAAGAAGCCTGGAGAGACAGTCAAGATCTCCTG

CAAGGCTTCTGGTTATACCTTCACAGACTATTCAATGCACTGGGTGAAG

AAGACTCCAGGAAAGGGTTTAAAGTGGCTGGGCTGGATAAACACTGCGA

CTGGTGAGCCAACATATGCAGATGACTTCAAGGGACGGTTTGCCATCTC

TTTGGAAACCTCTGCCAGGACTGTCTATTTGCAGATCAATAATCTCAGA

AATGAGGACACGGCTACATATTTCTGTTTTAGTTACTACGACTACTGGG

GCCAAGGCACCACTCTCACAGTTTCCTCAACGCGTTGC (scFv.763.74 VK2.VH1).

Also provided herein is nucleic acid molecule encoding a CAR of this invention, comprising, consisting essentially of or consisting of the nucleotide sequence:

(SEQ ID NO: 10)
TAGCCATGGAATTCGGCCTGAGCTGGCTGTTCCTGGTGGCCATCCTGAA

GGGCGTGCAGTGCCAGATCCAGTTGGTGCAGTCTGGACCTGAGCTGAAG

AAGCCTGGAGAGACAGTCAAGATCTCCTGCAAGGCTTCTGGTTATACCT

TCACAGACTATTCAATGCACTGGGTGAAGAAGACTCCAGGAAAGGGTTT

AAAGTGGCTGGGCTGGATAAACACTGCGACTGGTGAGCCAACATATGCA

GATGACTTCAAGGGACGGTTTGCCATCTCTTTGGAAACCTCTGCCAGGA

CTGTCTATTTGCAGATCAATAATCTCAGAAATGAGGACACGGCTACATA

TTTCTGTTTTAGTTACTACGACTACTGGGGCCAAGGCACCACTCTCACA

GTTTCCTCAGGTGGGGCGGTTCAGGCGGAGGTGGCTCTGGCGGTGGCG

GAGATATCCTGCTCACCCAGTCTCCAGCAATCCTGTCTGTGACTCCAGG

AGAAACAGTCAGTCTTTCCTGTAGGGCCAGCCAGACTATTTACAAGAAC

CTACACTGGTATCAACAGAAATCACATCGGTCTCCAAGGCTTCTCATCA

AGTATGGTTCTGATTCCATCTCTGGGATCCCCTCCAGGTTCACTGGCAG

TGGATCAGGGACAGATTACACTCTCAATATCAACAGTGTGAAGCCCGAA

-continued

GATGAAGGAATATATTACTGTCTTCAAGGTTACAGTACACCTTGGACGT

TCGGTGGAGGCACCAAGCTGGAAATCAAAACGCGTTGC (scFv.763.74 VH1.VK2).

Further provided herein is a nucleic acid molecule encoding a CAR of this invention, comprising, consisting essentially of or consisting of the nucleotide sequence:

(SEQ ID NO: 11)
TAGCCATGGAATTCGGCCTGAGCTGGCTGTTCCTGGTGGCCATCCTGAA

GGGCGTGCAGTGCAAGGTGAAGCTGCAGGAGTCTGGAGGAGGCTTGGTG

CAACCTGGAGGATCCATGAAACTCTCCTGTGTTGTCTCTGGATTCACTT

TCAGTAATTACTGGATGAACTGGGTCCGCCAGTCTCCAGAGAAGGGGCT

TGAGTGGATTGCAGAAATTAGATTGAAATCCAATAATTTTGCAAGATAT

TATGCGGAGTCTGTGAAAGGGAGGTTCACCATCTCAAGAGATGATTCCA

AAAGTAGTGTCTACCTGCAAATGATCAACCTAAGAGCTGAAGATACTGG

CATTTATTACTGTACCAGTTATGGTAACTACGTTGGGCACTATTTTGAC

CACTGGGGCCAAGGCACCACTCTCACAGTCTCCTCAGGTGGGGCGGTT

CAGGCGGAGGTGGCTCTGGCGGTGGCGGAGACATTGTGATGACCCAGTC

TCAAAAATTCATGTCCACATCAGTAGGAGACAGGGTCAGCGTCACCTGC

AAGGCCAGTCAGAATGTGGATACTAATGTAGCCTGGTATCAACAAAAAC

CAGGGCAATCTCCTGAACCACTGCTTTTCTCGGCATCCTACCGTTACAC

TGGAGTCCCTGATCGCTTCACAGGCAGTGGATCTGGGACAGATTTCACT

CTCACCATCAGCAATGTGCAGTCTGAAGACTTGGCAGAGTATTTCTGTC

AGCAATATAACAGCTATCCTCTGACGTTCGGTGGAGGCACCAAGCTGGT

GATCAAAACGCGTTGC (scFv225.28 VH1.VK).

In additional embodiments, the present invention provides a nucleic acid molecule encoding a CAR of this invention, comprising, consisting essentially of or consisting of the nucleotide sequence:

(SEQ ID NO: 12)
TAGCCATGGAATTCGGCCTGAGCTGGCTGTTCCTGGTGGCCATCCTGAA

GGGCGTGCAGTGCGACATTGTGATGACCCAGTCTCAAAAATTCATGTCC

ACATCAGTAGGAGACAGGGTCAGCGTCACCTGCAAGGCCAGTCAGAATG

TGGATACTAATGTAGCCTGGTATCAACAAAAACCAGGGCAATCTCCTGA

ACCACTGCTTTTCTCGGCATCCTACCGTTACACTGGAGTCCCTGATCGC

TTCACAGGCAGTGGATCTGGGACAGATTTCACTCTCACCATCAGCAATG

TGCAGTCTGAAGACTTGGCAGAGTATTTCTGTCAGCAATATAACAGCTA

TCCTCTGACGTTCGGTGGAGGCACCAAGCTGGTGATCAAAGGTGGGGGC

GGTTCAGGCGGAGGTGGCTCTGGCGGTGGCGGAAAGGTGAAGCTGCAGG

AGTCTGGAGGAGGCTTGGTGCAACCTGGAGGATCCATGAAACTCTCCTG

TGTTGTCTCTGGATTCACTTTCAGTAATTACTGGATGAACTGGGTCCGC

CAGTCTCCAGAGAAGGGGCTTGAGTGGATTGCAGAAATTAGATTGAAAT

CCAATAATTTTGCAAGATATTATGCGGAGTCTGTGAAAGGGAGGTTCAC

CATCTCAAGAGATGATTCCAAAAGTAGTGTCTACCTGCAAATGATCAAC

CTAAGAGCTGAAGATACTGGCATTTATTACTGTACCAGTTATGGTAACT

ACGTTGGGCACTATTTTGACCACTGGGGCCAAGGCACCACTCTCACAGT

CTCCTCAACGCGTTGC (scFv225.28 VK.VH1).

In a further embodiment, the present invention provides a method of stimulating a T cell-mediated immune response to a CSPG4 expressing target cell population or tissue in a subject, comprising administering to the subject an effective amount of the nucleic acid molecule, vector and/or cell of this invention, thereby stimulating a T cell-mediated immune response to the CSPG4 expressing target cell population or tissue in the subject.

In additional embodiments, the present invention provides a method of providing an anti-tumor immunity in a subject, comprising administering to the subject an effective amount of the nucleic acid molecule, vector, and/or the cell of this invention, thereby providing an anti-tumor immunity in the subject.

The present invention further provides a method of treating a subject having a disease or disorder associated with elevated expression of CSPG4 by a cell of the subject, comprising administering to the subject an effective amount of the nucleic acid molecule, vector, and/or cell of this invention, thereby treating the subject having the disease or disorder associated with elevated expression of CSPG4 by the cell of the subject.

In an additional embodiment, the present invention provides a method of generating a persisting population of genetically engineered T cells in a subject (e.g., a subject diagnosed with cancer), comprising administering to the subject a T cell genetically engineered to express the CAR of this invention, wherein the persisting population of genetically engineered T cells persists in the subject following administration.

In a further embodiment, the present invention provides a method of expanding a population of genetically engineered T cells in a subject (e.g., a subject diagnosed with cancer), comprising administering to the subject a T cell genetically engineered to express a CAR of this invention, wherein the administered genetically engineered T cell produces a population of progeny T cells in the subject.

In an additional embodiment, the present invention provides a method of treating cancer in a subject, comprising administering to the subject an effective amount of the nucleic acid molecule, vector and/or the cell of this invention, thereby treating cancer in the subject.

The present invention also provides a method of targeting a cancer cell and/or a cancer initiating cell (CIC) having a CSPG4 antigen, comprising contacting the cancer cell and/or the CIC with a cell comprising the CAR of this invention.

Also provided herein is a method of detecting cancer cells and/or cancer initiating cells (CICs) in a cell sample, comprising: a) contacting the cell sample with the CAR of this invention under conditions whereby a binding complex can form; and b) detecting formation of the binding complex, wherein detection of the binding complex is indicative of cancer cells and/or CICs in the cell sample.

Another embodiment of this invention is a method of detecting cancer cells and/or cancer initiating cells (CICs) in a subject, comprising: a) contacting a cell sample obtained from the subject with the CAR of this invention under conditions whereby a binding complex can form; and b) detecting formation of the binding complex, wherein detection of the binding complex is indicative of the presence of cancer cells and/or CICs in the subject.

Further embodiments of the invention provide related nucleic acid molecules, recombinant expression vectors, host cells, populations of cells, antibodies or antigen binding portions thereof, antibody fragments and pharmaceutical compositions relating to the CARs of the invention.

BRIEF DESCRIPTION OF THE DRAWINGS

FIG. 1A) Example of the flow cytometry analysis of a coculture; FIG. 1B) Percentages of tumor cells, summary of 3 donors. These data illustrate that T cells expressing the CSPG4.CAR constructed with the 763.74 scFv do not completely eliminate target tumor cells in vitro.

FIG. 2A) Example of the flow cytometry analysis; FIG. 2B) Percentages of tumor cells left after coculture, summary of 3 donors. These data illustrate that T cells expressing the CSPG4.CAR constructed with the 763 UNC scFv either VH1-VK2 or VK2-VH1 completely eliminate target tumor cells in vitro.

FIG. 3A) IFN-gamma production by CAR-T cells; FIG. 3B) Il-2 production by CAR-T cells. These data illustrate that T cells expressing the CSPG4.CAR constructed with the 763 UNC scFv either VH1-VK2 or VK2-VH1 produce IFN-gamma and IL2 only in response to CSPG4+ tumor cells (Sk Mel2 and WM115) and not to CSPG4-tumor cells (M14).

FIG. 4A) Naming schema for previously used and new scFv225 sequences; all constructs include the CD28 endodomain linked to the CD3z endodomain. FIG. 4B) Representative flow plots of anti-scFv225 staining; the left panel represents old and new 469 [VH-VL] constructs, the right represents old and new 470 [VL-VH] constructs. % transduced was determined by gating above the non-transduced (NT) cell population. FIG. 4C) Summary data from 5 T cell donors. These data illustrate that T cells express all CSPG4.CAR constructed with the scFv 255 (469 old. 470 old. 469 new and 470 new).

FIG. 5A) Tumor cell counts at day 4 calculated using Invitrogen CountBright beads. FIG. 5B) Percentages of tumor cells after gating on live cells (assessed by viability dye). These data illustrate that T cells expressing the all CSPG4.CAR constructed with the scFv 255 (469 old. 470) old. 469 new and 470 new) are equally effective in eliminating CSPG4+ tumor cells (U138MG).

FIG. 6A) Tumor cell counts at day 4 calculated using Invitrogen CountBright beads. FIG. 6B) Percentages of tumor cells after gating on live cells (assessed by viability dye). These data illustrate that T cells expressing the all CSPG4.CAR constructed with the scFv 255 (469 old. 470) old. 469 new and 470 new) are equally effective in eliminating CSPG4+ tumor cells (U87).

FIG. 7A) Tumor cell counts at day 5 calculated using Invitrogen CountBright beads. FIG. 7B) Percentages of tumor cells after gating on live cells (assessed by viability dye). These data illustrate that T cells expressing the all CSPG4.CAR constructed with the scFv 255 (469 old. 470) old. 469 new and 470 new) are equally effective in eliminating CSPG4+ tumor cells (SKmel2).

FIG. 8A) Tumor cell counts at day 5 calculated using Invitrogen CountBright beads. FIG. 8B) Percentages of tumor cells after gating on live cells (assessed by viability dye). These data illustrate that T cells expressing the all CSPG4.CAR constructed with the scFv 255 (469 old. 470) old. 469 new and 470 new) are equally effective in eliminating CSPG4+ tumor cells (WM115).

DETAILED DESCRIPTION OF THE INVENTION

Figure 1A:
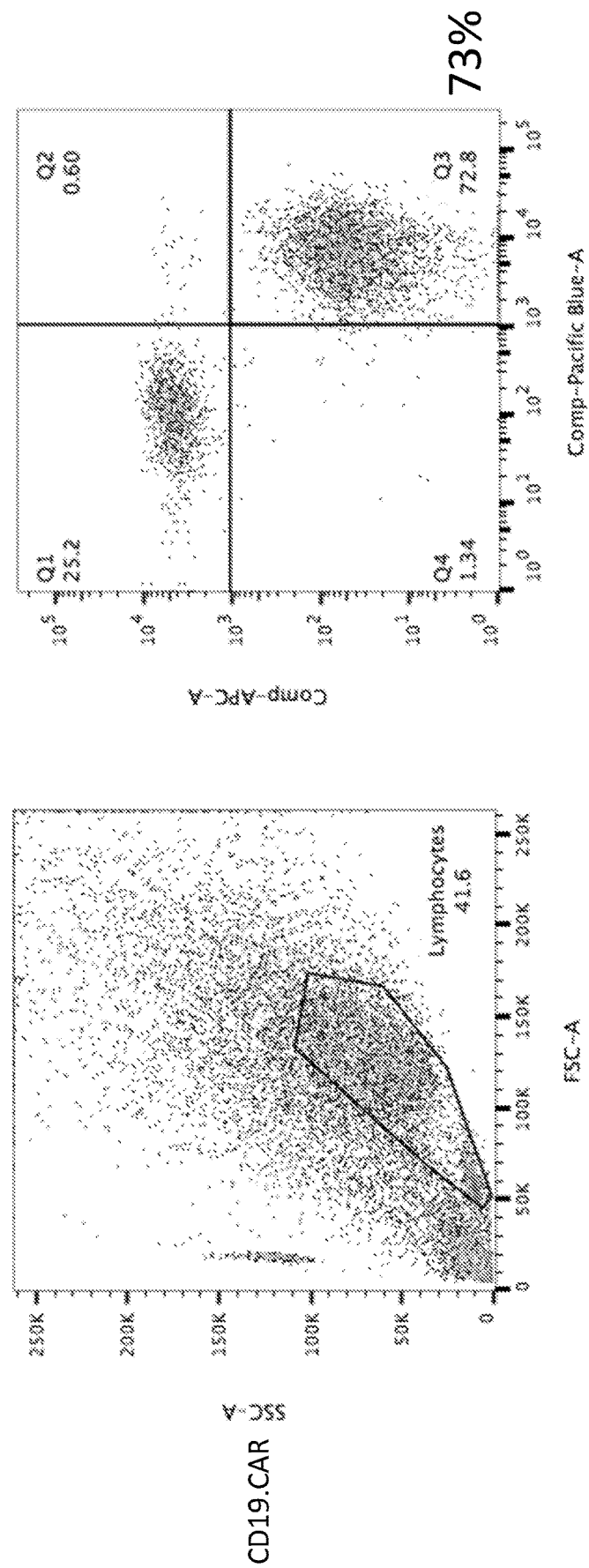
FIGS. 1A-1B. Coculture experiments with CSPG4+ human melanoma cell lines WM115 and Sk Mel 2. On day 0, tumor cells were collected with trypsin and plated in 24 well plates at 2.5×10$^5$ cells/well. The cells were given at least 6 hours to recover and adhere to the plate before the addition of T cells. The effector:target (E:T) ratio for this experiment was 1:1 by cell count, and the transduction efficiency was similar between the CSPG4.CAR constructs. On day 5, cocultures were collected using trypsin and stained for flow cytometry with CD3-APC and B7-H3-BV421 mAbs. Immediately before analysis by flow cytometer, samples were filtered and Invitrogen CountBright beads were added (25 ul/sample) to determine the percent of tumor cell population.
Figure 1A:
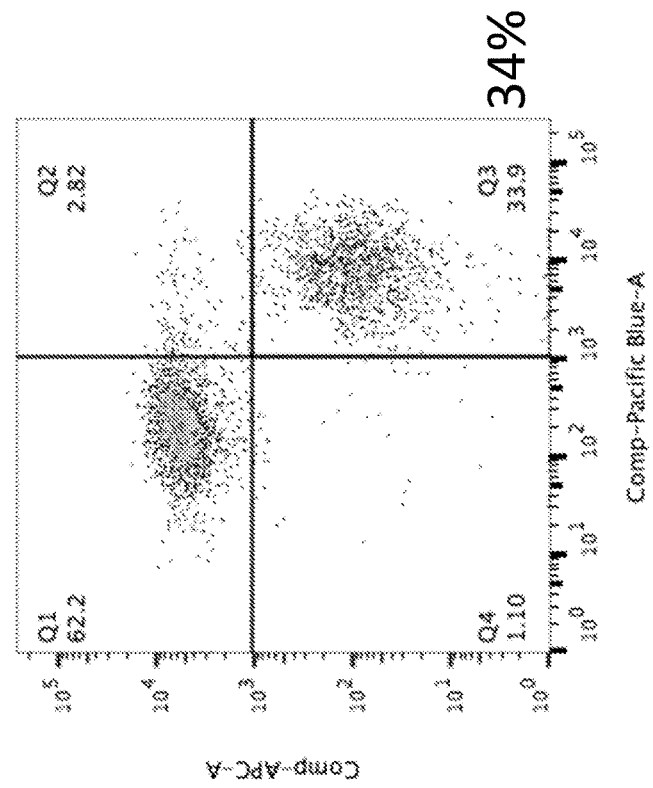
Figure 1A:
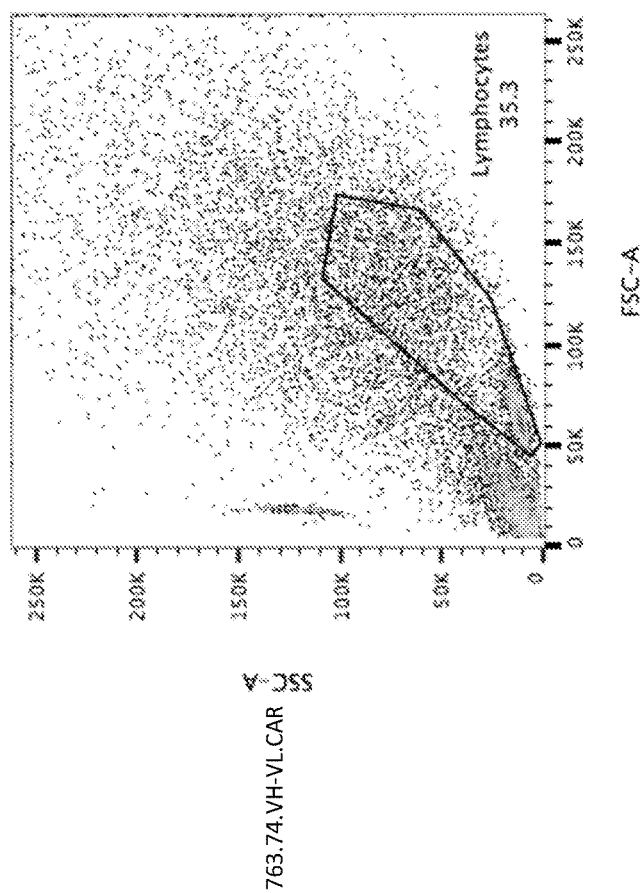
Figure 1A:
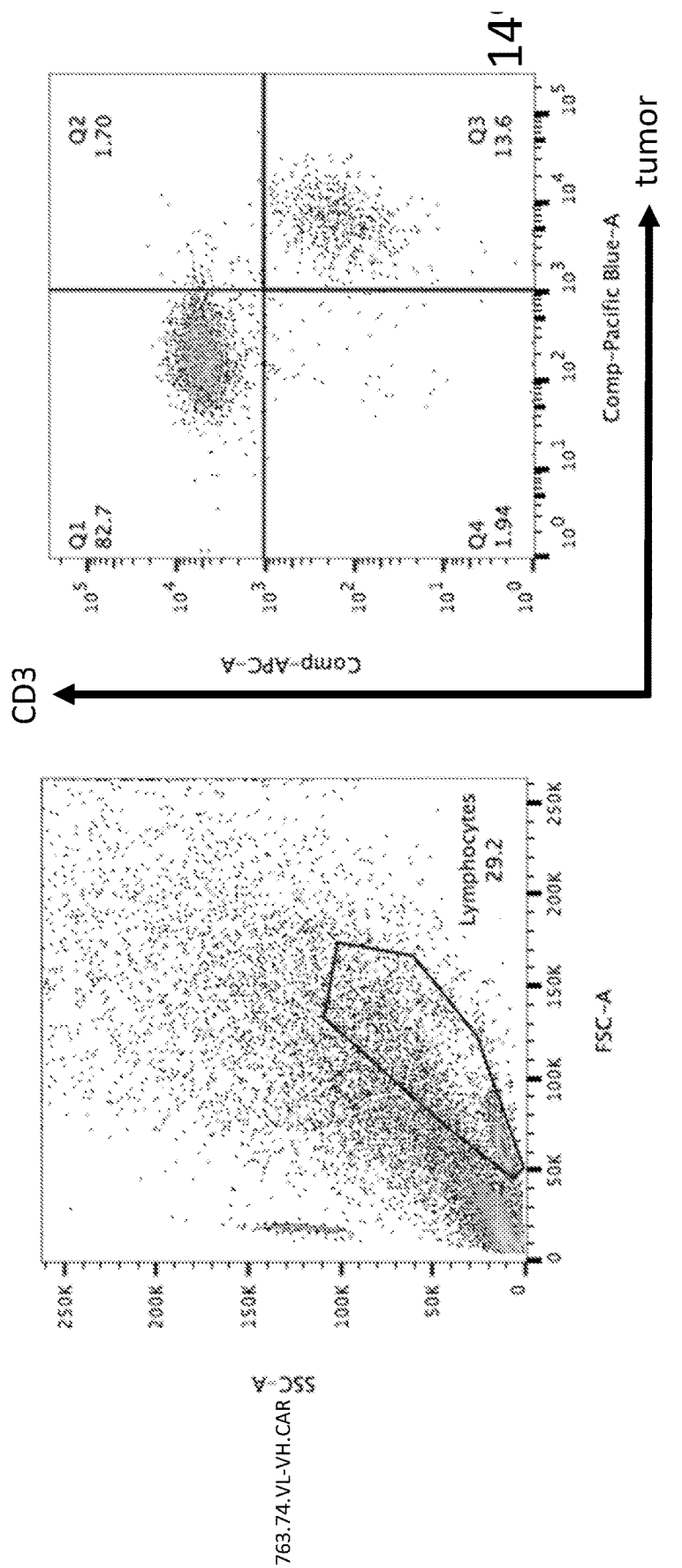
Figure 1B:
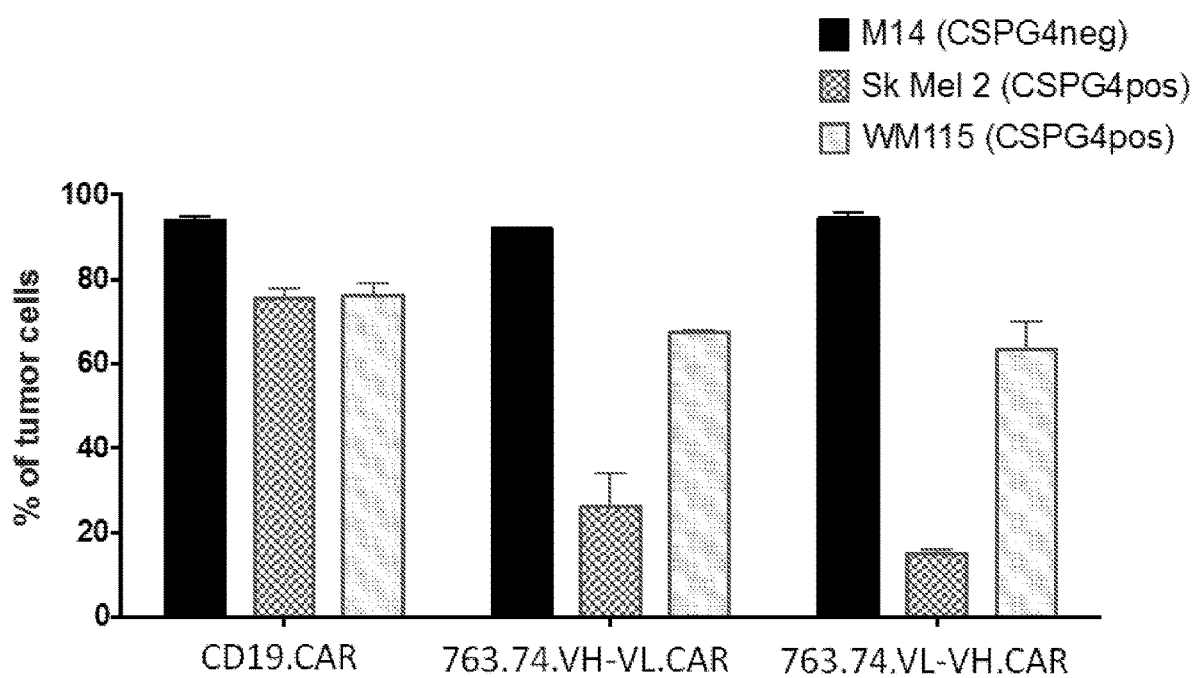
Figure 2A:
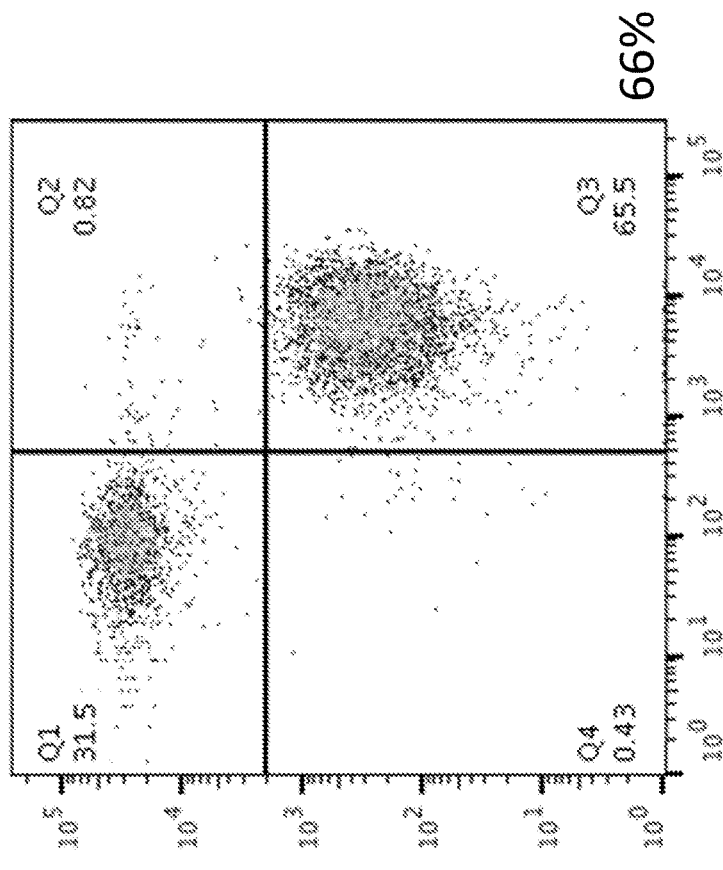
FIGS. 2A-2B. Coculture experiment with CSPG4+ human melanoma cell lines WM115 and Sk Mel 2. On day 0), tumor cells were collected with trypsin and plated in 24 well plates at 2.50×10$^5$ cells/well. Cells were given at least 6 hours to recover and adhere to the plate before the addition of T cells. The effector:target (E:T) ratio for this experiment were 1:1 and 1:5 by cell count, and the transduction efficiency was similar between the CSPG4.CAR constructs. On day 5, cocultures were collected using trypsin and stained for flow cytometry with CD3-APC and B7-H3-BV421 mAbs. Immediately before analysis by flow cytometer, samples were filtered and Invitrogen CountBright beads were added (25 ul/sample) to determine the percent of tumor cell population.
Figure 2A:
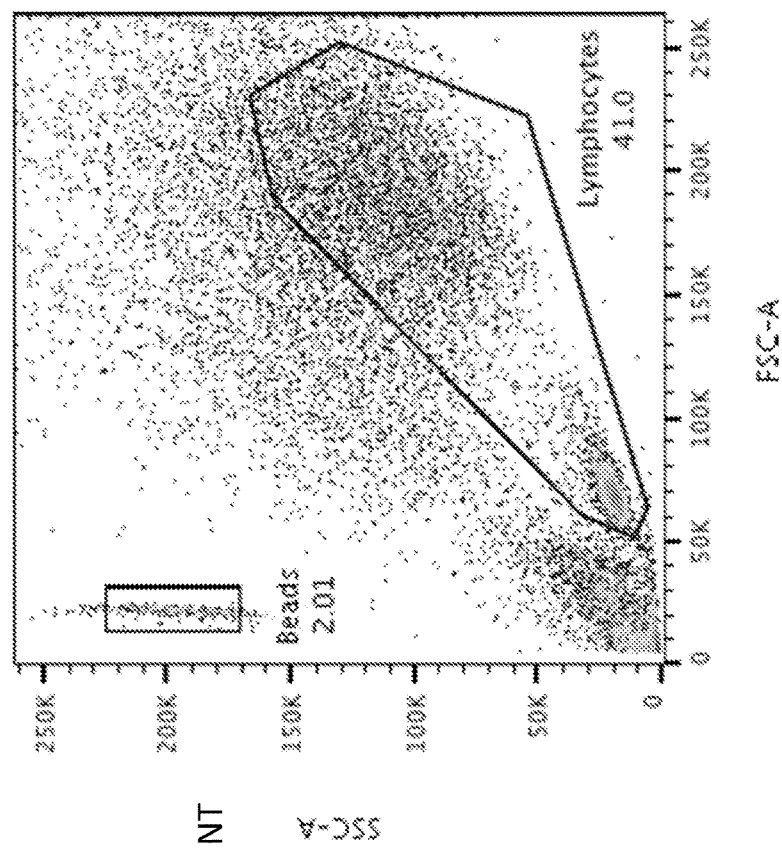
Figure 2A:
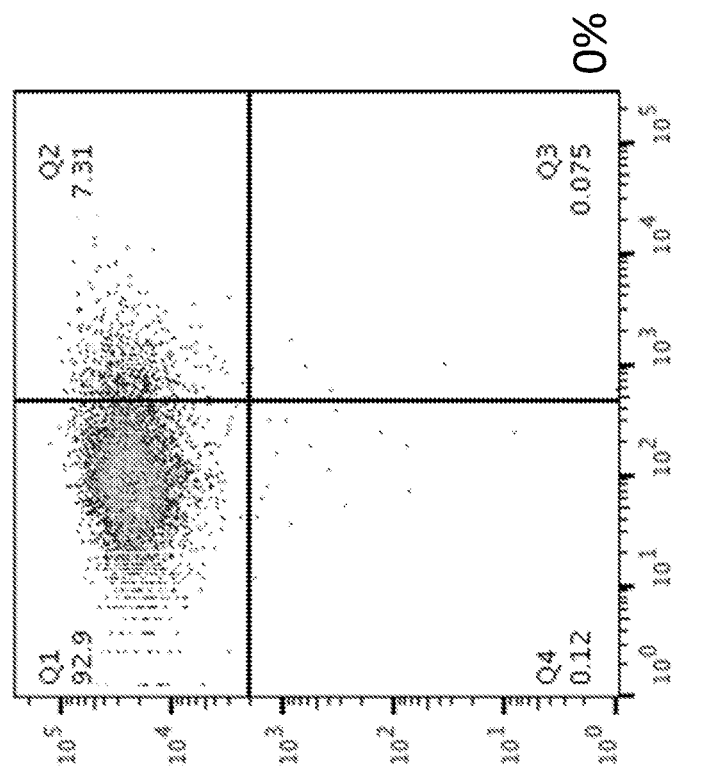
Figure 2A:
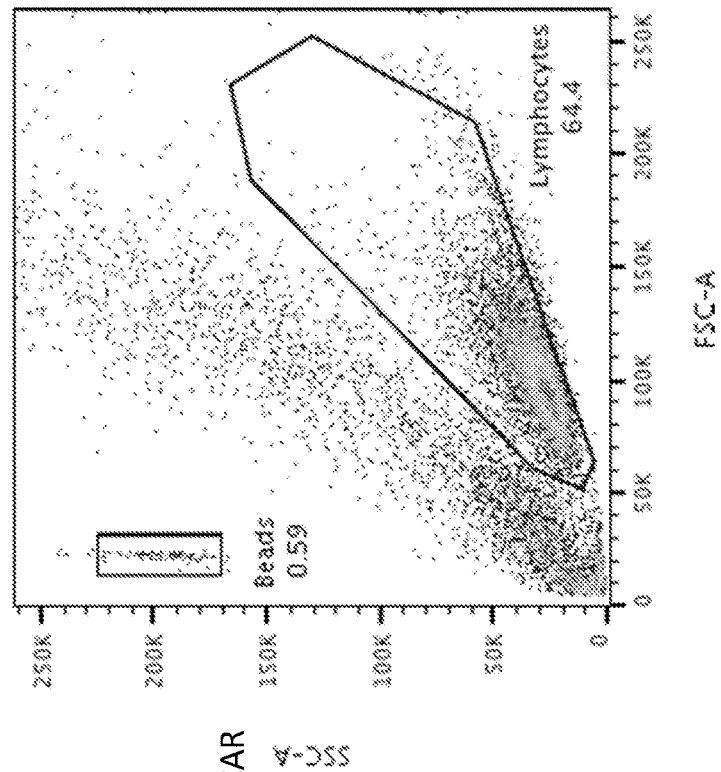
Figure 2A:
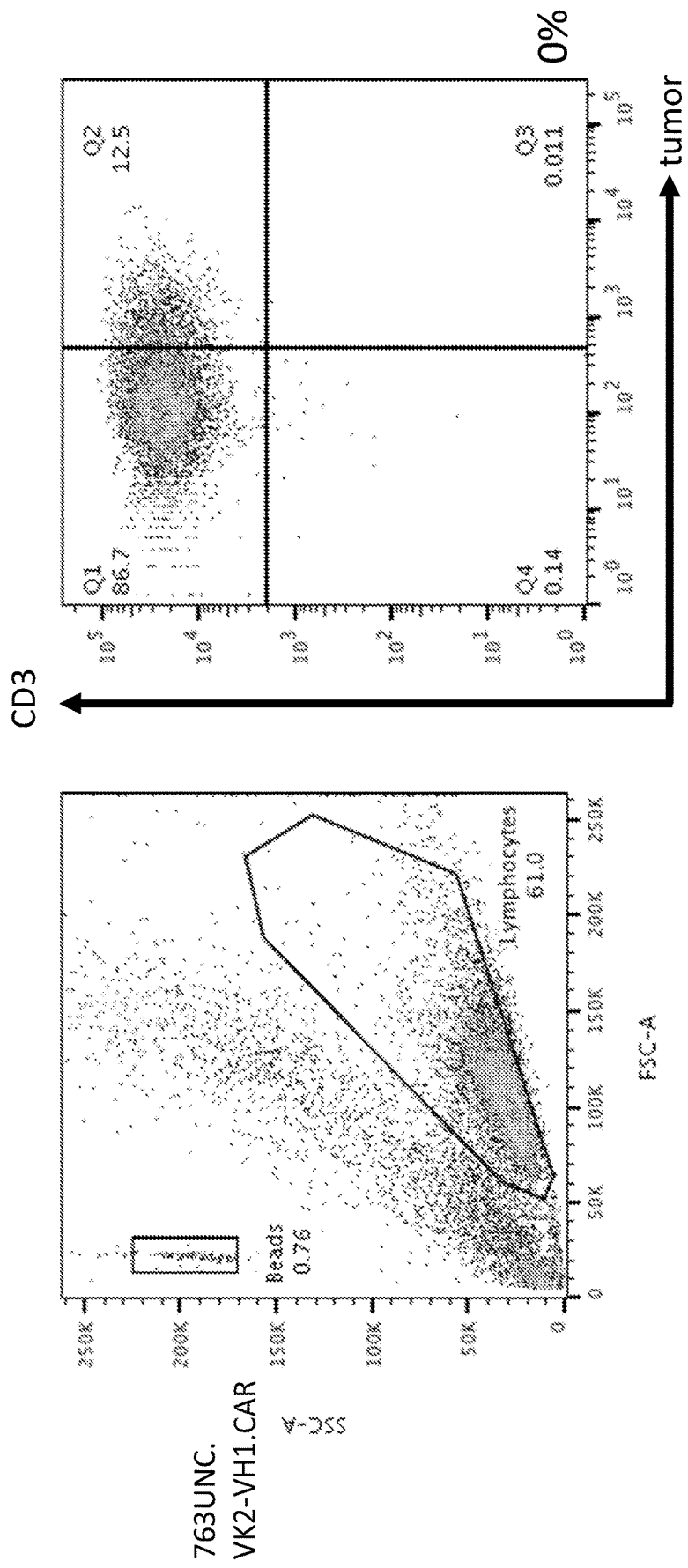
Figure 2B:
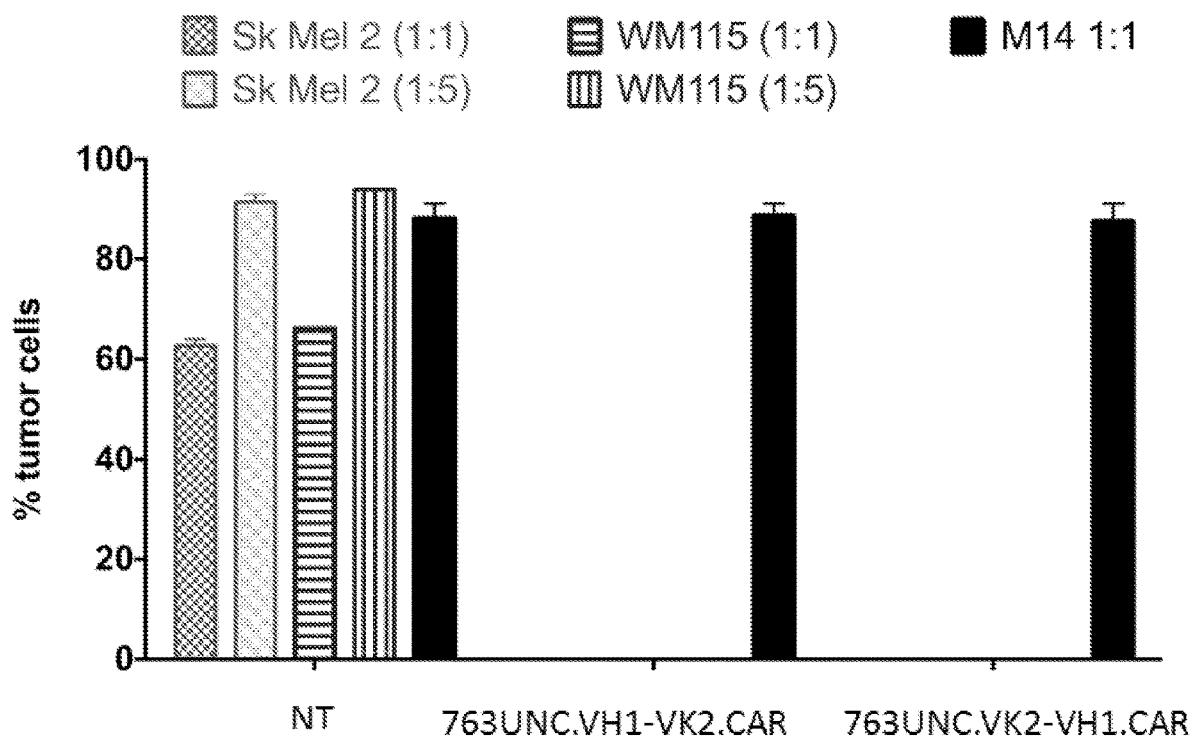
Figure 3A:
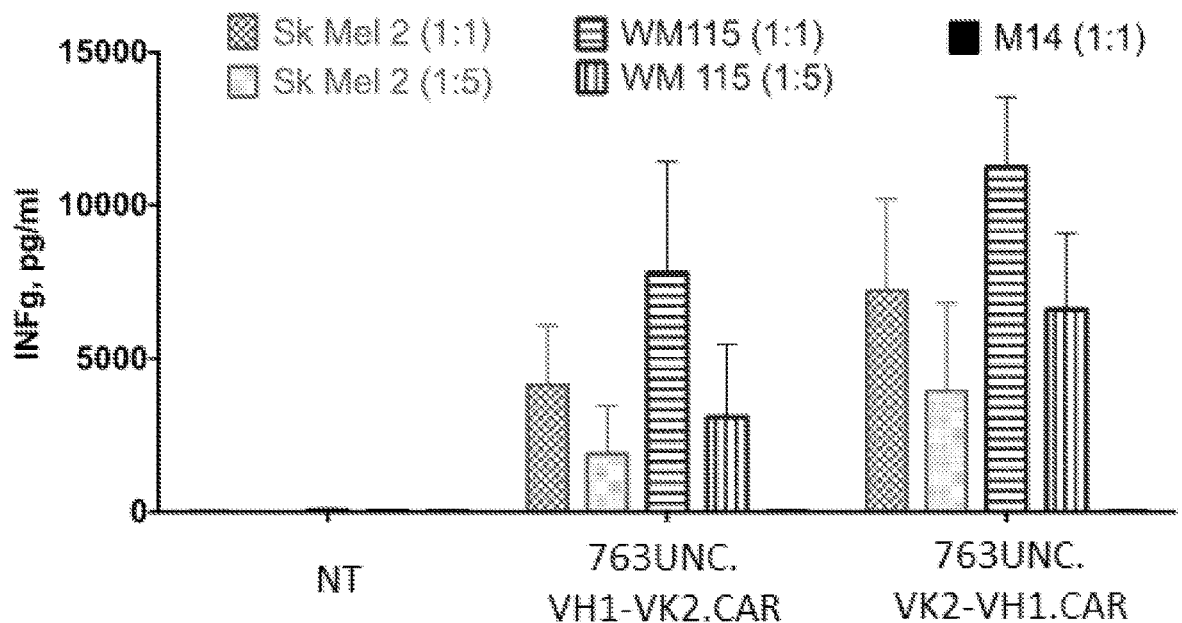
FIGS. 3A-3B. Production of cytokines by 763UNC CAR-T cells after 24 hrs of coculture with CSPG4+ human melanoma cell lines WM115 and Sk mel 2. The aliquots of growth media from a coculture of each cell line were analyzed by ELISA for the presence of IFN-gamma and interleukin-2 (IL-2) cytokines that manifest the antigen-driven proliferation of CAR-T cells Data plots show summaries for 3 donors.
Figure 3B:
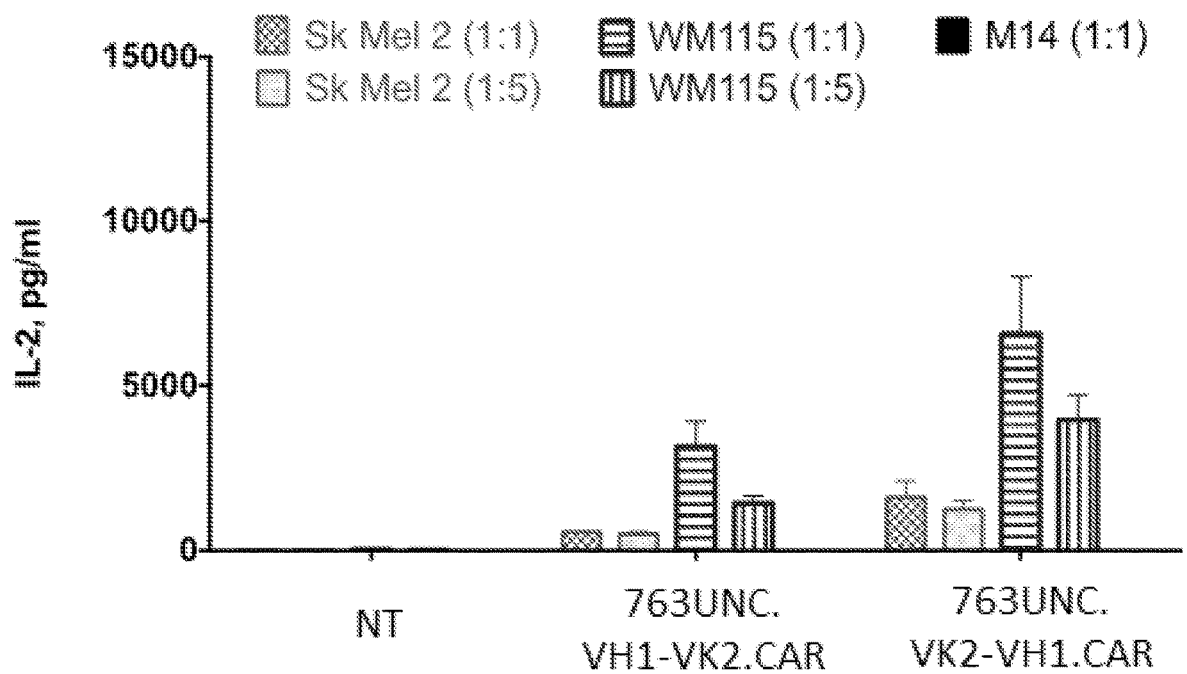
Figures 4A, 4B:
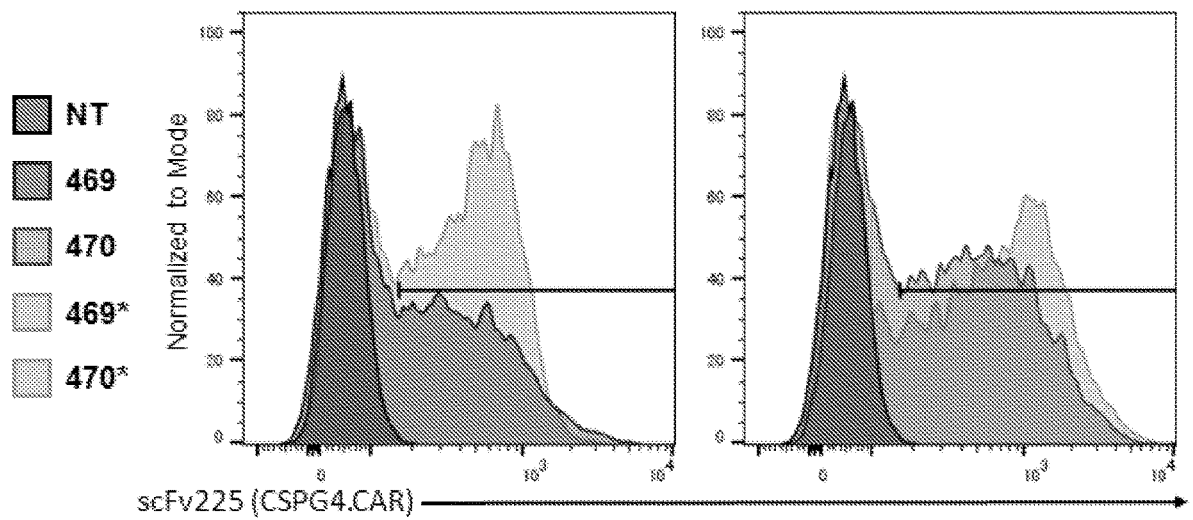
FIGS. 4A-4C. Retroviral transduction efficiency of scFv225 CAR.CD28z constructs. Five days after T cells were transduced with replication-deficient human retrovirus encoding for the scFv225 CSPG4.CAR constructs, the transduction efficiency was assessed. Samples were first incubated with a murine IgG1 anti-scFv225 specific antibody for 30 minutes at 25° C. washed with PBS, and subsequently stained with a rat anti-mouse IgG1 PE-conjugated antibody (clone X56, BD Biosciences) for 20 minutes at 4° C. After a final wash with PBS. T cells were analyzed for transduction by flow cytometry.
Figure 4C:
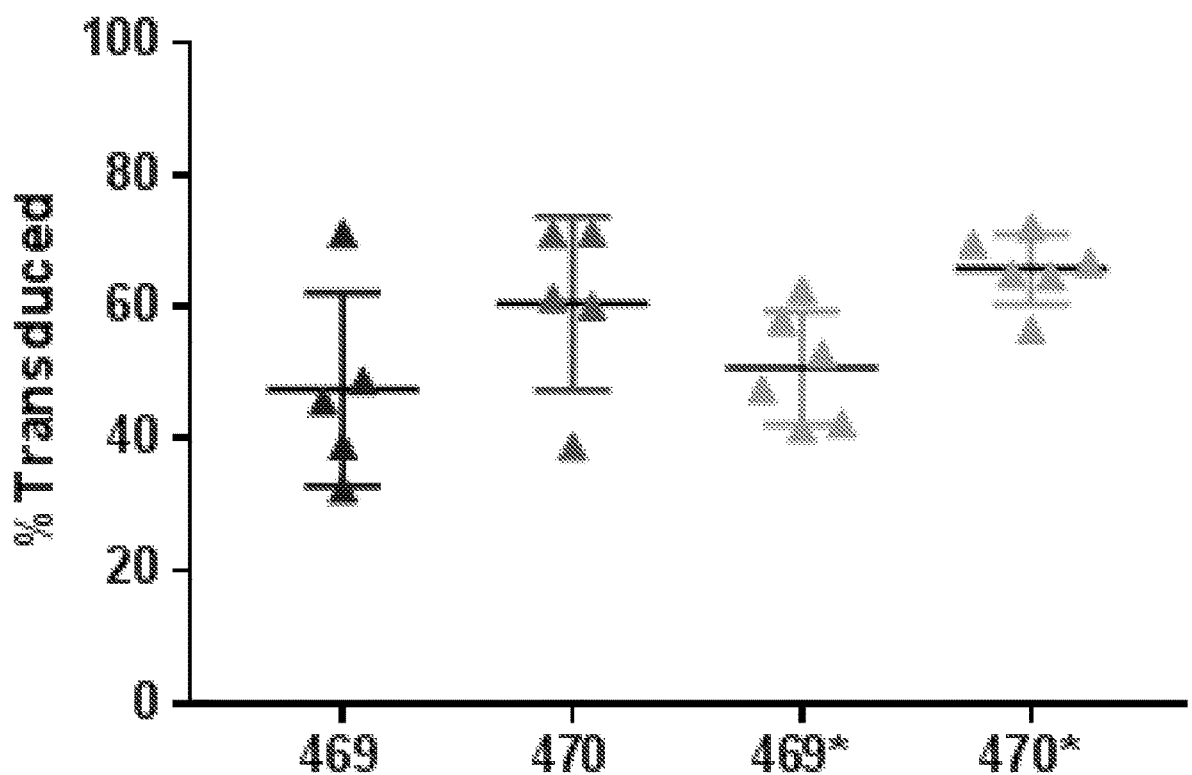
Figure 5A:
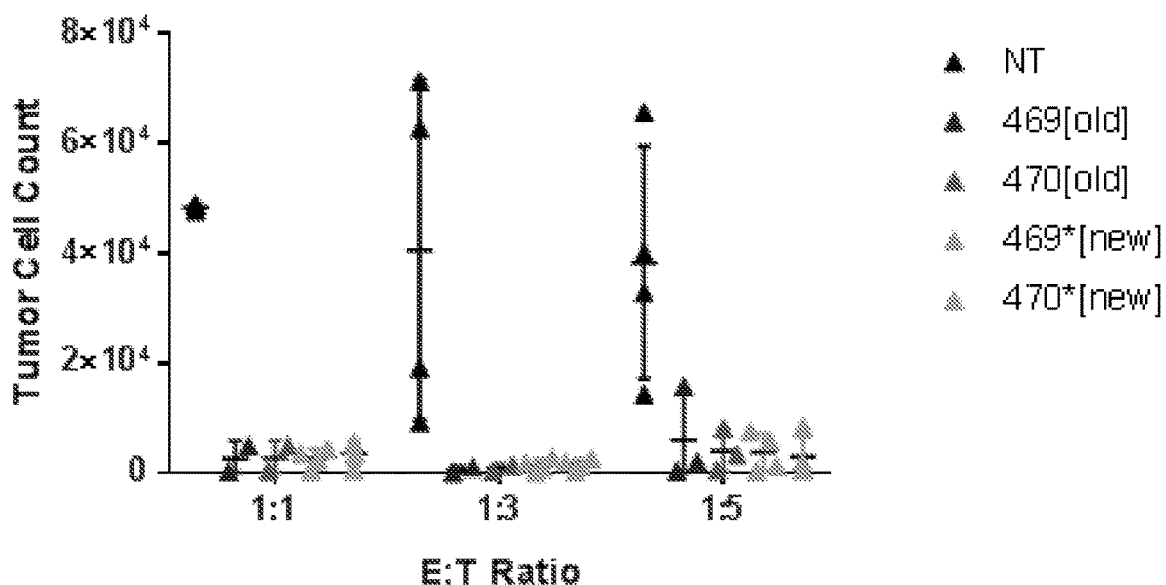
FIGS. 5A-5B. Results of 4 day coculture experiment with CSPG4+ human glioblastoma cell line U138MG. On day 0), tumor cells were collected with PBS/EDTA and plated in 24 well plates at 100,000 cells/well. Cells were given at least 4 hours to recover and adhere to the plate before the addition of T cells. The number of T cells plated was normalized for the transduction efficiency of each construct, and NT cells were added to equalize the total number of T cells in each well. The effector:target (E:T) ratio labeled in panels A and B reflects the number of CAR-T cells. On day 4, cocultures were collected using PBS/EDTA and stained for flow cytometry with CD3-APC. B7H3-BV421, and the viability dye ZombieAqua. Immediately before analysis by the flow cytometer, the samples were filtered and Invitrogen CountBright beads were added (25 ul/sample) to determine absolute cell counts.
Figure 5B:
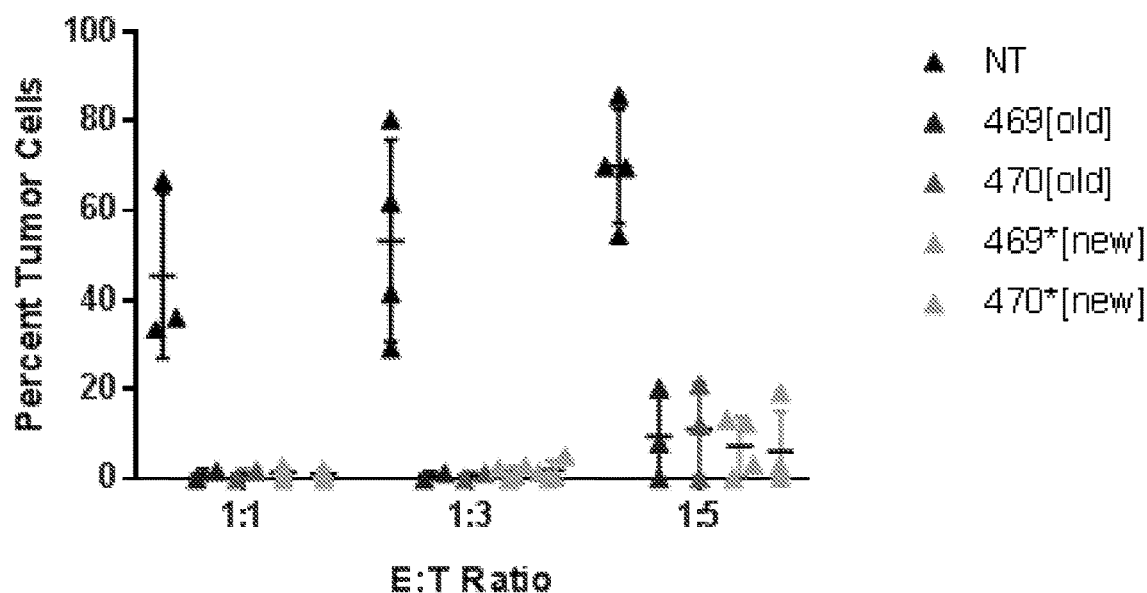
Figure 6A:
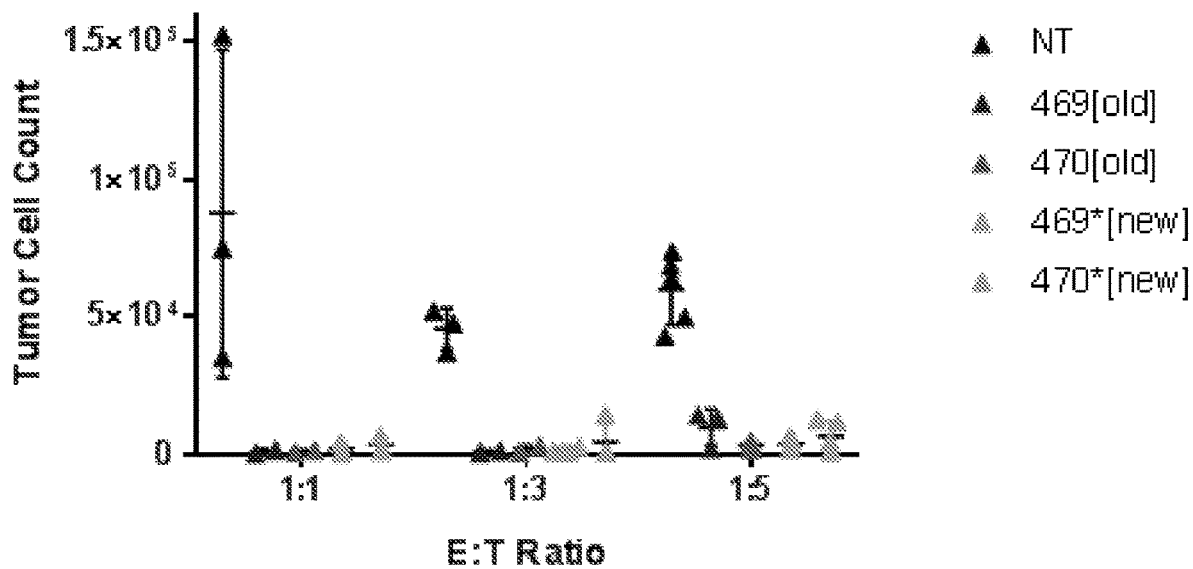
FIGS. 6A-6B. Results of 4 day coculture experiment with CSPG4+ human glioblastoma cell line U87. On day 0, tumor cells were collected with PBS/EDTA and plated in 24 well plates at 100,000 cells/well. Cells were given at least 4 hours to recover and adhere to the plate before the addition of T cells. The number of T cells plated was normalized for the transduction efficiency of each construct, and NT cells were added to equalize the total number of T cells in each well. The effector:target (E:T) ratio labeled in panels A and B reflects the number of CAR-T cells. On day 4, cocultures were collected using PBS/EDTA and stained for flow cytometry with CD3-APC. B7H3-BV421, and the viability dye ZombieAqua. Immediately before analysis by the flow cytometer, the samples were filtered and Invitrogen CountBright beads were added (25 ul/sample) to determine absolute cell counts.
Figure 6B:
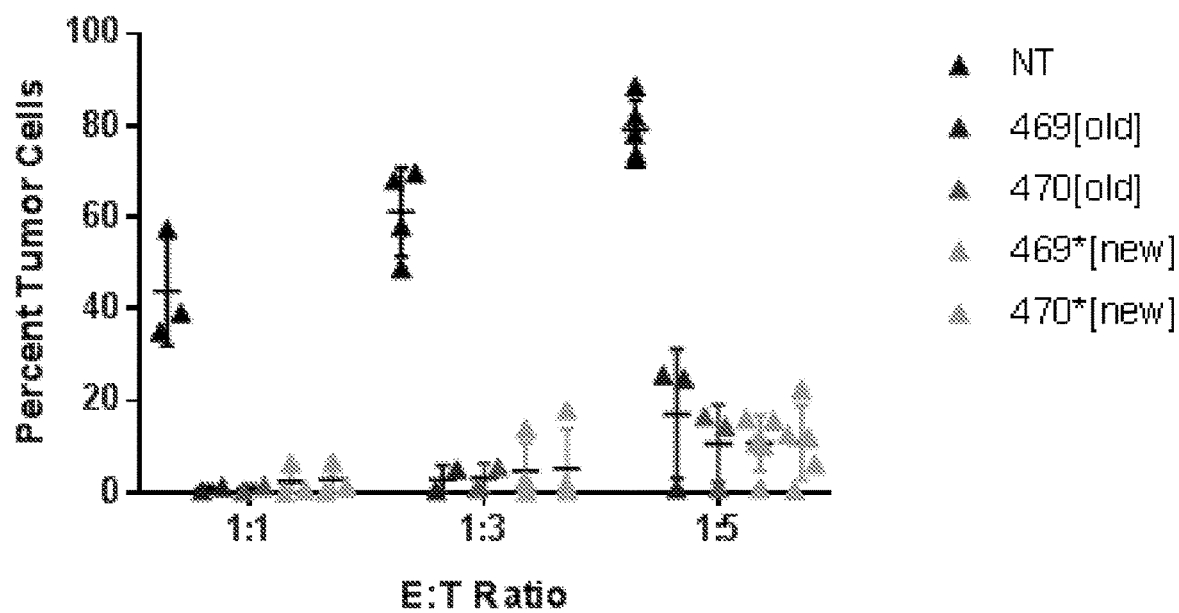
Figure 7A:
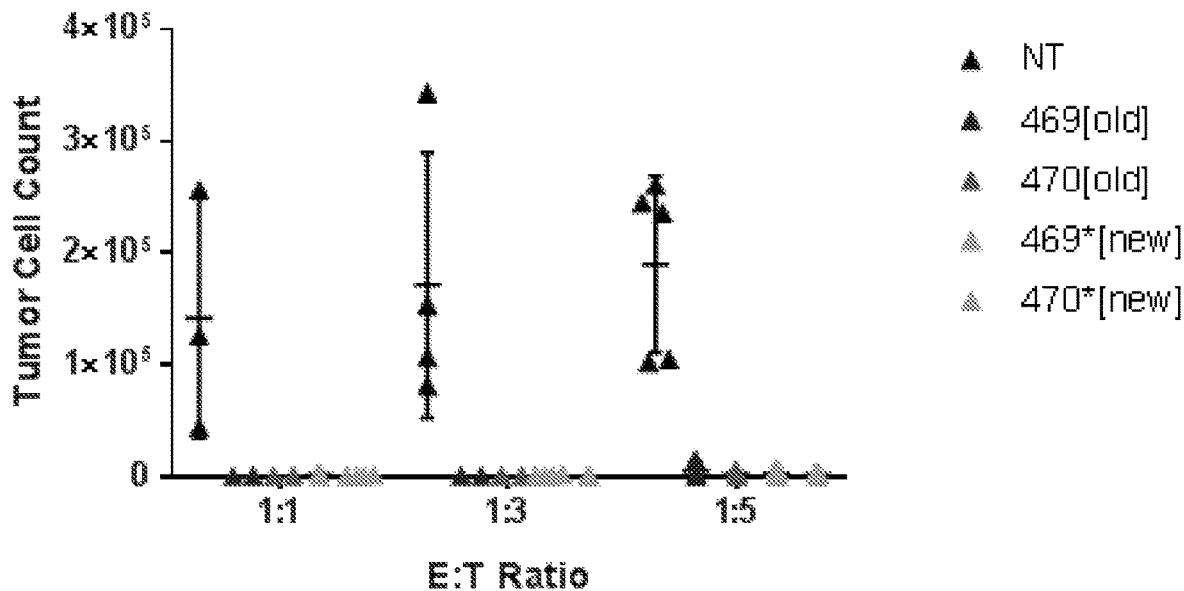
FIGS. 7A-7B. Results of 5 day coculture experiment with CSPG4+ human melanoma cell line SKmel2. On day 0, tumor cells were collected with PBS/EDTA and plated in 24 well plates at 100,000 cells/well. Cells were given at least 4 hours to recover and adhere to the plate before the addition of T cells. The number of T cells plated was normalized for the transduction efficiency of each construct, and NT cells were added to equalize the total number of T cells in each well. The effector:target (E:T) ratio labeled in panels A and B reflects the number of CAR-T cells. On day 5, cocultures were collected using PBS/EDTA and stained for flow cytometry with CD3-APC. B7H3-BV421, and the viability dye ZombieAqua. Immediately before analysis by the flow cytometer, the samples were filtered and Invitrogen CountBright beads were added (25 ul/sample) to determine absolute cell counts.
Figure 7B:
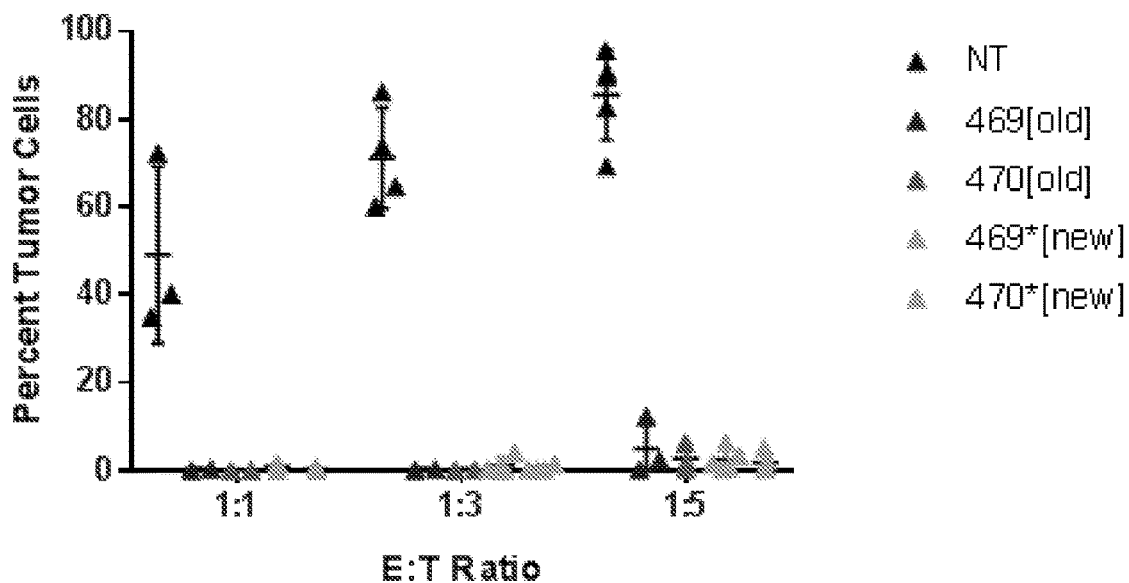
Figure 8A:
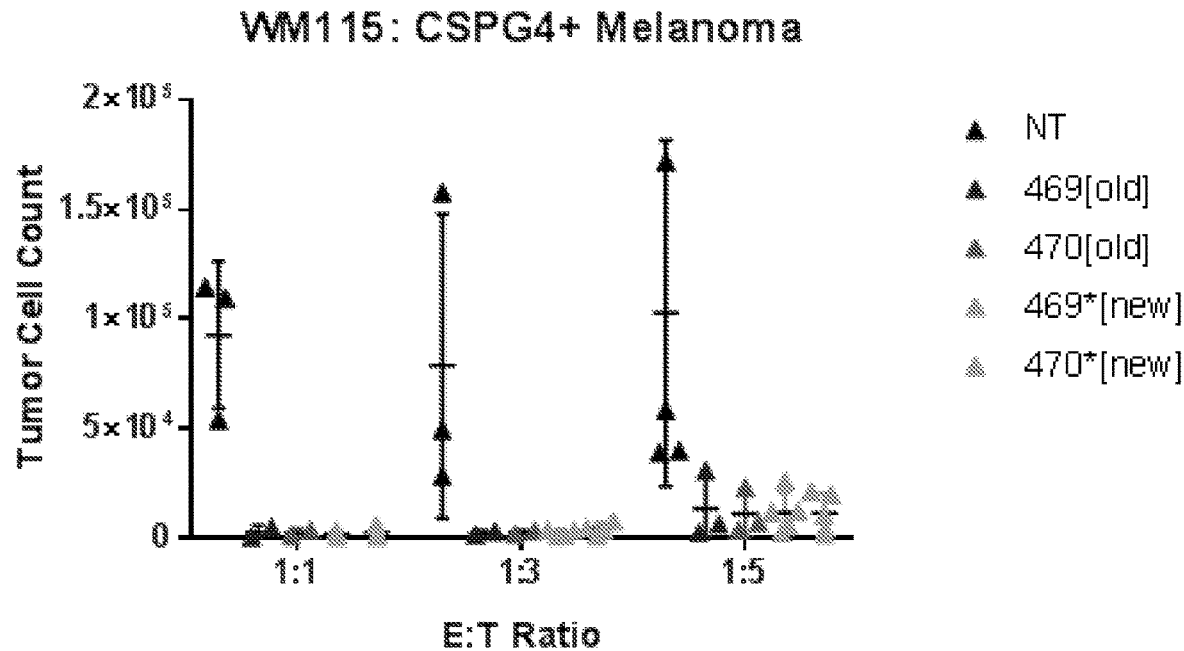
FIGS. 8A-8B. Results of 5 day coculture experiment with CSPG4+ human melanoma cell line WM115. On day 0), tumor cells were collected with PBS/EDTA and plated in 24 well plates at 100,000 cells/well. The cells were given at least 4 hours to recover and adhere to the plate before the addition of T cells. The number of T cells plated was normalized for the transduction efficiency of each construct, and NT cells were added to equalize the total number of T cells in each well. The effector:target (E:T) ratio labeled in panels A and B reflects the number of CAR-T cells. On day 5, cocultures were collected using PBS/EDTA and stained for flow cytometry with CD3-APC. B7H3-BV421, and the viability dye ZombieAqua. Immediately before analysis by the flow cytometer, the samples were filtered and Invitrogen CountBright beads were added (25 ul/sample) to determine absolute cell counts.
Figure 8B:
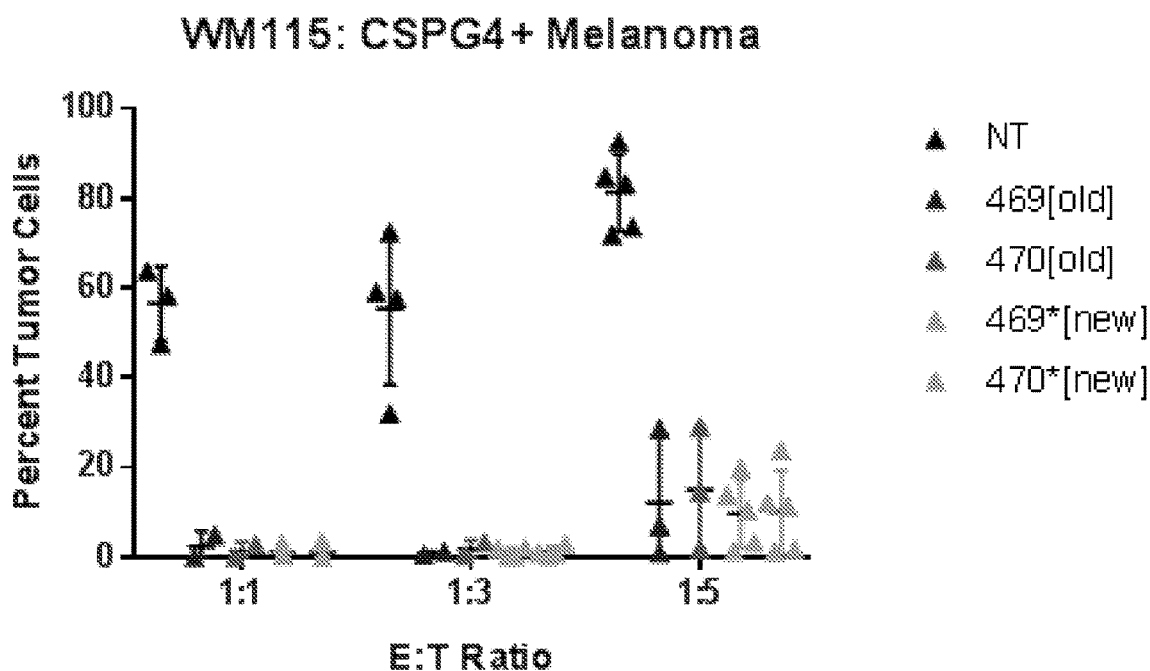

The present invention is explained in greater detail below. This description is not intended to be a detailed catalog of all the different ways in which the invention may be implemented, or all the features that may be added to the instant invention. For example, features illustrated with respect to one embodiment may be incorporated into other embodiments, and features illustrated with respect to a particular embodiment may be deleted from that embodiment. In addition, numerous variations and additions to the various embodiments suggested herein will be apparent to those skilled in the art in light of the instant disclosure which do not depart from the instant invention. Hence, the following specification is intended to illustrate some particular embodiments of the invention, and not to exhaustively specify all permutations, combinations and variations thereof.

Unless the context indicates otherwise, it is specifically intended that the various features of the invention described herein can be used in any combination. Moreover, the present invention also contemplates that in some embodiments of the invention, any feature or combination of features set forth herein can be excluded or omitted.

In the following description, certain details are set forth such as specific quantities, sizes, etc. so as to provide a thorough understanding of the present embodiments disclosed herein. However, it will be obvious to those skilled in the art that the present disclosure may be practiced without such specific details. In many cases, details concerning such considerations and the like have been omitted inasmuch as such details are not necessary to obtain a complete understanding of the present disclosure and are within the skills of persons of ordinary skill in the relevant art.

The present invention is based on the discovery of a chimeric antigen receptor (CAR) that targets cancer cells and/or cancer initiating cells (CICs) having a CSPG4 antigen. Accordingly, the present invention provides a chimeric antigen receptor (CAR) that targets cancer cells and/or CICs having a CSPG4 antigen, wherein the CAR comprises, consists essentially of and/or consists of the components described herein.

Thus, in one embodiment, the present invention provides a chimeric antigen receptor (CAR) comprising, consisting essentially of, or consisting of the amino acid sequence: Thus, in one embodiment, the present invention provides a chimeric antigen receptor (CAR) comprising the amino acid sequences:

(SEQ ID NO: 1)
QIQLVQSGPELKKPGETVKISCKASGYTFTDYSMHWVKKTPGKGLKWLG

WINTATGEPTY ADDFKGRFAISLETSARTVYLQINNLRNEDTATYFCF

SYYDYWGQGTTLTVSS (UNC 763.74 Vh1)

and (SEQ ID NO: 2)
DILLTQSPAILSVTPGETVSLSCRASQTIYKNLHWYQQKSHRSPRLLIK

YGSDSISGIPSRFTGSGSGTDYTLNINSVKPEDEGIYYCLQGYSTPWTF

GGGTKLEIK (UNC 763.74 Vk2), linked together in any orientation.

In an additional embodiment, the present invention provides a chimeric antigen receptor (CAR) comprising the amino acid sequences:

(SEQ ID NO: 3)
KVKLQESGGGLVQPGGSMKLSCVVSGFTFSNYWMNWVRQSPEKGLEWIA

EIRLKSNNFARYYAESVKGRFTISRDDSKSSVYLQMINLRAEDTGIYYC

TSYGNYVGHYFDHWGQGTTLTVSS (225.28 Vh1)

and (SEQ ID NO: 4)
DIVMTQSQKFMSTSVGDRVSVTCKASQNVDTNVAWYQQKPGQSPEPLLF

SASYRYTGVPDRFTGSGSGTDFTLTISNVQSEDLAEYFCQQYNSYPLTF

GGGTKLVIK (225.28 Vk), linked together in any orientation.

The present invention further provides a chimeric antigen receptor (CAR) comprising, consisting essentially of or consisting of the amino acid sequence:

(SEQ ID NO: 5)
AM EFGL SWL FLV AILK GVQ CDI LLTQ SPA ILS VTPG

ETV SLS CRAS QTI YKN LHWY QQK SHR SPRL LIK YGS

DSIS GIP SRF TGSG SGT DYT LNIN SVK PED EGIY YCL

-continued

QGY STPW TFG GGT KLEI KGG GGS GGGG SGG GGQ IQLV

QSG PEL KKPG ETV KIS CKAS GYT FTD YSMH WVK KTP

GKGL KWL GWI NTAT GEP TYA DDFK GRF AIS LETS ART

VYL QINN LRN EDT ATYF CFS YYD YWGQ GTT LTV SSTR C

[UNC 763.74 scFv (Vk2.Vh1)].

Additionally provided herein is a chimeric antigen receptor comprising, consisting essentially of or consisting of the amino acid sequence:

(SEQ ID NO: 6)
AM EFGL SWL FLV AILK GVQ CQI QLVQ SGP ELK KPGE

TVK ISC KASG YTF TDY SMHW VKK TPG KGLK WLG WIN

TATG EPT YAD DFKG RFA ISL ETSA RTV YLQ INNL RNE

DTA TYFC FSY YDY WGQG TTL TVS SGGG GSG GGG SGGG

GDI LLT QSPA ILS VTP GETV SLS CRA SQTI YKN LHW

YQQK SHR SPR LLIK YGS DSI SGIP SRF TGS GSGT DYT

LNI NSVK PED EGI YYCL QGY STP WTFG GGT KLE IKTR C

[UNC763.74 scFv (Vh1.Vk2)].

Also provided herein is a chimeric antigen receptor comprising, consisting essentially of or consisting of the amino acid sequence:

(SEQ ID NO: 7)
AM EFGL SWL FLV AILK GVQ CKV KLQE SGG GLV QPGG

SMK LSC VVSG FTF SNY WMNW VRQ SPE KGLE WIA EIR

LKSN NFA RYY AESV KGR FTI SRDD SKS SVY LQMI NLR

AED TGIY YCT SYG NYVG HYF DHW GQGT TLT VSS GGGG

SGG GGS GGGG DIV MTQ SQKF MST SVG DRVS VTC KAS

QNVD TNV AWY QQKP GOS PEP LLFS ASY RYT GVPD RFT

GSG SGTD FTL TIS NVQS EDL AEY FCQQ YNS YPL TFGG

GTK LVI KTRC [225.28 scFv (Vh1.Vk)].

Further provided herein is a chimeric antigen receptor comprising, consisting essentially of or consisting of the amino acid sequence (SEQ ID NO: 8)
AM EFGL SWL FLV AILK GVQ CDI VMTQ SQK FMS TSVG

DRV SVT CKAS QNV DTN VAWY QQK PGQ SPEP LLF SAS

YRYT GVP DRF TGSG SGT DFT LTIS NVQ SED LAEY FCQ

QYN SYPL TFG GGT KLVI KGG GGS GGGG SGG GGK VKLQ

ESG GGL VQPG GSM KLS CVVS GFT FSN YWMN WVR QSP

EKGL EWI AEI RIKS NNF ARY YAES VKG RFT ISRD DSK

SSV YLQM INL RAE DTGI YYC TSY GNYV GHY FDH WGQG

TTL TVS STRC [225.28 scFv (Vk.Vh1)].

In a further embodiment, the present invention provides a nucleic acid molecule encoding the CAR of this invention, including, in some embodiments, the nucleotide sequences provided herein. The present invention further provides vectors and cells comprising the nucleic acid molecule of this invention.

As one nonlimiting example, the present invention provides a nucleic acid molecule encoding a CAR of this invention, comprising, consisting essentially of or consisting of the nucleotide sequence:

(SEQ ID NO: 9)
TAGCCATGGAATTCGGCCTGAGCTGGCTGTTCCTGGTGGCCATCCTGAA

GGGCGTGCAGTGCGATATCCTGCTCACCCAGTCTCCAGCAATCCTGTCT

GTGACTCCAGGAGAAACAGTCAGTCTTTCCTGTAGGGCCAGCCAGACTA

TTTACAAGAACCTACACTGGTATCAACAGAAATCACATCGGTCTCCAAG

GCTTCTCATCAAGTATGGTTCTGATTCCATCTCTGGGATCCCCTCCAGG

TTCACTGGCAGTGGATCAGGGACAGATTACACTCTCAATATCAACAGTG

TGAAGCCCGAAGATGAAGGAATATATTACTGTCTTCAAGGTTACAGTAC

ACCTTGGACGTTCGGTGGAGGCACCAAGCTGGAAATCAAAGGTGGGGGC

GGTTCAGGCGGAGGTGGCTCTGGCGGTGGCGGACAGATCCAGTTGGTGC

AGTCTGGACCTGAGCTGAAGAAGCCTGGAGAGACAGTCAAGATCTCCTG

CAAGGCTTCTGGTTATACCTTCACAGACTATTCAATGCACTGGGTGAAG

AAGACTCCAGGAAAGGGTTTAAAGTGGCTGGGCTGGATAAACACTGCGA

CTGGTGAGCCAACATATGCAGATGACTTCAAGGGACGGTTTGCCATCTC

TTTGGAAACCTCTGCCAGGACTGTCTATTTGCAGATCAATAATCTCAGA

AATGAGGACACGGCTACATATTTCTGTTTTAGTTACTACGACTACTGGG

GCCAAGGCACCACTCTCACAGTTTCCTCAACGCGTTGC (scFv.763.74 VK2.VH1).

As another nonlimiting example, also provided herein is nucleic acid molecule encoding a CAR of this invention, comprising, consisting essentially of or consisting of the nucleotide sequence:

(SEQ ID NO: 10)
TAGCCATGGAATTCGGCCTGAGCTGGCTGTTCCTGGTGGCCATCCTGAA

GGGCGTGCAGTGCCAGATCCAGTTGGTGCAGTCTGGACCTGAGCTGAAG

AAGCCTGGAGAGACAGTCAAGATCTCCTGCAAGGCTTCTGGTTATACCT

TCACAGACTATTCAATGCACTGGGTGAAGAAGACTCCAGGAAAGGGTTT

AAAGTGGCTGGGCTGGATAAACACTGCGACTGGTGAGCCAACATATGCA

GATGACTTCAAGGGACGGTTTGCCATCTCTTTGGAAACCTCTGCCAGGA

CTGTCTATTTGCAGATCAATAATCTCAGAAATGAGGACACGGCTACATA

TTTCTGTTTTAGTTACTACGACTACTGGGGCCAAGGCACCACTCTCACA

GTTTCCTCAGGTGGGGCGGTTCAGGCGGAGGTGGCTCTGGCGGTGGCG

GAGATATCCTGCTCACCCAGTCTCCAGCAATCCTGTCTGTGACTCCAGG

AGAAACAGTCAGTCTTTCCTGTAGGGCCAGCCAGACTATTTACAAGAAC

CTACACTGGTATCAACAGAAATCACATCGGTCTCCAAGGCTTCTCATCA

AGTATGGTTCTGATTCCATCTCTGGGATCCCCTCCAGGTTCACTGGCAG

TGGATCAGGGACAGATTACACTCTCAATATCAACAGTGTGAAGCCCGAA

GATGAAGGAATATATTACTGTCTTCAAGGTTACAGTACACCTTGGACGT

TCGGTGGAGGCACCAAGCTGGAAATCAAAACGCGTTGC (scFv.763.74 VH1.VK2).

Further provided herein is a nucleic acid molecule encoding a CAR of this invention, comprising, consisting essentially of or consisting of the nucleotide sequence:

(SEQ ID NO: 11)
TAGCCATGGAATTCGGCCTGAGCTGGCTGTTCCTGGTGGCCATCCTGAA

GGGCGTGCAGTGCAAGGTGAAGCTGCAGGAGTCTGGAGGAGGCTTGGTG

CAACCTGGAGGATCCATGAAACTCTCCTGTGTTGTCTCTGGATTCACTT

TCAGTAATTACTGGATGAACTGGGTCCGCCAGTCTCCAGAGAAGGGGCT

TGAGTGGATTGCAGAAATTAGATTGAAATCCAATAATTTTGCAAGATAT

TATGCGGAGTCTGTGAAAGGGAGGTTCACCATCTCAAGAGATGATTCCA

AAAGTAGTGTCTACCTGCAAATGATCAACCTAAGAGCTGAAGATACTGG

CATTTATTACTGTACCAGTTATGGTAACTACGTTGGGCACTATTTTGAC

CACTGGGGCCAAGGCACCACTCTCACAGTCTCCTCAGGTGGGGCGGTT

CAGGCGGAGGTGGCTCTGGCGGTGGCGGAGACATTGTGATGACCCAGTC

TCAAAAATTCATGTCCACATCAGTAGGAGACAGGGTCAGCGTCACCTGC

AAGGCCAGTCAGAATGTGGATACTAATGTAGCCTGGTATCAACAAAAAC

CAGGGCAATCTCCTGAACCACTGCTTTTCTCGGCATCCTACCGTTACAC

TGGAGTCCCTGATCGCTTCACAGGCAGTGGATCTGGGACAGATTTCACT

CTCACCATCAGCAATGTGCAGTCTGAAGACTTGGCAGAGTATTTCTGTC

AGCAATATAACAGCTATCCTCTGACGTTCGGTGGAGGCACCAAGCTGGT

GATCAAAACGCGTTGC (scFv225.28 VH1.VK).

In additional embodiments, the present invention provides a nucleic acid molecule encoding a CAR of this invention, comprising, consisting essentially of or consisting of the nucleotide sequence:

(SEQ ID NO: 12)
TAGCCATGGAATTCGGCCTGAGCTGGCTGTTCCTGGTGGCCATCCTGAA

GGGCGTGCAGTGCGACATTGTGATGACCCAGTCTCAAAAATTCATGTCC

ACATCAGTAGGAGACAGGGTCAGCGTCACCTGCAAGGCCAGTCAGAATG

TGGATACTAATGTAGCCTGGTATCAACAAAAACCAGGGCAATCTCCTGA

ACCACTGCTTTTCTCGGCATCCTACCGTTACACTGGAGTCCCTGATCGC

TTCACAGGCAGTGGATCTGGGACAGATTTCACTCTCACCATCAGCAATG

TGCAGTCTGAAGACTTGGCAGAGTATTTCTGTCAGCAATATAACAGCTA

TCCTCTGACGTTCGGTGGAGGCACCAAGCTGGTGATCAAAGGTGGGGGC

GGTTCAGGCGGAGGTGGCTCTGGCGGTGGCGGAAAGGTGAAGCTGCAGG

AGTCTGGAGGAGGCTTGGTGCAACCTGGAGGATCCATGAAACTCTCCTG

TGTTGTCTCTGGATTCACTTTCAGTAATTACTGGATGAACTGGGTCCGC

CAGTCTCCAGAGAAGGGGCTTGAGTGGATTGCAGAAATTAGATTGAAAT

CCAATAATTTTGCAAGATATTATGCGGAGTCTGTGAAAGGGAGGTTCAC

CATCTCAAGAGATGATTCCAAAAGTAGTGTCTACCTGCAAATGATCAAC

CTAAGAGCTGAAGATACTGGCATTTATTACTGTACCAGTTATGGTAACT

ACGTTGGGCACTATTTTGACCACTGGGGCCAAGGCACCACTCTCACAGT

CTCCTCAACGCGTTGC (scFv225.28 VK.VH1).

In particular embodiments, the chimeric antigen receptor (CAR) of this invention has one, two, three, four, or more components, and in some embodiments the one, two, three, four or more components facilitate targeting and/or binding of the CAR to a CSPG4 antigen-comprising cancer cell and/or a cancer initiating cell (CIC), although in some cases one or more components can be useful to promote and/or maintain growth and/or maturity of the cell comprising the CAR.

Further provided herein is a vector, as well as a nucleic acid construct comprising the nucleic acid molecule of this invention.

In some embodiments, the present invention provides an isolated cell comprising the CAR of this invention and in some embodiments, the present invention provides an isolated cell comprising the nucleic acid molecule of this invention.

Nonlimiting examples of a cell of this invention include an αβT cell, a natural killer (NK) cell, a cytotoxic T lymphocyte (CTL), a regulatory T cell, a natural killer T (NKT) cell, a Th17 cell, a ΓδT cell, and any combination thereof.

In some embodiments, the present invention provides a cytotoxic T lymphocyte comprising a CAR that recognizes and binds CSPG4 antigen. The cytotoxic T lymphocyte can be transduced with a viral vector or transfected with a plasmid or nucleic acid construct comprising a nucleotide sequence encoding the CAR of this invention.

In certain embodiments, the present invention includes T lymphocytes engineered to comprise a chimeric antigen receptor having an antibody, antigen binding fragment and/or engineered antibody specific for CSPG4, part or all of a cytoplasmic signaling domain, and/or part or all of one or more costimulatory molecules, for example endodomains of costimulatory molecules. In specific embodiments, the antibody for CSPG4 is a single-chain variable fragment (scFv), although in certain aspects the antibody can be directed at other target antigens on the cell surface, such as HER2 or CD19, for example. In certain embodiments, a cytoplasmic signaling domain, such as those derived from the T cell receptor zeta chain, can be included as at least part of the chimeric antigen receptor in order to produce stimulatory signals for T lymphocyte proliferation and effector function following engagement of the chimeric antigen receptor with the target antigen. Examples include, but are not limited to, endodomains from co-stimulatory molecules such as CD28, 4-1BB, and OX40 or the signaling components of cytokine receptors such as interleukin 7 (IL7), interleukin 15 (IL15) and interleukin 12 (IL12). In particular embodiments, costimulatory molecules are employed to enhance the activation, proliferation and/or cytotoxicity of T cells produced as a result of antigen engagement with the CAR. In specific embodiments, the costimulatory molecules can be CD28, OX40, and 4-1BB and cytokine receptors. Nonlimiting examples of cytokine receptors of this invention include IL7 and IL15.

Genetic engineering of human T lymphocytes to express tumor-directed chimeric antigen receptors (CARs) can produce antitumor effector cells that bypass tumor immune escape mechanisms that are due to abnormalities in protein-antigen processing and presentation.

In certain embodiments, the present invention provides cells specific for the CSPG4 antigen, wherein said cells have a chimeric antigen receptor specific for CSPG4 antigen on the cell surface.

In some embodiments, the CAR of this invention can comprise, consist essentially of and/or consist of the effector domain of the T cell receptor zeta chain or a related signal transduction endodomain derived from a T cell receptor. In some embodiments the chimeric antigen receptor of this invention is encoded by a nucleotide sequence. Thus, the present invention further provides a vector (e.g., a viral vector) comprising the nucleotide sequence of this invention encoding a CAR of this invention and the T lymphocytes of this invention can be transduced with a viral vector comprising the nucleotide sequence of this invention under conditions whereby the chimeric antigen receptor of this invention is produced in the T lymphocyte.

As used herein, the term "co-stimulatory molecule" refers to a molecular component that promotes activation, proliferation and effector function of a T cell after engagement of an antigen specific receptor. In some embodiments, the CAR of this invention can comprise one or more (e.g., 2, 3, 4, 5, 6, 7, 8, 9, 10, etc.) co-stimulatory molecules and/or active fragments thereof, nonlimiting examples of which include CD28, OX40, 4-1BB or any other co-stimulatory molecule and/or active fragment thereof now known or later identified, singly or in any combination.

In further embodiments, the chimeric antigen receptor (CAR) of this invention can further comprise a detectable moiety as would be known in the art and/or an effector molecule, nonlimiting examples of which include a drug, a toxin, a small molecule, a cytokine, an oncolytic virus, an enzyme, a nanoparticle, a biomaterial, a scaffold, an antibody, and/or an antibody fragment, singly or in any combination.

As used herein, the term "cytoplasmic signaling domain" refers to the component of a co-stimulatory molecule or cytokine receptor that exists inside the cell and is responsible for transducing the external signal received to the internal metabolic processes of the cell, thereby altering its phenotype and function.

In some embodiments of the present invention, the overexpression of CSPG4 by cancer cells allows these cells to be targeted in vitro and in vivo by CSPG4 CAR-expressing T cells, and in some embodiments, incorporation of endodomains (e.g., from both CD28 and OX40 molecules and/or from CD28 and/or from 4-1BB) mediates co-stimulation of the T lymphocytes, inducing T cell activation, proliferation, and/or cytotoxicity against CSPG4-positive cancer and/or CIC cells.

In particular embodiments of the invention, there are methods for killing cancer cells using genetically manipulated T-cells that express a chimeric antigen receptor (CAR) directed against the antigen CSPG4. In some embodiments, engagement (antigen binding) of this CAR leads to activation of the linked T-cell receptor ζ chain and the costimulatory molecules CD28 and 4-1BB.

In particular embodiments of the invention, the CAR receptor comprises a single-chain variable fragment (scFv) that recognizes CSPG4. The skilled artisan recognizes that scFv is a fusion protein of the variable regions of the heavy (VH) and light chains (VL) of immunoglobulins, connected with a short linker peptide of about ten to about 25 amino acids. In some embodiments, the linker peptide sequence may be rich in glycine for flexibility and/or it may have serine or threonine for solubility, in certain cases. The scFv may be generated by methods known in the art and in some embodiments, the scFv can be humanized, caninized, felinized, or equinized according to protocols know in the art.

In some embodiments, the linker peptide sequence can comprise (GGGS)n subunits in any combination and n can be 1 or any number greater than 1 (e.g., 2, 3, 4, 5, 6, 7, 8, 9, 10, 11, 12, 13, 14, 15, 16, 17, 18, 19, 20, 25, 30, 35, 40, 45, 50, etc.). In some embodiments, the linker peptide can comprise, consist essentially of, or consist of the amino acid sequence: GGGGSGGGGSGGGGS (SEQ ID NO:13).

In certain aspects, cytokine exodomains and/or other ligand/receptor molecules can be used as exodomains to provide targeting to tumor cells.

The skilled artisan recognizes that T cells utilize co-stimulatory signals that are antigen non-specific to become fully activated. In particular cases they are provided by the interaction between co-stimulatory molecules expressed on the membrane of an antigen presenting cell (APC) and the T cell. In specific embodiments, the one or more costimulatory molecules in the chimeric antigen receptor can come from the B7/CD28 family, TNF superfamily, or the signaling lymphocyte activation molecule (SLAM) family. Exemplary costimulatory molecules include one or more of the following in any combination: B7-1/CD80; CD28; B7-2/CD86; CTLA-4; B7-H1/PD-L1; ICOS; B7-H2; PD-1; B7-H3; PD-L2; B7-H4; PDCD6; BTLA; 4-1BB/TNFRSF9/CD137; CD40 Ligand/TNFSF5; 4-1BB Ligand/TNFSF9; GITR/TNFRSF18; BAFF/BLyS/TNFSF13B; GITR Ligand/TNFSF18; BAFF R/TNFRSF13C; HVEM/TNFRSF14; CD27/TNFRSF7; LIGHT/TNFSF14; CD27 Ligand/TNFSF7; OX40/TNFRSF4; CD30/TNFRSF8; OX40 Ligand/TNFSF4; CD30 Ligand/TNFSF8; TACI/TNFRSF13B; CD40/TNFRSF5; 2B4/CD244/SLAMF4; CD84/SLAMF5; BLAME/SLAMF8; CD229/SLAMF3; CD2 CRACC/SLAMF7; CD2F-10/SLAMF9; NTB-A/SLAMF6; CD48/SLAMF2; SLAM/CD150; CD58/LFA-3; CD2; Ikaros; CD53; Integrin alpha 4/CD49d; CD82/Kai-1; Integrin alpha 4 beta 1; CD90/Thy 1; Integrin alpha 4 beta 7/LPAM-1; CD96; LAG-3; CD160; LMIR1/CD300A; CRTAM; TCL1A; DAP12; TIM-1/KIM-1/HAVCR; Dectin-1/CLEC7A; TIM-4; DPPIV/CD26; TSLP; EphB6; TSLP R; and HLA-DR.

The effector domain is a signaling domain that transduces the event of receptor ligand binding to an intracellular signal that partially activates the T lymphocyte. Absent appropriate co-stimulatory signals, this event is insufficient for useful T cell activation and proliferation. A nonlimiting example of an effector domain of this invention is the effector domain of the T cell receptor zeta chain.

The present invention additionally provides embodiments of the amino acid sequences and nucleotide sequences of this invention wherein the amino acid sequence and/or the nucleotide sequence has at least 60% (e.g., 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94 95, 96, 97, 98, 99 or 100%) identity with the amino acid sequence and/or nucleotide sequences described herein. The present invention further encompasses all nucleotide sequences that encode the amino acid sequences described herein.

In further embodiments, the present invention provides a composition (e.g., a pharmaceutical composition) comprising, consisting essentially of and/or consisting of the CAR of this invention, the nucleic acid molecule of this invention, the vector of this invention and/or the cell of this invention, in a pharmaceutically acceptable carrier.

The present invention also provides methods employing the CAR of this invention. Thus, in one embodiment, the present invention provides a method of stimulating a T cell-mediated immune response to a CSPG4 expressing target cell population and/or tissue in a subject, comprising administering to the subject an effective amount of the CAR of this invention, the nucleic acid molecule of this invention, the vector of this invention, and/or the cell of this invention, thereby stimulating a T cell-mediated immune response to the CSPG4 expressing target cell population and/or tissue in the subject.

In another embodiment, the present invention provides a method of providing an anti-tumor immunity (e.g., an immune response to tumor cells) in a subject, comprising administering to the subject an effective amount of the CAR of this invention, the nucleic acid molecule of this invention, the vector of this invention, and/or the cell of this invention, thereby providing an anti-tumor immunity in the subject.

In a further embodiment, the present invention provides a method of treating a subject having a disease or disorder associated with elevated expression of CSPG4 by a cell of the subject, comprising administering to the subject an effective amount of the CAR of this invention, the nucleic acid molecule of this invention, the vector of this invention, and/or the cell of this invention, thereby treating the subject having the disease or disorder associated with elevated expression of CSPG4 by the cell of the subject.

In addition, the present invention provides a method of generating a population of genetically engineered T cells in a subject (e.g., a subject diagnosed with cancer and/or otherwise in need thereof), comprising administering to the subject a T cell genetically engineered to express the CAR of this invention, wherein the population of genetically engineered T cells persists in the subject for a period of time (e.g., at least one week, one month two months, three months, four months, five months, nine months, one year, two years, five years, etc.) following administration to the subject.

Additionally provided herein is a method of expanding a population of genetically engineered cells in a subject (e.g., a subject diagnosed with cancer and/or a subject in need thereof), comprising administering to the subject a cell genetically engineered to express the CAR of this invention, wherein the administered genetically engineered cell produces a population of progeny cells in the subject.

In additional embodiments of this invention, a method is provided of treating cancer in a subject (e.g., a subject in need thereof), comprising administering to the subject an effective amount of the CAR of this invention, the nucleic acid molecule of this invention, the vector of this invention, and/or the cell of this invention, thereby treating cancer in the subject. In some embodiments, the subject of this method has had and/or is having therapy for cancer.

Thus, in an additional embodiment of this invention, the present invention provides a method of treating cancer in a subject, comprising administering to the subject cytotoxic T lymphocytes having a chimeric antigen receptor that recognizes a CSPG4 antigen on the surface of cancer cells and/or cancer initiating cells (CICs).

In further embodiments of this invention, a method is provided of preventing cancer in a subject (e.g., a subject in need thereof), comprising administering to the subject an effective amount of the CAR of this invention, the nucleic acid molecule of this invention, the vector of this invention, and/or the cell of this invention, thereby preventing cancer in the subject.

In one embodiment, the present invention provides a method of targeting a cancer cell and/or a cancer initiating cell (CIC) having a CSPG4 antigen, comprising providing to the cancer cell and/or the CIC, or contacting the cancer cell and/or the CIC, with a cell comprising the CAR of this invention.

In some embodiments of this invention, the cell of this invention (e.g., a $\alpha\beta$T cell, a natural killer (NK) cell, a cytotoxic T lymphocyte (CTL), a regulatory T cell, a natural killer T (NKT) cell, a Th17 cell, a $\gamma\delta$T cell) can be an autologous cell from the subject to whom treatment is administered. In some embodiments, the cell of this invention can be from a different individual of the same species as the subject receiving treatment or from an individual of a different species from the subject receiving treatment. In some embodiments, the cell can be of the same species of the subject and in some embodiments, the cell can be of a species that is different than the species of the subject.

In the methods of this invention, the cancer cell and/or CIC can be in vitro, ex vivo, and/or in vivo. In some embodiments, the cell can be in a subject. In some embodiments, the cell can be an autologous cell. In some embodiments, the cell is not an autologous cell. In some embodiments, the cell is of the same species of the subject. In some embodiments, the cell is of a species that is different than the species of the subject.

In further embodiments, the present invention provides a method of detecting cancer cells and/or cancer initiating cells (CICs) in a cell sample, comprising: a) contacting the cell sample with the CAR of this invention under conditions whereby a binding complex can form; and b) detecting formation of the binding complex, wherein detection of the binding complex is indicative of cancer cells and/or CICs in the cell sample.

In another embodiment, the present invention provides a method of detecting cancer cells and/or cancer initiating cells (CICs) in a subject, comprising: a) contacting a cell sample obtained from the subject with the CAR of this invention under conditions whereby a binding complex can form; and b) detecting formation of the binding complex, wherein detection of the binding complex is indicative of the presence of cancer cells and/or CICs in the subject.

In some embodiments, the cancer of this invention can be a cancer associated with increased expression or overexpression of CSPG4 antigen and in some embodiments, cancer cells and CICs of this invention can overexpress the CSPG4 antigen relative to a noncancerous cell or a cancer cell of a cancer that is not associated with increased expression or overexpression of CSPG4 antigen.

In some embodiments, the cancer cells and/or CICs of this invention can be contacted with LDE225, an inhibitor of the sonic hedgehog homolog (SHH) pathway, before, during and/or after contacting with the CAR of this invention.

The term "cancer" as used herein is defined as disease characterized by the rapid and uncontrolled growth of aberrant cells. Cancer cells can spread locally or through the bloodstream and lymphatic system to other parts of the body.

Nonlimiting examples of a cancer that can be treated according to the methods of this invention include B cell lymphoma. T cell lymphoma, myeloma, leukemia, hematopoietic neoplasias, thymoma, lymphoma, sarcoma, lung cancer, liver cancer, non-Hodgkins lymphoma. Hodgkins lymphoma, skin cancer, uterine cancer, cervical cancer, endometrial cancer, adenocarcinoma, breast cancer, glioblastoma, pancreatic cancer, colorectal cancer, anal cancer, lung cancer, renal cancer, bladder cancer, liver cancer, prostate cancer, ovarian cancer, primary or metastatic melanoma, squamous cell carcinoma, basal cell carcinoma, brain cancer, angiosarcoma, hemangiosarcoma, head and neck carcinoma, thyroid carcinoma, soft tissue sarcoma, bone sarcoma, testicular cancer, gastrointestinal cancer, and any other cancer now known or later identified (see, e.g., Rosenberg (1996) Ann. Rev. Med. 47:481-491, the entire contents of which are incorporated by reference herein).

In certain embodiments of the invention, methods of the present invention for clinical aspects are combined with other agents effective in the treatment of hyperproliferative disease, such as anti-cancer agents. An "anti-cancer" agent is capable of negatively affecting cancer in a subject, for example, by killing cancer cells, inducing apoptosis in cancer cells, reducing the growth rate of cancer cells, reducing the incidence or number of metastases, reducing tumor size, inhibiting tumor growth, reducing the blood supply to a tumor or cancer cells, promoting an immune response against cancer cells or a tumor, preventing or inhibiting the progression of cancer, and/or increasing the lifespan of a subject with cancer. More generally, these other compositions would be provided in a combined amount effective to kill or inhibit proliferation of the cancer cell. This process may involve contacting the cancer cells with the nucleic acid molecule, vector and/or cell of this invention and the agent(s) or multiple factor(s) at the same time. This may be achieved by contacting the cell with a single composition or pharmacological formulation that includes both agents, or by contacting the cell with two distinct compositions or formulations, at the same time, wherein one composition includes the nucleic acid molecule, vector and/or cell of the invention and the other composition includes the second agent(s).

Tumor cell resistance to chemotherapy and radiotherapy agents represents a major problem in clinical oncology. One goal of current cancer research is to find ways to improve the efficacy of chemo- and radiotherapy by combining it with gene therapy. For example, the herpes simplex-thymidine kinase (HS-tK) gene, when delivered to brain tumors by a retroviral vector system, successfully induced susceptibility to the antiviral agent ganciclovir. In the context of the present invention, it is contemplated that cell therapy could be used similarly in conjunction with chemotherapeutic, radiotherapeutic, or immunotherapeutic intervention, in addition to other pro-apoptotic or cell cycle regulating agents.

Alternatively, the present inventive therapy may precede and/or follow the other agent treatment(s) by intervals ranging from minutes to weeks. In embodiments where the other agent and the CAR of the present invention are applied separately to the individual, one would generally ensure that a significant period of time did not expire between the time of each delivery, such that the agent and inventive therapy would still be able to exert an advantageously combined effect on the cell. In such instances, it is contemplated that one may contact the cell with the multiple modalities within about 12-24 h of each other and, more preferably, within about 6-12 h of each other. In some situations, it may be desirable to extend the time period for treatment significantly, however, where several days (2, 3, 4, 5, 6 or 7) to several weeks (1, 2, 3, 4, 5, 6, 7 or 8) lapse between the respective administrations.

It is expected that the treatment cycles would be repeated as necessary. It also is contemplated that various standard therapies, as well as surgical intervention, may be applied in combination with the inventive cell therapy.

Cancer therapies also include a variety of combination therapies with both chemical and radiation based treatments. Combination chemotherapies include, for example, abraxane, altretamine, docetaxel, herceptin, methotrexate, novantrone, zoladex, cisplatin (CDDP), carboplatin, procarbazine, mechlorethamine, cyclophosphamide, camptothecin, ifosfamide, melphalan, chlorambucil, busulfan, nitrosurea, dactinomycin, daunorubicin, doxorubicin, bleomycin, plicomycin, mitomycin, etoposide (VP16), tamoxifen, raloxifene, estrogen receptor binding agents, taxol, gemcitabine, navelbine, farnesyl-protein transferase inhibitors, transplatinum, 5-fluorouracil, vincristine, vinblastin and methotrexate, or any analog or derivative variant of the foregoing.

In specific embodiments, chemotherapy for CSPG4 positive cancer is employed in conjunction with the invention, for example before, during and/or after administration of the invention.

In some embodiments, the subject of this invention can be receiving or has received and/or will receive hormone therapy.

Other factors that cause DNA damage and have been used extensively include what are commonly known as gamma-rays, X-rays, and/or the directed delivery of radioisotopes to tumor cells. Other forms of DNA damaging factors are also contemplated such as microwaves and UV-irradiation. It is most likely that all of these factors affect a broad range of damage on DNA, on the precursors of DNA, on the replication and repair of DNA, and on the assembly and maintenance of chromosomes. Dosage ranges for X-rays range from daily doses of 50 to 200 roentgens for prolonged periods of time (3 to 4 wk), to single doses of 2000 to 6000 roentgens. Dosage ranges for radioisotopes vary widely, and depend on the half-life of the isotope, the strength and type of radiation emitted, and the uptake by the neoplastic cells.

The terms "contacted with," "provided to" and "exposed to," when applied to a cell, are used herein to describe the process by which a therapeutic agent (e.g., a CAR) is delivered to a target cell and/or are placed in direct juxtaposition with the target cell, e.g., under conditions that facilitate binding of the CAR to the target antigen in and/or on the target cell. In some embodiments, chemotherapy and/or radiation therapy can also be included before, after and/or during the contacting or exposing or providing to step to achieve cell killing or stasis, wherein both agents are delivered to a cell in a combined amount effective to kill the cell or prevent it from dividing.

Immunotherapeutics generally rely on the use of immune effector cells and molecules to target and destroy cancer cells. The immune effector may be, for example, an antibody specific for some marker on the surface of a tumor cell. The antibody alone may serve as an effector of therapy or it may recruit other cells to actually affect cell killing. The antibody also may be conjugated to a drug or toxin (chemotherapeutic, radionuclide, ricin A chain, cholera toxin, pertussis toxin, etc.) and serve merely as a targeting agent. Alternatively, the effector may be a lymphocyte carrying a surface molecule that interacts, either directly or indirectly, with a tumor cell target. Various effector cells include cytotoxic T cells and NK cells.

Immunotherapy could thus be used as part of a combined therapy, in conjunction with the present cell therapy. The general approach for combined therapy is discussed herein. Generally, the tumor cell must bear some marker that is amenable to targeting, i.e., is not present on the majority of other cells. Many tumor markers exist and any of these may be suitable for targeting in the context of the present invention. Common tumor markers include carcinoembryonic antigen, prostate specific antigen, urinary tumor associated antigen, fetal antigen, tyrosinase (p97), gp68, TAG-72, HMFG, Sialyl Lewis Antigen, MucA, MucB, PLAP, estrogen receptor, laminin receptor, erb B and p155.

Immunotherapy for a cancer of this invention may include interleukin-2 (IL-2) or interferon (IFN), for example.

In yet another embodiment, the secondary treatment can be a gene therapy in which a therapeutic polynucleotide is administered before, after, and/or at the same time as the present invention clinical embodiments. A variety of expression products are encompassed within the invention, including inducers of cellular proliferation, inhibitors of cellular proliferation, or regulators of programmed cell death.

Approximately 60% of persons with cancer will undergo surgery of some type, which includes preventative, diagnostic or staging, curative and palliative surgery. Curative surgery is a cancer treatment that may be used in conjunction with other therapies, such as the treatment of the present invention, chemotherapy, radiotherapy, hormonal therapy, gene therapy, immunotherapy and/or alternative therapies.

Curative surgery includes resection in which all or part of cancerous tissue is physically removed, excised, and/or destroyed. Tumor resection refers to physical removal of at least part of a tumor. In addition to tumor resection, treatment by surgery includes laser surgery, cryosurgery, electrosurgery, and microscopically controlled surgery (Mohs' surgery). It is further contemplated that the present invention may be used in conjunction with removal of superficial cancers, precancers, or incidental amounts of normal tissue.

Upon excision of part of all of cancerous cells, tissue, or tumor, a cavity may be formed in the body. Treatment may be accomplished by perfusion, direct injection or local application of the area with an additional anti-cancer therapy. Such treatment may be repeated, for example, every 1, 2, 3, 4, 5, 6, or 7 days, or every 1, 2, 3, 4, and 5 weeks or every 1, 2, 3, 4, 5, 6, 7, 8, 9, 10, 11, or 12 months. These treatments may be of varying dosages as well.

It is contemplated that other agents may be used in combination with the present invention to improve the therapeutic efficacy of treatment. These additional agents include immunomodulatory agents, agents that affect the upregulation of cell surface receptors and GAP junctions, cytostatic and differentiation agents, inhibitors of cell adhesion, or agents that increase the sensitivity of the hyperproliferative cells to apoptotic inducers. Immunomodulatory agents include tumor necrosis factor; interferon alpha, beta, and gamma; IL-2 and other cytokines; F42K and other cytokine analogs; or MIP-1, MIP-1beta, MCP-1, RANTES, and other chemokines. It is further contemplated that the upregulation of cell surface receptors or their ligands such as Fas/Fas ligand, DR4 or DR5/TRAIL would potentiate the apoptotic inducing abilities of the present invention by establishment of an autocrine or paracrine effect on hyperproliferative cells. Increasing intercellular signaling by elevating the number of GAP junctions would increase the anti-hyperproliferative effects on the neighboring hyperproliferative cell population. In other embodiments, cytostatic or differentiation agents can be used in combination with the present invention to improve the anti-hyperproliferative efficacy of the treatments. Inhibitors of cell adhesion are contemplated to improve the efficacy of the present invention. Examples of cell adhesion inhibitors are focal adhesion kinase (FAKs) inhibitors and lovastatin. It is further contemplated that other agents that increase the sensitivity of a hyperproliferative cell to apoptosis, such as the antibody c225, could be used in combination with the present invention to improve the treatment efficacy.

Definitions

As used herein, "a," "an" and "the" can mean one or more than one, depending on the context in which it is used. For example, "a" cell can mean one cell or multiple cells.

Also as used herein, "and/or" refers to and encompasses any and all possible combinations of one or more of the associated listed items, as well as the lack of combinations when interpreted in the alternative ("or").

Furthermore, the term "about," as used herein when referring to a measurable value such as an amount of a compound or agent of this invention, dose, time, temperature, and the like, is meant to encompass variations of ±20%, ±10%, ±5%, ±1%, ±0.5%, or even ±0.1% of the specified amount.

As used herein, the transitional phrase "consisting essentially of" means that the scope of a claim is to be interpreted to encompass the specified materials or steps recited in the claim, "and those that do not materially affect the basic and novel characteristic(s)" of the claimed invention. See, In re Herz, 537 F.2d 549, 551-52, 190 USPQ 461, 463 (CCPA 1976) (emphasis in the original); see also MPEP § 2111.03. Thus, the term "consisting essentially of" when used in a claim of this invention is not intended to be interpreted to be equivalent to "comprising."

Also as used herein, "one or more" means one, two, three, four, five, six, seven, eight, nine, ten, 11, 12, 13, 14, 15, 16, 17, 18, 19, 20, etc.

Subjects that may be treated by the present invention include both human subjects for medical and/or therapeutic purposes and animal subjects for veterinary and drug screening and development purposes. Other suitable animal subjects are, in general, mammalian subjects such as primates, bovines, ovines, caprines, porcines, equines, felines, canines, lagomorphs, rodents (e.g., rats and mice), etc. Human subjects are the most preferred. Human subjects include fetal, neonatal, infant, juvenile, adult and geriatric subjects.

The term "anti-tumor effect" as used herein, refers to a biological effect which can be manifested by a decrease in tumor volume, a decrease in the number of tumor cells, a decrease in the proliferation rate, a decrease in the number of metastases, an increase in life expectancy, and/or amelioration of various physiological symptoms associated with the cancerous condition. An "anti-tumor effect" can also be manifested by the ability of the peptides, polynucleotides, cells and antibodies of the invention to prevent and/or delay the occurrence of tumor in the first place.

The term "auto-antigen" means, in accordance with the present invention, any self-antigen which is mistakenly recognized by the immune system as being foreign. Auto-antigens comprise, but are not limited to, cellular proteins, phosphoproteins, cellular surface proteins, cellular lipids, nucleic acids, and glycoproteins, including cell surface receptors.

As used herein, the term "autologous" is meant to refer to any material derived from the same individual to whom it is later to be re-introduced.

"Allogeneic" refers to a graft derived from a different animal of the same species, "Xenogeneic" refers to a graft derived from an animal of a different species.

"Treat" or "treating" as used herein refers to any type of treatment that imparts a benefit to a subject that has a disease or disorder or is at risk of having or developing the disease or disorder, including, for example, improvement in the condition of the subject (e.g., in one or more symptoms) and/or slowing of the progression of symptoms, etc.

As used herein, "prevent," "preventing" or "prevention" includes prophylactic treatment of the subject to prevent the onset or advancement of a disorder, as determined, e.g., by the absence or delay in the manifestation of symptoms associated with the disorder. As used herein, "prevent," "preventing" or "prevention" is not necessarily meant to imply complete abolition of symptoms.

"Treatment effective amount," "effective amount," "amount effective to treat" or the like as used herein means an amount of the antibody or fragment thereof or CAR or cell of this invention sufficient to produce a desirable effect upon a patient that has a disease, disorder and/or condition of this invention. This includes improvement in the condition of the patient (e.g., in one or more symptoms), delay in the progression of the disease, etc.

"Pharmaceutically acceptable" as used herein means that the compound or composition is suitable for administration to a subject to achieve the treatments described herein, without unduly deleterious side effects in light of the severity of the disease and necessity of the treatment.

"Antibody" or "antibodies" as used herein refers to all types of immunoglobulins, including IgG, IgM, IgA, IgD, and IgE. The term "immunoglobulin" includes the subtypes of these immunoglobulins, such as $IgG_1$, $IgG_2$, $IgG_3$, $IgG_4$, etc. The antibodies may be of any species of origin, including (for example) mouse, rat, rabbit, horse, or human, or may be chimeric or humanized antibodies. The term "antibody" as used herein includes antibody fragments which retain the capability of binding to a target antigen, for example, Fab, $F(ab')_2$, and Fv fragments, and the corresponding fragments obtained from antibodies other than IgG. Such fragments are also produced by known techniques. In some embodiments antibodies may be coupled to or conjugated to a detectable group or therapeutic group in accordance with known techniques.

Furthermore, the term "antibody" as used herein, is intended to refer to immunoglobulin molecules comprising four polypeptide chains, two heavy (H) chains and two light (L) chains inter-connected by disulfide bonds. Each heavy chain comprises a heavy chain variable region (abbreviated herein as HCVR or VH) and a heavy chain constant region. The heavy chain constant region comprises three domains, CH1, CH2 and CH3. Each light chain comprises a light chain variable region (abbreviated herein as LCVR or VL) and a light chain constant region. The light chain constant region comprises one domain (CL1). The VH and VL regions can be further subdivided into regions of hypervariability, termed complementary determining regions (CDR), interspersed with regions that are more conserved, termed framework regions (FR). In various embodiments of the antibody or antigen binding fragment thereof of the invention, the FRs may be identical to the human germline sequences, or may be naturally or artificially modified. Each VH and VL is composed of three CDRs and four FRs, arranged from amino-terminus to carboxy-terminus in the following order: FR1, CDR1, FR2, CDR2, FR3, CDR3, FR4.

In some embodiments, the antibodies and antigen binding fragments thereof of the present invention possess very high affinities, typically possessing $K_D$ values of from about $10^{-8}$ through about $10^{-12}$ M or higher, for example, at least $10^{-8}$ M, at least $10^{-9}$ M, at least $10^{-10}$ M, at least $10^{-11}$ M, or at least $10^{-12}$ M, when measured by binding to antigen presented on cell surface.

In some embodiments, the antibodies and antigen binding fragments thereof of the present invention possess very high affinities, typically possessing $EC_{50}$ values of from about $10^{-8}$ through about $10^{-12}$ M or higher, for example, at least $10^{-8}$ M, at least $10^{-9}$ M, at least $10^{-10}$ M, at least $10^{-11}$ M, or at least $10^{-12}$ M, when measured by binding to antigen presented on cell surface.

The term "antigen-binding portion" or "antigen-binding fragment" of an antibody (or simply "antibody portion" or "antibody fragment"), as used herein, refers to one or more fragments, portions or domains of an antibody that retain the ability to specifically bind to an antigen. It has been shown that fragments of a full-length antibody can perform the antigen-binding function of an antibody. Examples of binding fragments encompassed within the term "antigen-binding portion" of an antibody include (i) an Fab fragment, a monovalent fragment consisting of the VL, VH, CL1 and CH1 domains; (ii) an $F(ab')_2$ fragment, a bivalent fragment comprising two F (ab)' fragments linked by a disulfide bridge at the hinge region; (iii) an Fd fragment consisting of the VH and CH1 domains; (iv) an Fv fragment consisting of the VL and VH domains of a single arm of an antibody; (v) a dAb fragment (Ward et al. (1989) *Nature* 241:544-546), which consists of a VH domain; and (vi) an isolated complementary determining region (CDR). Furthermore, although the two domains of the Fv fragment, VL and VH, are coded for by separate genes, they can be joined, using recombinant methods, by a synthetic linker that enables them to be made as a single contiguous chain in which the VL and VH regions pair to form monovalent molecules (known as single chain Fv (scFv); see e.g., Bird et al. (1988) Science 242:423-426; and Huston et al. (1988) *Proc. Natl. Acad. Sci. USA* 85:5879-5883). Such single chain antibodies are also intended to be encompassed within the term "antigen-binding portion" of an antibody. Other forms of single chain antibodies, such as diabodies, are also encompassed (see e.g., Holliger et al. (1993) *Proc. Natl. Acad Sci. USA* 90:6444-6448).

The term "epitope" refers to an antigenic determinant that interacts with a specific antigen binding site in the variable region of an antibody molecule known as a paratope. A single antigen may have more than one epitope. Epitopes may be either conformational or linear. A conformational epitope is produced by spatially juxtaposed amino acids from different segments of one (or more) linear polypeptide chain(s). A linear epitope is an epitope produced by adjacent amino acid residues in a polypeptide chain. In certain embodiments, an epitope may include other moieties, such as saccharides, phosphoryl groups, or sulfonyl groups on the antigen.

The term "antibody fragment" refers to a portion of an intact antibody and refers to the antigenic determining variable regions of an intact antibody. Examples of antibody fragments include, but are not limited to, Fab, Fab', F(ab')2, and Fv fragments, linear antibodies, scFv antibodies, and multispecific antibodies formed from antibody fragments.

An "antibody heavy chain," as used herein, refers to the larger of the two types of polypeptide chains present in all antibody molecules in their naturally occurring conformations, An "antibody light chain," as used herein, refers to the smaller of the two types of polypeptide chains present in all antibody molecules in their naturally occurring conformations, κ and λ light chains refer to the two major antibody light chain isotypes.

By the term "synthetic antibody" as used herein, is meant an antibody which is generated using recombinant DNA technology, such as, for example, an antibody expressed by a bacteriophage as described herein. The term should also be construed to mean an antibody which has been generated by the synthesis of a DNA molecule encoding the antibody and which DNA molecule expresses an antibody protein, or an amino acid sequence specifying the antibody, wherein the DNA or amino acid sequence has been obtained using synthetic DNA or amino acid sequence technology which is available and well known in the art.

The term "antigen" or "Ag" as used herein is defined as a molecule that provokes an immune response. This immune response may involve either antibody production, or the activation of specific immunologically-competent cells, or both. The skilled artisan will understand that any macromolecule, including virtually all proteins or peptides, can serve as an antigen. Furthermore, antigens can be derived from recombinant or genomic DNA. A skilled artisan will understand that any DNA, which comprises a nucleotide sequences or a partial nucleotide sequence encoding a protein that elicits an immune response therefore encodes an "antigen" as that term is used herein. Furthermore, one skilled in the art will understand that an antigen need not be encoded solely by a full length nucleotide sequence of a gene. It is readily apparent that the present invention includes, but is not limited to, the use of partial nucleotide sequences of more than one gene and that these nucleotide sequences are arranged in various combinations to elicit the desired immune response. Moreover, a skilled artisan will understand that an antigen need not be encoded by a "gene" at all. It is readily apparent that an antigen can be generated synthesized or can be derived from a biological sample. Such a biological sample can include, but is not limited to a tissue sample, a tumor sample, a cell or a biological fluid.

Amino acid as used herein refers to a compound having a free carboxyl group and a free unsubstituted amino group on the a carbon, which may be joined by peptide bonds to form a peptide active agent as described herein. Amino acids may be standard or non-standard, natural or synthetic, with examples (and their abbreviations) including but not limited to:

Asp=D=Aspartic Acid
Ala=A=Alanine
Arg=R=Arginine
Asn=N=Asparagine
Cys=C=Cysteine
Gly=G=Glycine
Glu=E=Glutamic Acid
Gln=Q=Glutamine
His=H=Histidine
Ile=I=Isoleucine
Leu=L=Leucine
Lys=K=Lysine
Met=M=Methionine
Phe=F=Phenylalanine
Pro=P=Proline
Ser=S=Serine
Thr=T=Threonine
Trp=W=Tryptophan
Tyr=Y=Tyrosine
Val=V=Valine
Orn=Ornithine
Nal=2-naphthylalanine
Nva=Norvaline
Nle=Norleucine
Thi=2-thienylalanine
Pcp=4-chlorophenylalanine
Bth=3-benzothienylalanine
Bip=4,4'-biphenylalanine
Tic=tetrahydroisoquinoline-3-carboxylic acid
Aib=aminoisobutyric acid
Anb=α-aminonormalbutyric acid
Dip=2,2-diphenylalanine
Thz=4-Thiazolylalanine All peptide sequences mentioned herein are written according to the usual convention whereby the N-terminal amino acid is on the left and the C-terminal amino acid is on the right. A short line (or no line) between two amino acid residues indicates a peptide bond.

Basic amino acid" refers to any amino acid that is positively charged at a pH of 6.0, including but not limited to R, K, and H.

Aromatic amino acid" refers to any amino acid that has an aromatic group in the side-chain coupled to the alpha carbon, including but not limited to F, Y, W, and H.

Hydrophobic amino acid" refers to any amino acid that has a hydrophobic side chain coupled to the alpha carbon, including but not limited to I, L, V, M, F, W and C, most preferably I, L, and V.

Neutral amino acid" refers to a non-charged amino acid, such as M, F, W, C and A.

As applied to polypeptides, the term "substantial similarity" or "substantially similar" means that two peptide sequences, when optimally aligned, such as by the programs GAP or BESTFIT using default gap weights, share at least 95% sequence identity, even more preferably at least 98% or 99% sequence identity. Preferably, residue positions, which are not identical, differ by conservative amino acid substitutions. A "conservative amino acid substitution" is one in which an amino acid residue is substituted by another amino acid residue having a side chain (R group) with similar chemical properties (e.g., charge or hydrophobicity). In general, a conservative amino acid substitution will not substantially change the functional properties of a protein. In cases where two or more amino acid sequences differ from each other by conservative substitutions, the percent or degree of similarity may be adjusted upwards to correct for the conservative nature of the substitution. Means for making this adjustment are well-known to those of skill in the art. See, e.g., Pearson (1994) *Methods Mol. Biol.* 24: 307-331, herein incorporated by reference. Examples of groups of amino acids that have side chains with similar chemical properties include 1) aliphatic side chains: glycine, alanine, valine, leucine and isoleucine; 2) aliphatic-hydroxyl side chains: serine and threonine; 3) amide-containing side chains: asparagine and glutamine; 4) aromatic side chains: phenylalanine, tyrosine, and tryptophan; 5) basic side chains: lysine, arginine, and histidine; 6) acidic side chains: aspartate and glutamate, and 7) sulfur-containing side chains: cysteine and methionine. Preferred conservative amino acids substitution groups are: valine-leucine-Isoleucine, phenylalanine-tyrosine, lysine-arginine, alanine-valine, glutamate-aspartate, and asparagine-glutamine. Alternatively, a conservative replacement is any change having a positive value in the PAM250 log-likelihood matrix disclosed in Gonnet et al. (1992) *Science* 256: 1443 45, herein incorporated by reference. A "moderately conservative" replacement is any change having a nonnegative value in the PAM250 log-likelihood matrix.

Sequence similarity for polypeptides is typically measured using sequence analysis software. Protein analysis software matches similar sequences using measures of similarity assigned to various substitutions, deletions and other modifications, including conservative amino acid substitutions. For instance, GCG software contains programs such as GAP and BESTFIT which can be used with default parameters to determine sequence homology or sequence identity between closely related polypeptides, such as homologous polypeptides from different species of organisms or between a wild type protein and a mutein thereof. See, e.g., GCG Version 6.1. Polypeptide sequences also can be compared using FASTA with default or recommended parameters; a program in GCG Version 6.1. FASTA (e.g., FASTA2 and FASTA3) provides alignments and percent sequence identity of the regions of the best overlap between the query and search sequences (Pearson (2000) supra). Another preferred algorithm when comparing a sequence of the invention to a database containing a large number of sequences from different organisms is the computer program BLAST, especially BLASTP or TBLASTN, using default parameters. See, e.g., Altschul et al. (1990) *J. Mol. Biol.* 215: 403 410 and Altschul et al. (1997) *Nucleic Acids Res.* 25:3389 402, each of which is herein incorporated by reference in its entirety.

"Therapeutic group" means any suitable therapeutic group, including but not limited to radionuclides, chemotherapeutic agents and cytotoxic agents.

"Radionuclide" as described herein may be any radionuclide suitable for delivering a therapeutic dosage of radiation to a tumor or cancer cell, including but not limited to $^{227}$Ac, $^{211}$At, $^{131}$Ba, $^{77}$Br, $^{109}$Cd, $^{51}$Cr, $^{67}$Cu, $^{165}$Dy, $^{155}$Eu, $^{153}$Gd, $^{198}$Au, $^{166}$Ho, $^{113m}$In, $^{115m}$In, $^{123}$I, $^{125}$I, $^{131}$I, $^{189}$Ir, $^{191}$Ir, $^{192}$Ir, $^{194}$Ir, $^{52}$Fe, $^{55}$Fe, $^{59}$Fe, $^{177}$Lu, $^{109}$Pd, $^{32}$P, $^{226}$Ra, $^{186}$Re, $^{188}$Re, $^{153}$Sm, $^{46}$Sc, $^{47}$Sc, $^{72}$Se, $^{75}$Se, $^{105}$Ag, $^{89}$Sr, $^{35}$S, $^{177}$Ta, $^{117m}$Sn, $^{121}$Sn, $^{166}$Yb, $^{169}$Yb, $^{90}$Y, $^{212}$Bi, $^{119}$Sb, $^{197}$Hg, $^{97}$Ru, $^{100}$Pd, $^{101m}$Rh, and $^{212}$Pb.

"Cytotoxic agent" as used herein includes but is not limited to ricin (or more particularly the ricin A chain), aclacinomycin, diphtheria toxin. Monensin, Verrucarin A, Abrin, *Vinca* alkaloids, Tricothecenes, and *Pseudomonas* exotoxin A.

"Detectable group" as used herein includes any suitable detectable group, such as radiolabels (e.g. $^{35}$S, $^{125}$I, $^{131}$I, etc.), enzyme labels (e.g., horseradish peroxidase, alkaline phosphatase, etc.), fluorescence labels (e.g., fluorescein, green fluorescent protein, etc.), etc., as are well known in the art and used in accordance with known techniques.

Formulations and Administration

For administration in the methods of use described below, the active agent (e.g., the antibody or antigen-binding fragment thereof, cell, nucleic acid molecule and/or vector of this invention) will generally be mixed, prior to administration, with a non-toxic, pharmaceutically acceptable carrier substance (e.g., normal saline or phosphate-buffered saline), and will be administered using any medically appropriate procedure, e.g., parenteral administration (e.g., injection) such as by intravenous or intra-arterial injection.

The active agents described above may be formulated for administration in a pharmaceutical carrier in accordance with known techniques. See, e.g., Remington, *The Science And Practice of Pharmacy* (latest edition). In the manufacture of a pharmaceutical formulation according to the invention, the active compound (including the physiologically acceptable salts thereof) is typically admixed with, inter alia, an acceptable carrier. The carrier must, of course, be acceptable in the sense of being compatible with any other ingredients in the formulation and must not be deleterious to the subject. The carrier may be a liquid and is preferably formulated with the compound as a unit-dose formulation which may contain from 0.01 or 0.5% to 95% or 99% by weight of the active compound. The carrier may be sterile or otherwise free from contaminants that would be undesirable to administer or deliver to a subject.

Formulations of the present invention suitable for parenteral administration comprise sterile aqueous and non-aqueous injection solutions of the active compound, which preparations are preferably isotonic with the blood of the intended subject. These preparations may contain anti-oxidants, buffers, bacteriostats and solutes which render the formulation isotonic with the blood of the intended subject.

The active agents may be administered by any medically appropriate procedure, e.g., normal intravenous or intra-arterial administration. In certain cases, direct administration to a tumor and/or a body cavity, orifice and/or tissue containing a tumor may be desired.

Active agents may be provided in lyophylized form in a sterile aseptic container or may be provided in a pharmaceutical formulation in combination with a pharmaceutically acceptable carrier, such as sterile pyrogen-free water or sterile pyrogen-free physiological saline solution.

CAR-modified T cells of this invention may also serve as a type of vaccine for ex vivo immunization and/or in vivo therapy in a subject of this invention.

In some embodiments involving ex vivo immunization, at least one of the following occurs in vitro prior to administering the cell into a subject: i) expansion of the cells, ii) introducing a nucleic acid encoding a CAR of this invention to the cells, and/or iii) cryopreservation of the cells.

Ex vivo procedures are well known in the art and are discussed more fully below. Briefly, cells are isolated from a mammal (preferably a human) and genetically modified (i.e., transduced or transfected in vitro) with a vector expressing a CAR of this invention. The resulting CAR-modified cell can be administered to a subject of this invention to provide a therapeutic benefit. In some embodiments, the subject can be a human and the CAR-modified cell can be autologous with respect to the subject who is the recipient of the CAR-modified cells. Alternatively, the cells can be allogeneic, syngeneic or xenogeneic with respect to the subject who is the recipient of the CAR-modified cells.

In addition to using a cell-based vaccine for ex vivo immunization, the present invention also provides compositions and methods for in vivo immunization to elicit and/or enhance an immune response directed against an antigen in a subject of this invention.

Generally, the cells activated and expanded as described herein can be used in the treatment and/or prevention of diseases and/or disorders that arise in subjects; e.g., subjects who are immunocompromised or at risking of becoming immunocompromised.

CAR-modified T cells of the present invention may be administered either alone, or as a pharmaceutical composition in combination with diluents and/or with other components such as IL-2 and/or other cytokines and/or cell populations. Briefly, pharmaceutical compositions of the present invention may comprise a target cell population as described herein, in combination with one or more pharmaceutically or physiologically acceptable carriers, diluents or excipients. Such compositions may comprise buffers such as neutral buffered saline, phosphate buffered saline, sterile saline and the like; carbohydrates such as glucose, mannose, sucrose or dextrans, mannitol; proteins; polypeptides or amino acids such as glycine; antioxidants; chelating agents such as EDTA and/or glutathione; adjuvants (e.g., aluminum hydroxide) and/or preservatives, singly or in any combination.

Pharmaceutical compositions of the present invention can be administered in a manner appropriate to the disease to be treated and/or prevented. The quantity and frequency of administration will be determined by such factors as the condition of the subject, as well as the type and severity of the subject's disease, although in some embodiments, appropriate dosages may be determined by clinical trials.

When "an immunologically effective amount," "an antitumor effective amount," "a tumor-inhibiting effective amount," or a "therapeutic amount" is indicated, the precise amount of the compositions of the present invention to be administered can be determined by a physician with consideration of individual differences in age, weight, tumor size, extent of infection or metastasis, and condition of the patient (subject). In some embodiments, a pharmaceutical composition comprising cells of this invention can be administered at a dosage of about $10^3$ to about $10^{10}$ cells/kg body weight, and in some embodiments, the dosage can be from about $10^5$ to about $10^6$ cells/kg body weight, including all integer values (e.g., $10^4$, $10^5$, $10^6$, $10^7$, $10^8$, $10^9$) within those ranges.

The cell compositions of this invention can also be administered multiple times (e.g., hourly, four times daily, three times daily, two times daily, daily, twice weekly, three times weekly, weekly, monthly, bi-monthly, semi-annually, annually, etc.) at these dosages.

The cells of this invention can be administered by using infusion techniques that are commonly known in immunotherapy (see, e.g., Rosenberg et al. *New Eng. J. of Med.* 319:1676 (1988)). The optimal dosage and treatment regimen for a particular subject can readily be determined by one skilled in the art of medicine by monitoring the subject for signs of disease and adjusting the treatment accordingly.

In some embodiments, it may be desirable to administer activated T cells to a subject and then subsequently redraw blood (or have an apheresis performed), activate T cells therefrom as described herein, and reinfuse the subject with these activated and expanded T cells. This process can be carried out multiple times, e.g., weekly or every few weeks. In certain embodiments, T cells can be activated from blood draws of from about 10 cc to about 400 cc. In certain embodiments, T cells are activated from blood draws of 20 cc, 30 cc, 40 cc, 50 cc, 60 cc, 70 cc, 80 cc, 90 cc, or 100 cc. Not to be bound by theory, using this multiple blood draw/multiple reinfusion protocol may serve to select out certain populations of T cells.

Administration of the compositions of this invention can be carried out in any manner, including by aerosol inhalation, injection, ingestion, transfusion, implantation and/or transplantation. The compositions of this invention can be administered to a patient subcutaneously, intradermally, intratumorally, intranodally, intramedullary, intramuscularly, by intravenous (i.v.) injection, and/or intraperitoneally. In some embodiments, the T cell compositions of the present invention can be administered to a subject by intradermal or subcutaneous injection. In another embodiment, the T cell compositions of the present invention can be administered by i.v. injection. In some embodiments, the compositions of T cells can be injected directly into a tumor, lymph node and/or site of infection.

In some embodiments of the present invention, cells activated and expanded using the methods described herein, or other methods known in the art where T cells are expanded to therapeutic levels, can be administered to a subject in conjunction with (e.g., before, concurrently and/or following) any number of relevant treatment modalities, In some embodiments, the T cells of the invention may be used in combination with chemotherapy, radiation, immunosuppressive agents, such as cyclosporin, azathioprine, methotrexate, mycophenolate, and FK506, antibodies, or other immunoablative agents such as CAM PATH, anti-CD3 antibodies or other antibody therapies, cytotoxin, fludaribine, cyclosporin, FK506, rapamycin, mycophenolic acid, steroids, FR901228, cytokines, and/o irradiation.

In some embodiments, the cell compositions of the present invention can be administered to a patient in conjunction with (e.g., before, concurrently and/or following) bone marrow transplantation, T cell ablative therapy using either chemotherapy agents such as fludarabine, external-beam radiation therapy (XRT), cyclophosphamide, or antibodies such as OKT3 or CAMPATH. In another embodiment, the cell compositions of the present invention can be administered following B-cell ablative therapy such as agents that react with CD20, e.g., Rituxan. For example, in one embodiment, subjects may undergo standard treatment with high dose chemotherapy followed by peripheral blood stem cell transplantation. In certain embodiments, following the transplant, subjects can receive an infusion of the expanded immune cells of the present invention. In an additional embodiment, expanded cells can be administered before and/or following surgery.

In the treatment of cancers or tumors the CARs and/or nucleic acid molecules encoding CARs of the present invention may optionally be administered in conjunction with other, different, cytotoxic agents such as chemotherapeutic or antineoplastic compounds or radiation therapy useful in the treatment of the disorders or conditions described herein (e.g., chemotherapeutics or antineoplastic compounds). The other compounds may be administered prior to, concurrently and/or after administration of the antibodies or antigen binding fragments thereof of this invention. As used herein, the word "concurrently" means sufficiently close in time to produce a combined effect (that is, concurrently may be simultaneously, or it may be two or more administrations occurring before or after each other)

As used herein, the phrase "radiation therapy" includes, but is not limited to, x-rays or gamma rays which are delivered from either an externally applied source such as a beam or by implantation of small radioactive sources.

Nonlimiting examples of suitable chemotherapeutic agents which may be administered with the antibodies or antigen binding fragments, cells, nucleic acid molecules and/or vectors as described herein include daunomycin, cisplatin, verapamil, cytosine arabinoside, aminopterin, democolcine, tamoxifen, Actinomycin D, Alkylating agents (including, without limitation, nitrogen mustards, ethylenimine derivatives, alkyl sulfonates, nitrosoureas and triazenes): Uracil mustard, Chlormethine, Cyclophosphamide (Cytoxan®), Ifosfamide, Melphalan, Chlorambucil, Pipobroman. Triethylene-melamine, Triethylenethiophosphoramine, Busulfan, Carmustine, Lomustine, Streptozocin, Dacarbazine, and Temozolomide; Antimetabolites (including, without limitation, folic acid antagonists, pyrimidine analogs, purine analogs and adenosine deaminase inhibitors): Methotrexate, 5-Fluorouracil, Floxuridine, Cytarabine, 6-Mercaptopurine, 6-Thioguanine, Fludarabine phosphate, Pentostatine, and Gemcitabine, Natural products and their derivatives (for example, vinca alkaloids, antitumor antibiotics, enzymes, lymphokines and epipodophyllotoxins): Vinblastine, Vincristine, Vindesine, Bleomycin, Dactinomycin, Daunorubicin, Doxorubicin, Epirubicin, Idarubicin, Ara-C, paclitaxel (paclitaxel is commercially available as Taxol R), Mithramycin, Deoxyco-formycin, Mitomycin-C, L-Asparaginase, Interferons (especially IFN-a), Etoposide, and Teniposide; Other anti-proliferative cytotoxic agents are navelbene, CPT-11, anastrazole, letrazole, capecitabine, reloxafine, cyclophosphamide, ifosamide, and droloxafine. Additional anti-proliferative cytotoxic agents include, but are not limited to, melphalan, hexamethyl melamine, thiotepa, cytarabin, idatrexate, trimetrexate, dacarbazine, L-asparaginase, camptothecin, topotecan, bicalutamide, flutamide, leuprolide, pyridobenzoindole derivatives, interferons, and interleukins. Preferred classes of antiproliferative cytotoxic agents are the EGFR inhibitors, Her-2 inhibitors, CDK inhibitors, and Herceptin® (trastuzumab). (see, e.g., U.S. Pat. Nos. 6,537,988; 6,420,377). Such compounds may be given in accordance with techniques currently known for the administration thereof.

Antibodies of the invention include antibodies that are modified, i.e., by the covalent attachment of any type of molecule to the antibody such that covalent attachment does not prevent the antibody from specifically binding to its binding site. For example, antibodies of the invention may be modified, e.g., by glycosylation, acetylation, pegylation, phosphorylation, amidation, or with other protecting/blocking groups, proteolytic cleavage, linkage to a cellular ligand or other protein, etc. Any of numerous chemical modifications may be carried out by known techniques, including but not limited to specific chemical cleavage, acetylation, formylation, metabolic synthesis of tunicamycin, etc. Additionally, the antibodies may contain one or more non-classical amino acids.

Monoclonal antibodies can be prepared using a wide variety of techniques including the use of hybridoma, recombinant, and phage display technologies, or a combination thereof. For example, monoclonal antibodies can be produced using hybridoma techniques including those taught, for example, in Harlow et al., *Antibodies: A Laboratory Manual*, (Cold Spring Harbor Laboratory Press, 2nd ed. 1988); and Hammerling et al., *Monoclonal Antibodies and T-Cell Hybridomas* 563-681 (Elsevier, N.Y., 1981). The term "monoclonal antibody" as used herein is not limited to antibodies produced through hybridoma technology. The term "monoclonal antibody" refers to an antibody that is derived from a single clone, including any eukaryotic, prokaryotic, or phage clone, and not the method by which it is produced.

Methods for producing and screening for specific antibodies using hybridoma technology are routine and known. Briefly, mice are immunized with an antigen or a cell expressing such antigen. Once an immune response is detected, e.g., antibodies specific for the antigen are detected in the mouse serum, the mouse spleen is harvested and splenocytes isolated. The splenocytes are then fused by known techniques to any suitable myeloma cells, for example cells from cell line SP20 available from the ATCC. Hybridomas are selected and cloned by limited dilution. The hybridoma clones are then assayed by methods known in the art for cells that secrete antibodies capable of binding a polypeptide or antigen of the invention. Ascites fluid, which generally contains high levels of antibodies, can be generated by immunizing mice with positive hybridoma clones.

Examples of techniques which can be used to produce single-chain Fvs (scFv) and antibodies include those described in U.S. Pat. Nos. 4,946,778 and 5,258,498; Huston et al. *Methods in Enzymology* 203:46-88 (1991); Shu et al. *PNAS* 90:7995-7999 (1993); and Skerra et al. *Science* 240: 1038-1040 (1988).

The term "humanized" as used herein refers to antibodies from non-human species whose amino acid sequences have been modified to increase their similarity to antibody variants produced naturally in humans. Thus, humanized antibodies are antibody molecules from a non-human species antibody that binds the desired antigen, having one or more complementarity determining regions (CDRs) from the non-human species and framework regions from a human immunoglobulin molecule. Often, framework residues in the human framework regions will be substituted with the corresponding residue from the donor antibody to alter, preferably to improve, antigen binding and/or reduce immunogenicity of the humanized antibody in a subject. These framework substitutions are identified by methods well known in the art. e.g., by modeling of the interactions of the CDR and framework residues to identify framework residues important for antigen binding and/or immunogenicity and sequence comparison to identify unusual framework residues at particular positions. (See, e.g., Queen et al. U.S. Pat. No. 5,585,089; Riechmann et al. *Nature* 332:323 (1988), which are incorporated herein by reference in their entireties.) Antibodies can be humanized using a variety of techniques known in the art including, for example, CDR-grafting (see, e.g., U.S. Pat. Nos. 5,225,539; 5,530,101; and 5,585,089), veneering or resurfacing (see, e.g., EP U.S. Pat. No. 592,106; EP U.S. Pat. No. 519,596; Padlan, *Molecular Immunology* 28 (4/5):489-498 (1991); Studnicka et al. *Protein Engineering* 7 (6):805-814 (1994); Roguska. et al. *PNAS* 91:969-973 (1994)), and chain shuffling (U.S. Pat. No. 5,565,332). A detailed description of the production and characterization of the humanized monoclonal antibodies of the present invention is provided in the Examples section herein.

Completely human antibodies are desirable for therapeutic treatment, diagnosis, and/or detection of human subjects. Human antibodies can be made by a variety of methods known in the art including phage display methods described above using antibody libraries derived from human immunoglobulin sequences. See. e.g., U.S. Pat. Nos. 4,444,887 and 4,716,111.

Human antibodies can also be produced using transgenic mice which are incapable of expressing functional endogenous immunoglobulins, but which can express human immunoglobulin genes. For example, the human heavy and light chain immunoglobulin gene complexes may be introduced randomly or by homologous recombination into mouse embryonic stem cells. Alternatively, the human variable region, constant region, and diversity region may be introduced into mouse embryonic stem cells in addition to the human heavy and light chain genes. The mouse heavy and light chain immunoglobulin genes may be rendered non-functional separately or simultaneously with the introduction of human immunoglobulin loci by homologous recombination. In particular, homozygous deletion of the JH region prevents endogenous antibody production. The modified embryonic stem cells are expanded and microinjected into blastocysts to produce chimeric mice. The chimeric mice are then bred to produce homozygous offspring that express human antibodies. The transgenic mice are immunized in the normal fashion with a selected antigen, e.g., all or a portion of a polypeptide of the invention. Monoclonal antibodies directed against the antigen can be obtained from the immunized, transgenic mice using conventional hybridoma technology. The human immunoglobulin transgenes harbored by the transgenic mice rearrange during B cell differentiation, and subsequently undergo class switching and somatic mutation. Thus, using such a technique, it is possible to produce therapeutically useful IgG, IgA, IgM and IgE antibodies. For an overview of this technology for producing human antibodies, see Lonberg and Huszar (*Int. Rev. Immunol.* 13:65-93 (1995)). For a detailed discussion of this technology for producing human antibodies and human monoclonal antibodies and protocols for producing such antibodies, see, e.g., U.S. Pat. Nos. 5,413,923; 5,625,126; 5,633,425; 5,569,825; 5,661,016; 5,545,806; 5,814,318 and 5,939,598.

Completely human antibodies which recognize a selected epitope can be generated using a technique referred to as "guided selection." In this approach a selected non-human monoclonal antibody, e.g., a mouse antibody, is used to guide the selection of a completely human antibody recognizing the same epitope. (Jespers et al. *Bio/technology* 12:899-903 (1988)).

Further, antibodies to the polypeptides of the invention can, in turn, be utilized to generate anti-idiotype antibodies that "mimic" polypeptides of the invention using techniques well known to those skilled in the art. (See, e.g., Greenspan & Bona, *FASEB J.* 7 (5):437-444; (1989) and Nissinoff, *J. Immunol.* 147 (8):2429-2438 (1991)). For example antibodies which bind to and competitively inhibit polypeptide multimerization and/or binding of a polypeptide of the invention to a ligand can be used to generate anti-idiotypes that "mimic" the polypeptide multimerization and/or binding domain and, as a consequence, bind to and neutralize polypeptide and/or its ligand. Such neutralizing anti-idiotypes or Fab fragments of such anti-idiotypes can be used in therapeutic regimens to neutralize polypeptide ligand. For example, such anti-idiotypic antibodies can be used to bind a polypeptide of the invention and/or to bind its ligands/receptors, and thereby block its biological activity.

The invention further provides polynucleotides comprising a nucleotide sequence encoding a chimeric antigen receptor of the invention as described above. The polynucleotides may be obtained, and the nucleotide sequence of the polynucleotides determined, by any method known in the art. For example, if the nucleotide sequence of the components of the chimeric antigen receptor are known, a polynucleotide encoding the components may be assembled from chemically synthesized oligonucleotides, which involves the synthesis of overlapping oligonucleotides containing portions of the sequence encoding the components of the chimeric antigen receptor, annealing and ligation of those oligonucleotides, and then amplification of the ligated oligonucleotides by polymerase chain reaction (PCR). Alternatively, a polynucleotide encoding a chimeric antigen receptor may be generated from nucleic acid from a suitable source. Amplified nucleic acids generated by PCR may then be cloned into replicable cloning vectors using any method well known in the art.

All publications, patent applications, patents, patent publications and other references cited herein are incorporated by reference in their entireties for the teachings relevant to the sentence and/or paragraph in which the reference is presented.

SEQUENCES

UNC 763.74 scFv (Vk2.Vh1)
(SEQ ID NO: 5)
AM EFGL SWL FLV AILK GVQ CDI LLTQ SPA ILS

VTPG ETV SLS CRAS QTI YKN LHWY QQK SHR SPRL

LIK YGS DSIS GIP SRF TGSG SGT DYT LNIN SVK

PED EGIY YCL QGY STPW TFG GGT KLEI KGG GGS

GGGG SGG GGQ IQLV QSG PEL KKPG ETV KIS CKAS

GYT FTD YSMH WVK KTP GKGL KWL GWI NTAT GEP

TYA DDFK GRF AIS LETS ART VYL QINN LRN EDT

ATYF CFS YYD YWGQ GTT LTV SSTR C

UNC763.74 scFv (Vh1.Vk2)
(SEQ ID NO: 6)
AM EFGL SWL FLV AILK GVQ CQI QLVQ SGP ELK

KPGE TVK ISC KASG YTF TDY SMHW VKK TPG KGLK

WLG WIN TATG EPT YAD DFKG RFA ISL ETSA RTV

YLQ INNL RNE DTA TYFC FSY YDY WGQG TTL TVS

SGGG GSG GGG SGGG GDI LLT QSPA ILS VTP GETV

SLS CRA SQTI YKN LHW YQQK SHR SPR LLIK YGS

DSI SGIP SRF TGS GSGT DYT LNI NSVK PED EGI

YYCL QGY STP WTFG GGT KLE IKTR C 225.28 scFv (Vh1.Vk)
(SEQ ID NO: 7)
AM EFGL SWL FLV AILK GVQ CKV KLQE SGG GLV

QPGG SMK LSC VVSG FTF SNY WMNW VRQ SPE KGLE

WIA EIR LKSN NFA RYY AESV KGR FTI SRDD SKS

SVY LQMI NLR AED TGIY YCT SYG NYVG HYF DHW

GQGT TLT VSS GGGG SGG GGS GGGG DIV MTQ SQKF

MST SVG DRVS VTC KAS QNVD TNV AWY QQKP GQS

PEP LLFS ASY RYT GVPD RFT GSG SGTD FTL TIS

NVQS EDL AEY FCQQ YNS YPL TFGG GTK LVI KTRC 225.28 scFv (Vk.Vh1)
(SEQ ID NO: 8)
AM EFGL SWL FLV AILK GVQ CDI VMTQ SQK FMS

TSVG DRV SVT CKAS QNV DTN VAWY QQK PGQ SPEP

LLF SAS YRYT GVP DRF TGSG SGT DFT LTIS NVQ

SED LAEY FCQ QYN SYPL TFG GGT KLVI KGG GGS

GGGG SGG GGK VKLQ ESG GGL VQPG GSM KLS CVVS

GFT FSN YWMN WVR QSP EKGL EWI AEI RLKS NNF

ARY YAES VKG RFT ISRD DSK SSV YLQM INL RAE

DTGI YYC TSY GNYV GHY FDH WGQG TTL TVS STRC

SEQUENCES

UNC Protein 763.74 Vh1
(SEQ ID NO: 1)
QIQLVQSGPELKKPGETVKISCKASGYTFTDYSMHWVKKTPGKGLKWLG
WINTATGEPTYADDFKGRFAISLETSARTVYLQINNLRNEDTATYFCFS
YYDYWGQGTTLTVSS UNC Protein 763.74 Vk2
(SEQ ID NO: 2)
DILLTQSPAILSVTPGETVSLSCRASQTIYKNLHWYQQKSHRSPRLLIK
YGSDSISGIPSRFTGSGSGTDYTLNINSVKPEDEGIYYCLQGYSTPWTF
GGGTKLEIK Protein 225.28 Vh1
(SEQ ID NO: 3)
KVKLQESGGGLVQPGGSMKLSCVVSGFTFSNYWMNWVRQSPEKGLEWIA
EIRLKSNNFARYYAESVKGRFTISRDDSKSSVYLQMINLRAEDTGIYYC
TSYGNYVGHYFDHWGQGTTLTVSS Protein 225.28 Vk
(SEQ ID NO: 4)
DIVMTQSQKFMSTSVGDRVSVTCKASQNVDTNVAWYQQKPGQSPEPLLF
SASYRYTGVPDRFTGSGSGTDFTLTISNVQSEDLAEYFCQQYNSYPLTF
GGGTKLVIK scFv225.28 VH1.VK
(SEQ ID NO: 11)
TAGCCATGGAATTCGGCCTGAGCTGGCTGTTCCTGGTGGCCATCCTGAA

GGGCGTGCAGTGCAAGGTGAAGCTGCAGGAGTCTGGAGGAGGCTTGGTG

CAACCTGGAGGATCCATGAAACTCTCCTGTGTTGTCTCTGGATTCACTT

TCAGTAATTACTGGATGAACTGGGTCCGCCAGTCTCCAGAGAAGGGGCT

TGAGTGGATTGCAGAAATTAGATTGAAATCCAATAATTTTGCAAGATAT

TATGCGGAGTCTGTGAAAGGGAGGTTCACCATCTCAAGAGATGATTCCA

AAAGTAGTGTCTACCTGCAAATGATCAACCTAAGAGCTGAAGATACTGG

CATTTATTACTGTACCAGTTATGGTAACTACGTTGGGCACTATTTTGAC

CACTGGGGCCAAGGCACCACTCTCACAGTCTCCTCAGGTGGGGCGGTT

CAGGCGGAGGTGGCTCTGGCGGTGGCGGAGACATTGTGATGACCCAGTC

TCAAAAATTCATGTCCACATCAGTAGGAGACAGGGTCAGCGTCACCTGC

AAGGCCAGTCAGAATGTGGATACTAATGTAGCCTGGTATCAACAAAAAC

CAGGGCAATCTCCTGAACCACTGCTTTTCTCGGCATCCTACCGTTACAC

TGGAGTCCCTGATCGCTTCACAGGCAGTGGATCTGGGACAGATTTCACT

CTCACCATCAGCAATGTGCAGTCTGAAGACTTGGCAGAGTATTTCTGTC

AGCAATATAACAGCTATCCTCTGACGTTCGGTGGAGGCACCAAGCTGGT

GATCAAAACGCGTTGC scFv225.28 VK.VH1
(SEQ ID NO: 12)
TAGCCATGGAATTCGGCCTGAGCTGGCTGTTCCTGGTGGCCATCCTGAA

GGGCGTGCAGTGCGACATTGTGATGACCCAGTCTCAAAAATTCATGTCC

ACATCAGTAGGAGACAGGGTCAGCGTCACCTGCAAGGCCAGTCAGAATG

TGGATACTAATGTAGCCTGGTATCAACAAAAACCAGGGCAATCTCCTGA

ACCACTGCTTTTCTCGGCATCCTACCGTTACACTGGAGTCCCTGATCGC

TTCACAGGCAGTGGATCTGGGACAGATTTCACTCTCACCATCAGCAATG

TGCAGTCTGAAGACTTGGCAGAGTATTTCTGTCAGCAATATAACAGCTA

TCCTCTGACGTTCGGTGGAGGCACCAAGCTGGTGATCAAAGGTGGGGGC

GGTTCAGGCGGAGGTGGCTCTGGCGGTGGCGGAAAGGTGAAGCTGCAGG

AGTCTGGAGGAGGCTTGGTGCAACCTGGAGGATCCATGAAACTCTCCTG

TGTTGTCTCTGGATTCACTTTCAGTAATTACTGGATGAACTGGGTCCGC

CAGTCTCCAGAGAAGGGGCTTGAGTGGATTGCAGAAATTAGATTGAAAT

CCAATAATTTTGCAAGATATTATGCGGAGTCTGTGAAAGGGAGGTTCAC

CATCTCAAGAGATGATTCCAAAAGTAGTGTCTACCTGCAAATGATCAAC

CTAAGAGCTGAAGATACTGGCATTTATTACTGTACCAGTTATGGTAACT

ACGTTGGGCACTATTTTGACCACTGGGGCCAAGGCACCACTCTCACAGT

CTCCTCAACGCGTTGC scFv.763.74 VH1.VK2
(SEQ ID NO: 10)
TAGCCATGGAATTCGGCCTGAGCTGGCTGTTCCTGGTGGCCATCCTGAA

GGGCGTGCAGTGCCAGATCCAGTTGGTGCAGTCTGGACCTGAGCTGAAG

AAGCCTGGAGAGACAGTCAAGATCTCCTGCAAGGCTTCTGGTTATACCT

TCACAGACTATTCAATGCACTGGGTGAAGAAGACTCCAGGAAAGGGTTT

AAAGTGGCTGGGCTGGATAAACACTGCGACTGGTGAGCCAACATATGCA

GATGACTTCAAGGGACGGTTTGCCATCTCTTTGGAAACCTCTGCCAGGA

CTGTCTATTTGCAGATCAATAATCTCAGAAATGAGGACACGGCTACATA

TTTCTGTTTTAGTTACTACGACTACTGGGGCCAAGGCACCACTCTCACA

GTTTCCTCAGGTGGGGCGGTTCAGGCGGAGGTGGCTCTGGCGGTGGCG

GAGATATCCTGCTCACCCAGTCTCCAGCAATCCTGTCTGTGACTCCAGG

AGAAACAGTCAGTCTTTCCTGTAGGGCCAGCCAGACTATTTACAAGAAC

TACACTGGTATCAACAGAAATCACATCGGTCTCCAAGGCTTCTCATCA

AGTATGGTTCTGATTCCATCTCTGGGATCCCCTCCAGGTTCACTGGCAG

TGGATCAGGGACAGATTACACTCTCAATATCAACAGTGTGAAGCCCGAA

GATGAAGGAATATATTACTGTCTTCAAGGTTACAGTACCCTTGGACGT

TCGGTGGAGGCACCAAGCTGGAAATCAAAACGCGTTGC scFv.763.74 VK2.VH1
(SEQ ID NO: 9)
TAGCCATGGAATTCGGCCTGAGCTGGCTGTTCCTGGTGGCCATCCTGAA

GGGCGTGCAGTGCGATATCCTGCTCACCCAGTCTCCAGCAATCCTGTCT

GTGACTCCAGGAGAAACAGTCAGTCTTTCCTGTAGGGCCAGCCAGACTA

TTTACAAGAACCTACACTGGTATCAACAGAAATCACATCGGTCTCCAAG

GCTTCTCATCAAGTATGGTTCTGATTCCATCTCTGGGATCCCCTCCAGG

TTCACTGGCAGTGGATCAGGGACAGATTACACTCTCAATATCAACAGTG

TGAAGCCCGAAGATGAAGGAATATATTACTGTCTTCAAGGTTACAGTAC

SEQUENCES

ACCTTGGACGTTCGGTGGAGGCACCAAGCTGGAAATCAAAGGTGGGGGC

GGTTCAGGCGGAGGTGGCTCTGGCGGTGGCGGACAGATCCAGTTGGTGC

AGTCTGGACCTGAGCTGAAGAAGCCTGGAGAGACAGTCAAGATCTCCTG

CAAGGCTTCTGGTTATACCTTCACAGACTATTCAATGCACTGGGTGAAG

AAGACTCCAGGAAAGGGTTTAAAGTGGCTGGGCTGGATAAACACTGCGA

CTGGTGAGCCAACATATGCAGATGACTTCAAGGGACGGTTTGCCATCTC

TTTGGAAACCTCTGCCAGGACTGTCTATTTGCAGATCAATAATCTCAGA

AATGAGGACACGGCTACATATTTCTGTTTTAGTTACTACGACTACTGGG

GCCAAGGCACCACTCTCACAGTTTCCTCAACGCGTTGC

SEQUENCE LISTING

<160> NUMBER OF SEQ ID NOS: 13

<210> SEQ ID NO 1
<211> LENGTH: 113
<212> TYPE: PRT
<213> ORGANISM: Artificial
<220> FEATURE:
<223> OTHER INFORMATION: UNC 763.74 Vh1

<400> SEQUENCE: 1

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Asp Tyr
                20                  25                  30

Ser Met His Trp Val Lys Lys Thr Pro Gly Lys Gly Leu Lys Trp Leu
            35                  40                  45

Gly Trp Ile Asn Thr Ala Thr Gly Glu Pro Thr Tyr Ala Asp Asp Phe
    50                  55                  60

Lys Gly Arg Phe Ala Ile Ser Leu Glu Thr Ser Ala Arg Thr Val Tyr
65                  70                  75                  80

Leu Gln Ile Asn Asn Leu Arg Asn Glu Asp Thr Ala Thr Tyr Phe Cys
                85                  90                  95

Phe Ser Tyr Tyr Asp Tyr Trp Gly Gln Gly Thr Thr Leu Thr Val Ser
            100                 105                 110

Ser

<210> SEQ ID NO 2
<211> LENGTH: 107
<212> TYPE: PRT
<213> ORGANISM: Artificial
<220> FEATURE:
<223> OTHER INFORMATION: UNC 763.74 Vk2

<400> SEQUENCE: 2

Asp Ile Leu Leu Thr Gln Ser Pro Ala Ile Leu Ser Val Thr Pro Gly
1               5                   10                  15

Glu Thr Val Ser Leu Ser Cys Arg Ala Ser Gln Thr Ile Tyr Lys Asn
                20                  25                  30

Leu His Trp Tyr Gln Gln Lys Ser His Arg Ser Pro Arg Leu Leu Ile
            35                  40                  45

Lys Tyr Gly Ser Asp Ser Ile Ser Gly Ile Pro Ser Arg Phe Thr Gly
    50                  55                  60

Ser Gly Ser Gly Thr Asp Tyr Thr Leu Asn Ile Asn Ser Val Lys Pro
65                  70                  75                  80

Glu Asp Glu Gly Ile Tyr Tyr Cys Leu Gln Gly Tyr Ser Thr Pro Trp
                85                  90                  95

Thr Phe Gly Gly Gly Thr Lys Leu Glu Ile Lys
            100                 105

<210> SEQ ID NO 3
<211> LENGTH: 122
<212> TYPE: PRT
<213> ORGANISM: Artificial
<220> FEATURE:
<223> OTHER INFORMATION: 225.28 Vh1

<400> SEQUENCE: 3

Lys Val Lys Leu Gln Glu Ser Gly Gly Leu Val Gln Pro Gly Gly
1               5                   10                  15

Ser Met Lys Leu Ser Cys Val Val Ser Gly Phe Thr Phe Ser Asn Tyr
            20                  25                  30

Trp Met Asn Trp Val Arg Gln Ser Pro Glu Lys Gly Leu Glu Trp Ile
        35                  40                  45

Ala Glu Ile Arg Leu Lys Ser Asn Asn Phe Ala Arg Tyr Tyr Ala Glu
    50                  55                  60

Ser Val Lys Gly Arg Phe Thr Ile Ser Arg Asp Asp Ser Lys Ser Ser
65                  70                  75                  80

Val Tyr Leu Gln Met Ile Asn Leu Arg Ala Glu Asp Thr Gly Ile Tyr
                85                  90                  95

Tyr Cys Thr Ser Tyr Gly Asn Tyr Val Gly His Tyr Phe Asp His Trp
            100                 105                 110

Gly Gln Gly Thr Thr Leu Thr Val Ser Ser
        115                 120

<210> SEQ ID NO 4
<211> LENGTH: 107
<212> TYPE: PRT
<213> ORGANISM: Artificial
<220> FEATURE:
<223> OTHER INFORMATION: 225.28 Vk

<400> SEQUENCE: 4

Asp Ile Val Met Thr Gln Ser Gln Lys Phe Met Ser Thr Ser Val Gly
1               5                   10                  15

Asp Arg Val Ser Val Thr Cys Lys Ala Ser Gln Asn Val Asp Thr Asn
            20                  25                  30

Val Ala Trp Tyr Gln Gln Lys Pro Gly Gln Ser Pro Glu Pro Leu Leu
        35                  40                  45

Phe Ser Ala Ser Tyr Arg Tyr Thr Gly Val Pro Asp Arg Phe Thr Gly
    50                  55                  60

Ser Gly Ser Gly Thr Asp Phe Thr Leu Thr Ile Ser Asn Val Gln Ser
65                  70                  75                  80

Glu Asp Leu Ala Glu Tyr Phe Cys Gln Gln Tyr Asn Ser Tyr Pro Leu
                85                  90                  95

Thr Phe Gly Gly Gly Thr Lys Leu Val Ile Lys
            100                 105

<210> SEQ ID NO 5
<211> LENGTH: 257
<212> TYPE: PRT
<213> ORGANISM: Artificial
<220> FEATURE:
<223> OTHER INFORMATION: UNC 763.74 scFv (Vk2.Vh1)

<400> SEQUENCE: 5

```
Ala Met Glu Phe Gly Leu Ser Trp Leu Phe Leu Val Ala Ile Leu Lys
1               5                   10                  15

Gly Val Gln Cys Asp Ile Leu Leu Thr Gln Ser Pro Ala Ile Leu Ser
                20                  25                  30

Val Thr Pro Gly Glu Thr Val Ser Leu Ser Cys Arg Ala Ser Gln Thr
            35                  40                  45

Ile Tyr Lys Asn Leu His Trp Tyr Gln Gln Lys Ser His Arg Ser Pro
50                  55                  60

Arg Leu Leu Ile Lys Tyr Gly Ser Asp Ser Ile Ser Gly Ile Pro Ser
65                  70                  75                  80

Arg Phe Thr Gly Ser Gly Ser Gly Thr Asp Tyr Thr Leu Asn Ile Asn
                85                  90                  95

Ser Val Lys Pro Glu Asp Glu Gly Ile Tyr Tyr Cys Leu Gln Gly Tyr
                100                 105                 110

Ser Thr Pro Trp Thr Phe Gly Gly Gly Thr Lys Leu Glu Ile Lys Gly
            115                 120                 125

Gly Gly Gly Ser Gly Gly Gly Gly Ser Gly Gly Gly Gln Ile Gln
        130                 135                 140

Leu Val Gln Ser Gly Pro Glu Leu Lys Lys Pro Gly Glu Thr Val Lys
145                 150                 155                 160

Ile Ser Cys Lys Ala Ser Gly Tyr Thr Phe Thr Asp Tyr Ser Met His
                165                 170                 175

Trp Val Lys Lys Thr Pro Gly Lys Gly Leu Lys Trp Leu Gly Trp Ile
                180                 185                 190

Asn Thr Ala Thr Gly Glu Pro Thr Tyr Ala Asp Asp Phe Lys Gly Arg
                195                 200                 205

Phe Ala Ile Ser Leu Glu Thr Ser Ala Arg Thr Val Tyr Leu Gln Ile
210                 215                 220

Asn Asn Leu Arg Asn Glu Asp Thr Ala Thr Tyr Phe Cys Phe Ser Tyr
225                 230                 235                 240

Tyr Asp Tyr Trp Gly Gln Gly Thr Thr Leu Thr Val Ser Ser Thr Arg
                245                 250                 255

Cys

<210> SEQ ID NO 6
<211> LENGTH: 257
<212> TYPE: PRT
<213> ORGANISM: Artificial
<220> FEATURE:
<223> OTHER INFORMATION: UNC763.74 scFv (Vh1.Vk2)

<400> SEQUENCE: 6

Ala Met Glu Phe Gly Leu Ser Trp Leu Phe Leu Val Ala Ile Leu Lys
1               5                   10                  15

Gly Val Gln Cys Gln Ile Gln Leu Val Gln Ser Gly Pro Glu Leu Lys
                20                  25                  30

Lys Pro Gly Glu Thr Val Lys Ile Ser Cys Lys Ala Ser Gly Tyr Thr
            35                  40                  45

Phe Thr Asp Tyr Ser Met His Trp Val Lys Lys Thr Pro Gly Lys Gly
50                  55                  60

Leu Lys Trp Leu Gly Trp Ile Asn Thr Ala Thr Gly Glu Pro Thr Tyr
65                  70                  75                  80

Ala Asp Asp Phe Lys Gly Arg Phe Ala Ile Ser Leu Glu Thr Ser Ala
                85                  90                  95

Arg Thr Val Tyr Leu Gln Ile Asn Asn Leu Arg Asn Glu Asp Thr Ala
```

```
                   100                 105                 110
Thr Tyr Phe Cys Phe Ser Tyr Tyr Asp Tyr Trp Gly Gln Gly Thr Thr
            115                 120                 125

Leu Thr Val Ser Ser Gly Gly Gly Gly Ser Gly Gly Gly Ser Gly
        130                 135                 140

Gly Gly Gly Asp Ile Leu Leu Thr Gln Ser Pro Ala Ile Leu Ser Val
145                 150                 155                 160

Thr Pro Gly Glu Thr Val Ser Leu Ser Cys Arg Ala Ser Gln Thr Ile
                165                 170                 175

Tyr Lys Asn Leu His Trp Tyr Gln Gln Lys Ser His Arg Ser Pro Arg
            180                 185                 190

Leu Leu Ile Lys Tyr Gly Ser Asp Ser Ile Ser Gly Ile Pro Ser Arg
        195                 200                 205

Phe Thr Gly Ser Gly Ser Gly Thr Asp Tyr Thr Leu Asn Ile Asn Ser
        210                 215                 220

Val Lys Pro Glu Asp Glu Gly Ile Tyr Tyr Cys Leu Gln Gly Tyr Ser
225                 230                 235                 240

Thr Pro Trp Thr Phe Gly Gly Gly Thr Lys Leu Glu Ile Lys Thr Arg
                245                 250                 255

Cys

<210> SEQ ID NO 7
<211> LENGTH: 266
<212> TYPE: PRT
<213> ORGANISM: Artificial
<220> FEATURE:
<223> OTHER INFORMATION: 225.28 scFv (Vh1.Vk)

<400> SEQUENCE: 7

Ala Met Glu Phe Gly Leu Ser Trp Leu Phe Leu Val Ala Ile Leu Lys
1               5                   10                  15

Gly Val Gln Cys Lys Val Lys Leu Gln Glu Ser Gly Gly Gly Leu Val
            20                  25                  30

Gln Pro Gly Gly Ser Met Lys Leu Ser Cys Val Val Ser Gly Phe Thr
        35                  40                  45

Phe Ser Asn Tyr Trp Met Asn Trp Val Arg Gln Ser Pro Glu Lys Gly
    50                  55                  60

Leu Glu Trp Ile Ala Glu Ile Arg Leu Lys Ser Asn Asn Phe Ala Arg
65                  70                  75                  80

Tyr Tyr Ala Glu Ser Val Lys Gly Arg Phe Thr Ile Ser Arg Asp Asp
                85                  90                  95

Ser Lys Ser Ser Val Tyr Leu Gln Met Ile Asn Leu Arg Ala Glu Asp
            100                 105                 110

Thr Gly Ile Tyr Tyr Cys Thr Ser Tyr Gly Asn Tyr Val Gly His Tyr
        115                 120                 125

Phe Asp His Trp Gly Gln Gly Thr Thr Leu Thr Val Ser Ser Gly Gly
    130                 135                 140

Gly Gly Ser Gly Gly Gly Gly Ser Gly Gly Gly Gly Asp Ile Val Met
145                 150                 155                 160

Thr Gln Ser Gln Lys Phe Met Ser Thr Ser Val Gly Asp Arg Val Ser
                165                 170                 175

Val Thr Cys Lys Ala Ser Gln Asn Val Asp Thr Asn Val Ala Trp Tyr
            180                 185                 190

Gln Gln Lys Pro Gly Gln Ser Pro Glu Pro Leu Leu Phe Ser Ala Ser
        195                 200                 205
```

Tyr Arg Tyr Thr Gly Val Pro Asp Arg Phe Thr Gly Ser Gly Ser Gly
            210                 215                 220

Thr Asp Phe Thr Leu Thr Ile Ser Asn Val Gln Ser Glu Asp Leu Ala
225                 230                 235                 240

Glu Tyr Phe Cys Gln Gln Tyr Asn Ser Tyr Pro Leu Thr Phe Gly Gly
            245                 250                 255

Gly Thr Lys Leu Val Ile Lys Thr Arg Cys
            260                 265

<210> SEQ ID NO 8
<211> LENGTH: 266
<212> TYPE: PRT
<213> ORGANISM: Artificial
<220> FEATURE:
<223> OTHER INFORMATION: 225.28 scFv (Vk.Vh1)

<400> SEQUENCE: 8

Ala Met Glu Phe Gly Leu Ser Trp Leu Phe Leu Val Ala Ile Leu Lys
1               5                   10                  15

Gly Val Gln Cys Asp Ile Val Met Thr Gln Ser Gln Lys Phe Met Ser
            20                  25                  30

Thr Ser Val Gly Asp Arg Val Ser Val Thr Cys Lys Ala Ser Gln Asn
            35                  40                  45

Val Asp Thr Asn Val Ala Trp Tyr Gln Gln Lys Pro Gly Gln Ser Pro
50                  55                  60

Glu Pro Leu Leu Phe Ser Ala Ser Tyr Arg Tyr Thr Gly Val Pro Asp
65                  70                  75                  80

Arg Phe Thr Gly Ser Gly Ser Gly Thr Asp Phe Thr Leu Thr Ile Ser
            85                  90                  95

Asn Val Gln Ser Glu Asp Leu Ala Glu Tyr Phe Cys Gln Gln Tyr Asn
            100                 105                 110

Ser Tyr Pro Leu Thr Phe Gly Gly Gly Thr Lys Leu Val Ile Lys Gly
            115                 120                 125

Gly Gly Gly Ser Gly Gly Gly Gly Ser Gly Gly Gly Gly Lys Val Lys
130                 135                 140

Leu Gln Glu Ser Gly Gly Gly Leu Val Gln Pro Gly Gly Ser Met Lys
145                 150                 155                 160

Leu Ser Cys Val Val Ser Gly Phe Thr Phe Ser Asn Tyr Trp Met Asn
            165                 170                 175

Trp Val Arg Gln Ser Pro Glu Lys Gly Leu Glu Trp Ile Ala Glu Ile
            180                 185                 190

Arg Leu Lys Ser Asn Asn Phe Ala Arg Tyr Tyr Ala Glu Ser Val Lys
            195                 200                 205

Gly Arg Phe Thr Ile Ser Arg Asp Asp Ser Lys Ser Ser Val Tyr Leu
            210                 215                 220

Gln Met Ile Asn Leu Arg Ala Glu Asp Thr Gly Ile Tyr Tyr Cys Thr
225                 230                 235                 240

Ser Tyr Gly Asn Tyr Val Gly His Tyr Phe Asp His Trp Gly Gln Gly
            245                 250                 255

Thr Thr Leu Thr Val Ser Ser Thr Arg Cys
            260                 265

<210> SEQ ID NO 9
<211> LENGTH: 773
<212> TYPE: DNA
<213> ORGANISM: Artificial

<220> FEATURE:
<223> OTHER INFORMATION: scFv.763.74 VK2.VH1

<400> SEQUENCE: 9

| | | |
|---|---|---|
| tagccatgga attcggcctg agctggctgt tcctggtggc catcctgaag ggcgtgcagt | 60 |
| gcgatatcct gctcacccag tctccagcaa tcctgtctgt gactccagga gaaacagtca | 120 |
| gtctttcctg tagggccagc cagactattt acaagaacct acactggtat caacagaaat | 180 |
| cacatcggtc tccaaggctt ctcatcaagt atggttctga ttccatctct gggatcccct | 240 |
| ccaggttcac tggcagtgga tcagggacag attacactct caatatcaac agtgtgaagc | 300 |
| ccgaagatga aggaatatat tactgtcttc aaggttacag taccttgg acgttcggtg | 360 |
| gaggcaccaa gctggaaatc aaaggtgggg gcggttcagg cggaggtggc tctggcggtg | 420 |
| gcggacagat ccagttggtg cagtctggac ctgagctgaa gaagcctgga gagacagtca | 480 |
| agatctcctg caaggcttct ggttatacct tcacagacta ttcaatgcac tgggtgaaga | 540 |
| agactccagg aaagggttta aagtggctgg gctggataaa cactgcgact ggtgagccaa | 600 |
| catatgcaga tgacttcaag ggacggtttg ccatctcttt ggaaacctct gccaggactg | 660 |
| tctatttgca gatcaataat ctcagaaatg aggacacggc tacatatttc tgttttagtt | 720 |
| actacgacta ctggggccaa ggcaccactc tcacagtttc ctcaacgcgt tgc | 773 |

<210> SEQ ID NO 10
<211> LENGTH: 773
<212> TYPE: DNA
<213> ORGANISM: Artificial
<220> FEATURE:
<223> OTHER INFORMATION: scFv.763.74 VH1.VK2

<400> SEQUENCE: 10

| | | |
|---|---|---|
| tagccatgga attcggcctg agctggctgt tcctggtggc catcctgaag ggcgtgcagt | 60 |
| gccagatcca gttggtgcag tctggacctg agctgaagaa gcctggagag acagtcaaga | 120 |
| tctcctgcaa ggcttctggt tataccttca cagactattc aatgcactgg gtgaagaaga | 180 |
| ctccaggaaa gggtttaaag tggctgggct ggataaacac tgcgactggt gagccaacat | 240 |
| atgcagatga cttcaaggga cggtttgcca tctctttgga aacctctgcc aggactgtct | 300 |
| atttgcagat caataatctc agaaatgagg acacggctac atatttctgt tttagttact | 360 |
| acgactactg gggccaaggc accactctca cagtttcctc aggtggggc ggttcaggcg | 420 |
| gaggtggctc tggcggtggc ggagatatcc tgctcaccca gtctccagca atcctgtctg | 480 |
| tgactccagg agaaacagtc agtctttcct gtagggccag ccagactatt tacaagaacc | 540 |
| tacactggta tcaacagaaa tcacatcggt ctccaaggct ctcatcaag tatggttctg | 600 |
| attccatctc tgggatcccc tccaggttca ctggcagtgg atcagggaca gattacactc | 660 |
| tcaatatcaa cagtgtgaag cccgaagatg aaggaatata ttactgtctt caaggttaca | 720 |
| gtacaccttg acgttcggt ggaggcacca agctggaaat caaaacgcgt tgc | 773 |

<210> SEQ ID NO 11
<211> LENGTH: 800
<212> TYPE: DNA
<213> ORGANISM: Artificial
<220> FEATURE:
<223> OTHER INFORMATION: scFv225.28 VH1.VK

<400> SEQUENCE: 11

| | | |
|---|---|---|
| tagccatgga attcggcctg agctggctgt tcctggtggc catcctgaag ggcgtgcagt | 60 |

| | |
|---|---|
| gcaaggtgaa gctgcaggag tctggaggag gcttggtgca acctggagga tccatgaaac | 120 |
| tctcctgtgt tgtctctgga ttcactttca gtaattactg gatgaactgg gtccgccagt | 180 |
| ctccagagaa ggggcttgag tggattgcag aaattagatt gaaatccaat aattttgcaa | 240 |
| gatattatgc ggagtctgtg aagggaggt tcaccatctc aagagatgat tccaaaagta | 300 |
| gtgtctacct gcaaatgatc aacctaagag ctgaagatac tggcatttat tactgtacca | 360 |
| gttatggtaa ctacgttggg cactattttg accactgggg ccaaggcacc actctcacag | 420 |
| tctcctcagg tgggggcggt tcaggcggag gtggctctgg cggtggcgga gacattgtga | 480 |
| tgacccagtc tcaaaaattc atgtccacat cagtaggaga cagggtcagc gtcacctgca | 540 |
| aggccagtca gaatgtggat actaatgtag cctggtatca acaaaaacca gggcaatctc | 600 |
| ctgaaccact gcttttctcg gcatcctacc gttacactgg agtccctgat cgcttcacag | 660 |
| gcagtggatc tgggacagat ttcactctca ccatcagcaa tgtgcagtct gaagacttgg | 720 |
| cagagtattt ctgtcagcaa tataacagct atcctctgac gttcggtgga ggcaccaagc | 780 |
| tggtgatcaa aacgcgttgc | 800 |

<210> SEQ ID NO 12
<211> LENGTH: 800
<212> TYPE: DNA
<213> ORGANISM: Artificial
<220> FEATURE:
<223> OTHER INFORMATION: scFv225.28 VK.VH1

<400> SEQUENCE: 12

| | |
|---|---|
| tagccatgga attcggcctg agctggctgt tcctggtggc catcctgaag ggcgtgcagt | 60 |
| gcgacattgt gatgacccag tctcaaaaat tcatgtccac atcagtagga cagggtca | 120 |
| gcgtcacctg caaggccagt cagaatgtgg atactaatgt agcctggtat caacaaaaac | 180 |
| cagggcaatc tcctgaacca ctgcttttct cggcatccta ccgttacact ggagtccctg | 240 |
| atcgcttcac aggcagtgga tctgggacag atttcactct caccatcagc aatgtgcagt | 300 |
| ctgaagactt ggcagagtat ttctgtcagc aatataacag ctatcctctg acgttcggtg | 360 |
| gaggcaccaa gctggtgatc aaaggtgggg gcggttcagg cggaggtggc tctggcggtg | 420 |
| gcggaaaggt gaagctgcag gagtctggag gaggcttggt gcaacctgga ggatccatga | 480 |
| aactctcctg tgttgtctct ggattcactt tcagtaatta ctggatgaac tgggtccgcc | 540 |
| agtctccaga aggggcttg agtggattg cagaaattag attgaaatcc aataattttg | 600 |
| caagatatta tgcggagtct gtgaaaggga ggttcaccat ctcaagagat gattccaaaa | 660 |
| gtagtgtcta cctgcaaatg atcaacctaa gagctgaaga tactggcatt tattactgta | 720 |
| ccagttatgg taactacgtt gggcactatt ttgaccactg gggccaaggc accactctca | 780 |
| cagtctcctc aacgcgttgc | 800 |

<210> SEQ ID NO 13
<211> LENGTH: 15
<212> TYPE: PRT
<213> ORGANISM: Artificial
<220> FEATURE:
<223> OTHER INFORMATION: linker peptide

<400> SEQUENCE: 13

Gly Gly Gly Gly Ser Gly Gly Gly Gly Ser Gly Gly Gly Gly Ser
1               5                   10                  15

That which is claimed is:

1. A chimeric antigen receptor (CAR) comprising the amino acid sequences:

```
                                          (SEQ ID NO: 1)
QIQLVQSGPELKKPGETVKISCKASGYTFTDYSMHWVKKTPGKGLKWLG
WINTATGEPTYADDFKGRFAISLETSARTVYLQINNLRNEDTATYFCFS
YYDYWGQGTTLTVSS
and
                                          (SEQ ID NO: 2)
DILLTQSPAILSVTPGETVSLSCRASQTIYKNLHWYQQKSHRSPRLLIK
YGSDSISGIPSRFTGSGSGTDYTLNINSVKPEDEGIYYCLQGYSTPWTF
GGGTKLEIK,
``` linked together in any orientation,
wherein the CAR comprises SEQ ID NO:5 and/or SEQ ID NO:6.

2. The CAR of claim 1, comprising the amino acid sequence:

```
                                          (SEQ ID NO: 5)
  AM EFGL SWL FLV AILK GVQ CDI LLTQ SPA ILS

VTPG ETV SLS CRAS QTI YKN LHWY QQK SHR SPRL

LIK YGS DSIS GIP SRF TGSG SGT DYT LNIN SVK

PED EGIY YCL QGY STPW TFG GGT KLEI KGG GGS

GGGG SGG GGQ IQLV QSG PEL KKPG ETV KIS CKAS

GYT FTD YSMH WVK KTP GKGL KWL GWI NTAT GEP

TYA DDFK GRF AIS LETS ART VYL QINN LRN EDT

ATYF CFS YYD YWGQ GTT LTV SSTR C.
```

3. The CAR of claim 1, comprising the amino acid sequence:

```
                                          (SEQ ID NO: 6)
  AM EFGL SWL FLV AILK GVQ CQI QLVQ SGP ELK
KPGE TVK ISC KASG YTF TDY SMHW VKK TPG KGLK
WLG WIN TATG EPT YAD DFKG RFA ISL ETSA RTV
YLQ INNL RNE DTA TYFC FSY YDY WGQG TTL TVS
SGGG GSG GGG SGGG GDI LLT QSPA ILS VTP GETV
SLS CRA SQTI YKN LHW YQQK SHR SPR LLIK YGS
DSI SGIP SRF TGS GSGT DYT LNI NSVK PED EGI
YYCL QGY STP WTFG GGT KLE IKTR C.
```

4. The chimeric antigen receptor (CAR) of claim 1, further comprising a detectable moiety.

5. The CAR of claim 1, further comprising an effector molecule selected from the group consisting of a drug, a toxin, a small molecule, an antibody, a cytokine, an oncolytic virus, an enzyme, a nanoparticle, a biomaterial, a scaffold and any combination thereof.

6. A composition comprising the CAR of claim 1 in a pharmaceutically acceptable carrier.

7. A nucleic acid molecule encoding the CAR of claim 1.

8. A nucleic acid molecule encoding the CAR of claim 2, comprising the nucleotide sequence:

```
                                          (SEQ ID NO: 9)
TAGCCATGGAATTCGGCCTGAGCTGGCTGTTCCTGGTGGCCATCCTGAA

GGGCGTGCAGTGCGATATCCTGCTCACCCAGTCTCCAGCAATCCTGTCT

GTGACTCCAGGAGAAACAGTCAGTCTTTCCTGTAGGGCCAGCCAGACTA
```

-continued
```
TTTACAAGAACCTACACTGGTATCAACAGAAATCACATCGGTCTCCAAG

GCTTCTCATCAAGTATGGTTCTGATTCCATCTCTGGGATCCCCTCCAGG

TTCACTGGCAGTGGATCAGGGACAGATTACACTCTCAATATCAACAGTG

TGAAGCCCGAAGATGAAGGAATATATTACTGTCTTCAAGGTTACAGTAC

ACCTTGGACGTTCGGTGGAGGCACCAAGCTGGAAATCAAAGGTGGGGGC

GGTTCAGGCGGAGGTGGCTCTGGCGGTGGCGGACAGATCCAGTTGGTGC

AGTCTGGACCTGAGCTGAAGAAGCCTGGAGAGACAGTCAAGATCTCCTG

CAAGGCTTCTGGTTATACCTTCACAGACTATTCAATGCACTGGGTGAAG

AAGACTCCAGGAAAGGGTTTAAAGTGGCTGGGCTGGATAAACACTGCGA

CTGGTGAGCCAACATATGCAGATGACTTCAAGGGACGGTTTGCCATCTC

TTTGGAAACCTCTGCCAGGACTGTCTATTTGCAGATCAATAATCTCAGA

AATGAGGACACGGCTACATATTTCTGTTTTAGTTACTACGACTACTGGG

GCCAAGGCACCACTCTCACAGTTTCCTCAACGCGTTGC.
```

9. A nucleic acid molecule encoding the CAR of claim 3, comprising the nucleotide sequence:

```
                                          (SEQ ID NO: 10)
TAGCCATGGAATTCGGCCTGAGCTGGCTGTTCCTGGTGGCCATCCTGAA

GGGCGTGCAGTGCCAGATCCAGTTGGTGCAGTCTGGACCTGAGCTGAAG

AAGCCTGGAGAGACAGTCAAGATCTCCTGCAAGGCTTCTGGTTATACCT

TCACAGACTATTCAATGCACTGGGTGAAGAAGACTCCAGGAAAGGGTTT

AAAGTGGCTGGGCTGGATAAACACTGCGACTGGTGAGCCAACATATGCA

GATGACTTCAAGGGACGGTTTGCCATCTCTTTGGAAACCTCTGCCAGGA

CTGTCTATTTGCAGATCAATAATCTCAGAAATGAGGACACGGCTACATA

TTTCTGTTTTAGTTACTACGACTACTGGGGCCAAGGCACCACTCTCACA

GTTTCCTCAGGTGGGGGCGGTTCAGGCGGAGGTGGCTCTGGCGGTGGCG

GAGATATCCTGCTCACCCAGTCTCCAGCAATCCTGTCTGTGACTCCAGG

AGAAACAGTCAGTCTTTCCTGTAGGGCCAGCCAGACTATTTACAAGAAC

CTACACTGGTATCAACAGAAATCACATCGGTCTCCAAGGCTTCTCATCA

AGTATGGTTCTGATTCCATCTCTGGGATCCCCTCCAGGTTCACTGGCAG

TGGATCAGGGACAGATTACACTCTCAATATCAACAGTGTGAAGCCCGAA

GATGAAGGAATATATTACTGTCTTCAAGGTTACAGTACACCTTGGACGT

TCGGTGGAGGCACCAAGCTGGAAATCAAAACGCGTTGC.
```

10. A vector comprising the nucleic acid molecule of claim 7.

11. A cell comprising the CAR of claim 1.

12. A cell comprising the nucleic acid molecule of claim 7.

13. The cell of claim 11, wherein the cell is selected from the group consisting of a αβT cell, a natural killer (NK) cell, a cytotoxic T lymphocyte (CTL), a regulatory T cell, a natural killer T (NKT) cell, a Th17 cell, a γδT cell and any combination thereof.

14. A method of stimulating a T cell-mediated immune response to a CSPG4-expressing target cell population or tissue in a subject, comprising administering to the subject an effective amount of the nucleic acid molecule of claim 7, thereby stimulating a T cell-mediated immune response to the CSPG4 expressing target cell population or tissue in the subject.

15. The method of claim 14, wherein the subject has had and/or is having therapy for cancer.

16. A method of providing an anti-tumor immunity in a subject, comprising administering to the subject an effective amount of the nucleic acid molecule of claim 7, thereby providing an anti-tumor immunity in the subject.

17. A method of treating a subject having a disease or disorder associated with elevated expression of CSPG4 by a cell of the subject, comprising administering to the subject an effective amount of the nucleic acid molecule of claim 7, thereby treating the subject having the disease or disorder associated with elevated expression of CSPG4 by the cell of the subject.

18. A method of treating cancer in a subject, comprising administering to the subject an effective amount of the nucleic acid molecule of claim 7, thereby treating cancer in the subject.

19. A method of generating a population of genetically engineered cells in a subject, comprising administering to the subject a cell genetically engineered to express the CAR of claim 1, wherein the population of genetically engineered cells persists in the subject for a period of time following administration.

20. The method of claim 19, wherein the cell is selected from the group consisting of a an αβT cell, a natural killer (NK) cell, a cytotoxic T lymphocyte (CTL), a regulatory T cell, NKT cell, Th17 cell, a γδT cell and any combination thereof.

21. The method of claim 19, wherein the cell is an autologous cell.

22. A method of expanding a population of genetically engineered cells in a subject, comprising administering to the subject a cell genetically engineered to express the CAR of claim 1, wherein the administered genetically engineered cell produces a population of progeny cells in the subject.

23. A method of targeting a cancer cell and/or a cancer initiating cell (CIC) having a CSPG4 antigen, comprising providing to the cancer cell and/or the CIC a cell comprising the CAR of claim 1.

24. The method of claim 23, wherein the cancer cell and/or CIC is in vitro or in vivo.

25. The method of claim 23, wherein the cancer cell and/or the CIC is in a subject.

26. A method of detecting cancer cells and/or cancer initiating cells (CICs) in a cell sample, comprising:
   a) contacting the cell sample with the CAR of claim 1 under conditions whereby a binding complex can form; and
   b) detecting formation of the binding complex, wherein detection of the binding complex is indicative of cancer cells and/or CICs in the cell sample.

27. A method of detecting cancer cells and/or cancer initiating cells (CICs) in a subject, comprising:
   a) contacting a cell sample obtained from the subject with the CAR of claim 1 under conditions whereby a binding complex can form; and
   b) detecting formation of the binding complex, wherein detection of the binding complex is indicative of the presence of cancer cells and/or CICs in the subject.

* * * * *

UNITED STATES PATENT AND TRADEMARK OFFICE
CERTIFICATE OF CORRECTION

PATENT NO. : 12,428,490 B2
APPLICATION NO. : 17/251397
DATED : September 30, 2025
INVENTOR(S) : Dotti et al.

It is certified that error appears in the above-identified patent and that said Letters Patent is hereby corrected as shown below:

In the Specification

Column 5, Line 47-65: Please delete and replace with the following:
Further provided herein is a chimeric antigen receptor comprising, consisting essentially of or consisting of the amino acid sequence: AM EFGL SWL FLV AILK GVQ CDI VMTQ SQK FMS TSVG DRV SVT CKAS QNV DTN VAWY QQK PGQ SPEP LLF SAS YRYT GVP DRF TGSG SGT DFT LTIS NVQ SED LAEY FCQ QYN SYPL TFG GGT KLVI KGG GGS GGGG SGG GGK VKLQ ESG GGL VQPG GSM KLS CVVS GFT FSN YWMN WVR QSP EKGL EWI AEI RLKS NNF ARY YAES VKG RFT ISRD DSK SSV YLQM INL RAE DTGI YYC TSY GNYV GHY FDH WGQG TTL TVS STRC [225.28 scFv (Vk.Vh1)] (SEQ ID NO:8).

Column 10, Line 4: Please correct "PBS. T" to read --PBS, T--

Column 10, Line 36: Please correct "470) old." to read --470 old,--

Column 10, Line 58: Please correct "470) old." to read --470 old,--

Column 11, Line 13: Please correct "470) old." to read --470 old,--

Column 11, Line 16: Please correct "0)," to read --0,--

Column 11, Line 35: Please correct "470) old." to read --470 old,--

Column 19, Line 39: Please correct "one month two months," to read --one month, two months,--

Column 20, Lines 62-63: Please correct "B cell lymphoma. T" to read --B cell lymphoma, T--

Signed and Sealed this
Third Day of February, 2026

John A. Squires
*Director of the United States Patent and Trademark Office*

CERTIFICATE OF CORRECTION (continued)
U.S. Pat. No. 12,428,490 B2

Column 27, Line 38: Please correct "a carbon," to read --α carbon,--

Column 28, Line 14: Please correct "Basic amino acid"" to read --"Basic amino acid"--

Column 28, Line 17: Please correct "Aromatic amino acid"" to read --"Aromatic amino acid"--

Column 28, Line 20: Please correct "Hydrophobic amino acid"" to read --"Hydrophobic amino acid"--

Column 28, Line 24: Please correct "Neutral amino acid"" to read --"Neutral amino acid"--

Column 30, Line 53: Please correct "risking" to read --risk--

Column 32, Line 2: Please correct "modalities," to read --modalities.--

Column 32, Line 10: Please correct "and/o" to read --and/or--

Column 34, Line 34: Please correct "EP U.S." to read --EP--

Column 34, Line 35: Please correct "EP U.S." to read --EP--